US012790302B2

(12) United States Patent
Silcock et al.

(10) Patent No.: US 12,790,302 B2
(45) Date of Patent: Nov. 10, 2026

(54) CANNABINOID DERIVATIVES AS PHARMACEUTICALLY ACTIVE COMPOUNDS AND METHOD OF PREPARATION THEREOF

(71) Applicant: Jazz Pharmaceuticals Research UK Limited, Sittingbourne (GB)

(72) Inventors: Alan James Silcock, Sittingbourne (GB); Antoine Millet, Sittingbourne (GB); Karen Ka-Yen Tse, Sittingbourne (GB); Paul Stuart Hinchliffe, Sittingbourne (GB); Andrew Sharpe, Sittingbourne (GB); Iain David Simpson, Sittingbourne (GB); Joanne Peach, Sittingbourne (GB); Stefano Levanto, Sittingbourne (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 557 days.

(21) Appl. No.: 18/257,373

(22) PCT Filed: Dec. 15, 2021

(86) PCT No.: PCT/GB2021/053314

§ 371 (c)(1),
(2) Date: Jun. 14, 2023

(87) PCT Pub. No.: WO2022/129909

PCT Pub. Date: Jun. 23, 2022

(65) Prior Publication Data

US 2024/0025858 A1 Jan. 25, 2024

(30) Foreign Application Priority Data

Dec. 15, 2020 (GB) ...................................... 2019786
Mar. 26, 2021 (GB) ...................................... 2104278
Jul. 21, 2021 (GB) ...................................... 2110512

(51) Int. Cl.

| | |
|---|---|
| ***C07C 39/23*** | (2006.01) |
| ***A61K 31/415*** | (2006.01) |
| ***A61P 25/08*** | (2006.01) |
| ***C07C 41/30*** | (2006.01) |
| ***C07C 43/23*** | (2006.01) |
| ***C07C 213/08*** | (2006.01) |
| ***C07C 215/50*** | (2006.01) |
| ***C07D 213/14*** | (2006.01) |
| ***C07D 213/16*** | (2006.01) |
| ***C07D 213/64*** | (2006.01) |
| ***C07D 213/65*** | (2006.01) |
| ***C07D 213/74*** | (2006.01) |
| ***C07D 231/12*** | (2006.01) |

(Continued)

(52) U.S. Cl.

CPC ............ *C07D 231/12* (2013.01); *A61P 25/08* (2018.01); *C07C 39/23* (2013.01); *C07C 41/30* (2013.01); *C07C 43/23* (2013.01); *C07C 213/08* (2013.01); *C07C 215/50* (2013.01); *C07D 213/14* (2013.01); *C07D 213/16* (2013.01); *C07D 213/64* (2013.01); *C07D 213/65* (2013.01); *C07D 213/74* (2013.01); *C07D 233/64* (2013.01); *C07D 239/34* (2013.01); *C07D 249/06* (2013.01); *C07D 249/08* (2013.01); *C07D 261/08* (2013.01); *C07D 263/32* (2013.01); *C07D 271/06* (2013.01); *C07D 271/10* (2013.01); *C07D 405/04* (2013.01); *C07D 405/06* (2013.01)

(58) Field of Classification Search

CPC .. C07D 231/12; C07D 213/14; C07D 213/16; C07D 213/64; C07D 213/65; C07D 239/65; C07D 213/74; C07D 233/64; C07D 239/64; C07D 249/06; C07D 249/08; C07D 261/08; C07D 271/06; C07D 271/10; C07D 405/04; C07D 405/06; C07C 39/23; C07C 43/23; C07C 213/08; C07C 215/50; A61P 25/08; A61K 31/415

See application file for complete search history.

(56) References Cited

U.S. PATENT DOCUMENTS 6,630,507 B1 10/2003 Hampson et al.
8,632,825 B2 1/2014 Velasco Diez et al.
(Continued)

FOREIGN PATENT DOCUMENTS

CN 112592260 A 4/2021
JP 7744440 B2 9/2025
(Continued)

OTHER PUBLICATIONS

U.S. Appl. No. 15/640,033, filed Jun. 30, 2017.
(Continued)

*Primary Examiner* — Bruck Kifle
(74) *Attorney, Agent, or Firm* — COOLEY LLP

(57) ABSTRACT

The present invention relates to a group of novel compounds, methods for their manufacture and the use of these compounds as research tools and as pharmaceuticals. The novel compounds are analogues of cannabidiol (CBD). CBD is a non-psychoactive cannabinoid which has been used to treat various diseases and disorders. While such treatments hold promise, there remains a need in the art for more effective treatments and this has been brought about by way of novel cannabidiol compounds.

12 Claims, 13 Drawing Sheets

(51) Int. Cl.

| | |
|---|---|
| ***C07D 233/64*** | (2006.01) |
| ***C07D 239/34*** | (2006.01) |
| ***C07D 239/64*** | (2006.01) |
| ***C07D 249/06*** | (2006.01) |
| ***C07D 249/08*** | (2006.01) |
| ***C07D 261/08*** | (2006.01) |
| ***C07D 263/32*** | (2006.01) |
| ***C07D 271/06*** | (2006.01) |
| ***C07D 271/10*** | (2006.01) |
| ***C07D 405/04*** | (2006.01) |
| ***C07D 405/06*** | (2006.01) |

(56) References Cited

U.S. PATENT DOCUMENTS

| | | | |
|---|---|---|---|
| 8,790,719 | B2 | 7/2014 | Parolaro et al. |
| 9,017,737 | B2 | 4/2015 | Kikuchi et al. |
| 9,125,859 | B2 | 9/2015 | Whalley et al. |
| 9,474,726 | B2 | 10/2016 | Guy et al. |
| 9,675,654 | B2 | 6/2017 | Parolaro et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado et al. |
| 10,226,433 | B2 | 3/2019 | Di Marzo et al. |
| 10,583,096 | B2 | 3/2020 | Guy et al. |
| 10,603,288 | B2 | 3/2020 | Guy et al. |
| 10,653,641 | B2 | 5/2020 | Robson et al. |
| 10,709,671 | B2 | 7/2020 | Guy et al. |
| 10,709,673 | B2 | 7/2020 | Guy |
| 10,709,674 | B2 | 7/2020 | Guy et al. |
| 10,729,665 | B2 | 8/2020 | Whalley et al. |
| 10,758,514 | B2 | 9/2020 | Liu et al. |
| 10,765,643 | B2 | 9/2020 | Guy et al. |
| 10,799,467 | B2 | 10/2020 | Whalley et al. |
| 10,807,777 | B2 | 10/2020 | Whittle |
| 10,849,860 | B2 | 12/2020 | Guy et al. |
| 10,918,608 | B2 | 2/2021 | Guy et al. |
| 10,966,939 | B2 | 4/2021 | Guy et al. |
| 11,000,486 | B2 | 5/2021 | Wright et al. |
| 11,065,209 | B2 | 7/2021 | Guy et al. |
| 11,065,227 | B2 | 7/2021 | Stott et al. |
| 11,096,905 | B2 | 8/2021 | Guy et al. |
| 11,147,776 | B2 | 10/2021 | Stott et al. |
| 11,147,783 | B2 | 10/2021 | Stott et al. |
| 11,154,516 | B2 | 10/2021 | Guy et al. |
| 11,154,517 | B2 | 10/2021 | Guy et al. |
| 11,160,757 | B1 | 11/2021 | Wilkhu et al. |
| 11,160,795 | B2 | 11/2021 | Guy et al. |
| 11,207,292 | B2 | 12/2021 | Guy et al. |
| 11,229,612 | B2 | 1/2022 | Wright et al. |
| 11,291,631 | B2 | 4/2022 | Shah |
| 11,311,498 | B2 | 4/2022 | Guy et al. |
| 11,318,109 | B2 | 5/2022 | Whalley et al. |
| 11,357,741 | B2 | 6/2022 | Guy et al. |
| 11,400,055 | B2 | 8/2022 | Guy et al. |
| 11,406,623 | B2 | 8/2022 | Guy et al. |
| 11,413,266 | B2 | 8/2022 | Biróet al. |
| 11,419,829 | B2 | 8/2022 | Whalley et al. |
| 11,426,362 | B2 | 8/2022 | Wright et al. |
| 11,446,258 | B2 | 9/2022 | Guy et al. |
| 11,590,087 | B2 | 2/2023 | Guy et al. |
| 11,633,369 | B2 | 4/2023 | Guy et al. |
| 11,679,087 | B2 | 6/2023 | Guy et al. |
| 11,684,598 | B2 | 6/2023 | Stott et al. |
| 11,701,330 | B2 | 7/2023 | Guy et al. |
| 11,766,411 | B2 | 9/2023 | Guy et al. |
| 11,793,770 | B2 | 10/2023 | Stott et al. |
| 11,806,319 | B2 | 11/2023 | Wilkhu et al. |
| 11,865,102 | B2 | 1/2024 | Guy et al. |
| 11,963,937 | B2 | 4/2024 | Guy |
| 12,023,305 | B2 | 7/2024 | Whalley et al. |
| 12,064,398 | B2 | 8/2024 | Wright et al. |
| 12,064,399 | B2 | 8/2024 | Guy et al. |
| 12,102,619 | B2 | 10/2024 | Guy et al. |
| 12,121,499 | B2 | 10/2024 | Whalley et al. |
| 12,161,607 | B2 | 12/2024 | Wright et al. |
| 12,383,512 | B2 | 8/2025 | Guy et al. |
| 12,534,438 | B2 | 1/2026 | Silcock et al. |
| 2007/0072939 | A1 | 3/2007 | Kupper |
| 2012/0172339 | A1 | 7/2012 | Makriyannis et al. |
| 2015/0359755 | A1 | 12/2015 | Guy et al. |
| 2015/0359756 | A1 | 12/2015 | Guy et al. |
| 2017/0209390 | A1 | 7/2017 | Stott et al. |
| 2017/0239193 | A1 | 8/2017 | Guy et al. |
| 2018/0071210 | A1 | 3/2018 | Wilkhu et al. |
| 2018/0228751 | A1 | 8/2018 | Stott et al. |
| 2019/0167583 | A1 | 6/2019 | Shah |
| 2019/0314296 | A1 | 10/2019 | Wright et al. |
| 2019/0321307 | A1 | 10/2019 | Guy et al. |
| 2019/0365667 | A1 | 12/2019 | Wright et al. |
| 2020/0138738 | A1 | 5/2020 | Guy et al. |
| 2020/0179303 | A1 | 6/2020 | Guy et al. |
| 2020/0206152 | A1 | 7/2020 | Stott et al. |
| 2020/0206153 | A1 | 7/2020 | Whalley et al. |
| 2020/0237683 | A1 | 7/2020 | Whalley et al. |
| 2020/0277246 | A1* | 9/2020 | Gulko .................... C07C 39/23 |
| 2020/0297656 | A1 | 9/2020 | Guy et al. |
| 2020/0352878 | A1 | 11/2020 | Guy et al. |
| 2021/0015789 | A1 | 1/2021 | Guy et al. |
| 2021/0052512 | A1 | 2/2021 | Guy et al. |
| 2021/0059949 | A1 | 3/2021 | Wilkhu et al. |
| 2021/0059960 | A1 | 3/2021 | Wilkhu et al. |
| 2021/0059976 | A1 | 3/2021 | Wilkhu et al. |
| 2021/0069333 | A1 | 3/2021 | Velasco Diez et al. |
| 2021/0093581 | A1 | 4/2021 | Guy et al. |
| 2021/0100755 | A1 | 4/2021 | Whalley et al. |
| 2021/0145765 | A1 | 5/2021 | Guy et al. |
| 2021/0169824 | A1 | 6/2021 | Guy et al. |
| 2021/0177773 | A1 | 6/2021 | Guy et al. |
| 2021/0196651 | A1 | 7/2021 | Guy et al. |
| 2021/0267950 | A1 | 9/2021 | Guy et al. |
| 2021/0290565 | A1 | 9/2021 | Guy et al. |
| 2021/0308072 | A1 | 10/2021 | Wright et al. |
| 2021/0330636 | A1 | 10/2021 | Guy et al. |
| 2021/0401771 | A1 | 12/2021 | Guy et al. |
| 2022/0000800 | A1 | 1/2022 | Guy et al. |
| 2022/0008355 | A1 | 1/2022 | Guy et al. |
| 2022/0016048 | A1 | 1/2022 | Guy et al. |
| 2022/0023232 | A1 | 1/2022 | Guy et al. |
| 2022/0040155 | A1 | 2/2022 | Guy et al. |
| 2022/0062197 | A1 | 3/2022 | Stott et al. |
| 2022/0062211 | A1 | 3/2022 | Stott et al. |
| 2022/0087951 | A1 | 3/2022 | Knappertz |
| 2022/0096397 | A1 | 3/2022 | Wright et al. |
| 2022/0168266 | A1 | 6/2022 | Guy et al. |
| 2022/0183997 | A1 | 6/2022 | Guy et al. |
| 2022/0184000 | A1 | 6/2022 | Guy et al. |
| 2022/0202738 | A1 | 6/2022 | Guy et al. |
| 2022/0211629 | A1 | 7/2022 | Wilkhu et al. |
| 2022/0226257 | A1 | 7/2022 | Guy et al. |
| 2022/0233495 | A1 | 7/2022 | Silcock et al. |
| 2022/0249396 | A1 | 8/2022 | Guy et al. |
| 2022/0257529 | A1 | 8/2022 | Guy et al. |
| 2022/0265573 | A1 | 8/2022 | Guy et al. |
| 2022/0288055 | A1 | 9/2022 | Silcock et al. |
| 2022/0362149 | A1 | 11/2022 | Shah |
| 2022/0378714 | A1 | 12/2022 | Guy et al. |
| 2022/0378715 | A1 | 12/2022 | Guy et al. |
| 2022/0378738 | A1 | 12/2022 | Guy et al. |
| 2022/0387347 | A1 | 12/2022 | Whalley et al. |
| 2022/0395470 | A1 | 12/2022 | Whalley et al. |
| 2022/0395471 | A1 | 12/2022 | Guy et al. |
| 2023/0000789 | A1 | 1/2023 | Guy et al. |

(56) References Cited

U.S. PATENT DOCUMENTS

2023/0022487 A1 1/2023 Guy et al.
2023/0024312 A1 1/2023 Whalley et al.
2023/0026079 A1 1/2023 Guy et al.
2023/0032502 A1 2/2023 Guy et al.
2023/0038423 A1 2/2023 Silcock et al.
2023/0068885 A1 3/2023 Guy et al.
2023/0143812 A1 5/2023 Knappertz et al.
2023/0235825 A1 7/2023 Thompson et al.
2023/0248664 A1 8/2023 Guy
2023/0263744 A1 8/2023 Guy
2023/0277560 A1 9/2023 Checketts et al.
2023/0277561 A1 9/2023 Checketts et al.
2023/0277562 A1 9/2023 Checketts et al.
2023/0277563 A1 9/2023 Checketts et al.
2023/0285419 A1 9/2023 Checketts et al.
2023/0285420 A1 9/2023 Checketts et al.
2023/0285421 A1 9/2023 Checketts et al.
2023/0285422 A1 9/2023 Checketts et al.
2023/0285423 A1 9/2023 Checketts et al.
2023/0285424 A1 9/2023 Checketts et al.
2023/0285425 A1 9/2023 Checketts et al.
2023/0285426 A1 9/2023 Checketts et al.
2023/0285427 A1 9/2023 Checketts et al.
2023/0285428 A1 9/2023 Checketts et al.
2023/0301934 A1 9/2023 Whalley et al.
2023/0301936 A1 9/2023 Guy
2023/0310464 A1 10/2023 Checketts et al.
2023/0346809 A1 11/2023 Craig
2023/0372367 A1 11/2023 Checketts et al.
2023/0372368 A1 11/2023 Checketts et al.
2024/0016819 A1 1/2024 Craig
2024/0033229 A1 2/2024 Guy et al.
2024/0033272 A1 2/2024 Checketts et al.
2024/0043388 A1 2/2024 Silcock et al.
2024/0050452 A1 2/2024 Craig et al.
2024/0091241 A1 3/2024 Guy et al.
2024/0165048 A1 5/2024 Guy
2024/0207220 A1 6/2024 Guy et al.
2024/0215910 A1 7/2024 Tse et al.
2024/0226032 A9 7/2024 Wilkhu et al.
2024/0226123 A9 7/2024 Tse
2024/0238218 A1 7/2024 Silcock et al.
2024/0254066 A1 8/2024 Silcock et al.
2024/0254072 A1 8/2024 Silcock et al.
2024/0261234 A1 8/2024 Guy
2024/0293762 A1 9/2024 Loft et al.
2024/0350428 A1 10/2024 Guy et al.
2024/0360060 A1 10/2024 Silcock et al.
2025/0376446 A1 12/2025 Straker et al.

FOREIGN PATENT DOCUMENTS

WO WO-9953917 A1 10/1999
WO WO-0129007 A1 4/2001
WO WO-2005023741 A2 3/2005
WO WO-2011006099 A1 1/2011
WO WO-2014062965 A1 4/2014
WO WO-2014134127 A1 9/2014
WO WO-2014159688 A1 10/2014
WO WO-2015193667 A1 12/2015
WO WO-2015193668 A1 12/2015
WO WO-2016094810 A2 6/2016
WO WO-2016203239 A1 12/2016
WO WO-2018061007 A1 4/2018
WO WO-2018205022 A1 11/2018
WO WO-2020031179 A1 2/2020
WO WO-2020104796 A1 5/2020
WO WO-2020232545 A1 11/2020
WO WO-2021097351 A1 5/2021
WO WO-2021099781 A1 5/2021
WO WO-2021099783 A1 5/2021
WO WO-2022129868 A2 * 6/2022 ......... G01N 33/9473
WO WO-2022129908 A1 6/2022
WO WO-2022129909 A1 6/2022
WO WO-2022238707 A1 11/2022

OTHER PUBLICATIONS

U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/472,000, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/576,868, filed Jan. 14, 2022.
U.S. Appl. No. 17/585,485, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/817,753, filed Aug. 5, 2022.
U.S. Appl. No. 17/853,367, filed Jun. 29, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18,006,131, filed Jan. 19, 2023.
U.S. Appl. No. 18,006,133, filed Jan. 19, 2023.
U.S. Appl. No. 18/006,121, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/320,906, filed May 19, 2023.
U.S. Appl. No. 18/256,307, filed Jun. 7, 2023.

(56) References Cited

OTHER PUBLICATIONS

U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
U.S. Appl. No. 18/560,316, filed Nov. 10, 2023.
U.S. Appl. No. 18/560,337, filed Nov. 10, 2023.
U.S. Appl. No. 18/560,341, filed Nov. 10, 2023.
U.S. Appl. No. 18/560,346, filed Nov. 10, 2023.
U.S. Appl. No. 18/526,795, filed Dec. 1, 2023.
Elsohly, M. & Gul, W., Handbook of Cannabis, Chapter 1, Constituents of Cannabis Sativa, Roger Pertwee, Ed., 2012, 21 pages.
EPIDIOLEX® (cannabidiol) oral solution, CV, Prescribing Information, 2018, 30 pages; https://www.accessdata.fda.gov/drugsatfda_docs/label/2018/210365lbl.pdf.
Gong, X. et al., "Synthesis of CBD and Its Derivatives Bearing Various C4'-Side Chains with a Late-Stage Diversification Method," J. Org. Chem., 85:2704-2715 (2020).
Kimball, A. W. et al., "Chemical Protection against Ionizing Radiation, Radiation Research," 7:1-12 (1957).
Lago-Fernandez, A. et al., "New Methods for the Synthesis of Cannabidiol Derivatives," Methods in Enzymology, 593:237-257 (2017).
Lazarini-Lopes, W. et al., "The anticonvulsant effects of cannabidiol in experimental models of epileptic seizures: From behavior and mechanisms to clinical insights," Neuroscience and Biobehavioral Reviews, 111:166-182 (2020).
Litchfield, J. T. & Wilcoxon, F., "A simplified method of evaluating dose-effect experiments," J Pharmacol Exp Ther, 96(2):99-113 (1949).
Pertwee, R. G., "The Pharmacology and Therapeutic Potential of Cannabidiol," Cannabinoids, Chapter 3, DiMarzo, V. (Ed.), pp. 32-83 (2004).
Caira, M. R., "Crystalline Polymorphism of Organic Compounds," In: Weber, E., et al. Design of Organic Solids. Topics in Current Chemistry, 198:163-208, Springer, Berlin, Heidelberg (Sep. 1998); https://doi.org/10.1007/3-540-69178-2_5.
CAS Registry, CAS RN 1260669-33-7, "1,3-Benzenediol, 5-iodo-2-[(1R,6R)-3-methyl-6-(1-methylethenyl)-2-cyclohexen-1-yl]," [chemical database], Chemical Abstracts Service. [Accessed May 28, 2026, not publicly available], 1 page.
CAS Registry, CAS RN 58940-28-6, "1,3-Benzenediol, 2-[(1R,4S,6R)-4-hydroxy-3-methyl-6-(1-methylethenyl)-2-cyclohexen-1-yl]-5-pentyl," [chemical database], Chemical Abstracts Service. [Accessed May 28, 2026, not publicly available], 1 page.
Crowley, M. M., "Solutions, Emulsions, Suspensions, and Extracts," In: Remington's Pharmaceutical Sciences, The Science and Practice of Pharmacy, Chapter 39, 21st Edition, New York, NY: Lippincott Williams and Wilkins, May 2005, 38 Pages.
De Meijer, E. P. M., "The Chemical Phenotypes (Chemotypes) of Cannabis," Chapter 5, In: Handbook of Cannabis, Ed. Roger G. Pertwee, Oxford University Press, Oxford, pp. 89-110 (Aug. 2014); https://doi.org/10.1093/acprof:oso/9780199662685.003.0005.
Emmet G.C., "Synthesis of 6 Hydroxy-8,9-dihydrocannabidiol," [Ph. D. dissertation], University of Delaware, Delaware, May 1973, 73 Pages.
Hilfiker, R. et al., "Relevance of Solid-state Properties for Pharmaceutical Products," Polymorphism: in the Pharmaceutical Industry, Jan. 2006 (Jan. 2006), Wiley-VCH GmbH, Weinheim, pp. 1-19.
Li, H. et al., "Overview of Cannabidiol (CBD) and Its Analogues: Structures, Biological Activities, and Neuroprotective Mechanisms in Epilepsy and Alzheimer's Disease," European Journal of Medicinal Chemistry, 112163, vol. 192, pp. 1-14 (Feb. 2020).
Löscher, W. et al., "The role of technical, biological and pharmacological factors in the laboratory evaluation of anticonvulsant drugs. II. Maximal electroshock seizure models," Epilepsy Res., 8:79-94 (Mar. 1991); doi: 10.1016/0920-1211(91)90075-q.
Millar, S. A. et al., "Towards Better Delivery of Cannabidiol (CBD)," Pharmaceuticals, 13:219 (Sep. 2020); doi:10.3390/ph13090219, 15 pages.
Potter, D. J., "Cannabis Horticulture," Chapter 4, Handbook of Cannabis, Ed. Roger G. Pertwee, New York, New York: Oxford University Press, pp. 65-88 (Aug. 2014).
Silva, G. D. et al., "Cannabidiol in the Treatment of Epilepsy: A Focused Review of Evidence and Gaps," Frontiers in Neurology, 11:531939 (Oct. 2020), 6 pages; doi: 10.3389/fneur.2020.531939. eCollection 2020.
The Chemical Society of Japan (Ed.), Experimental Chemistry Course 18: Reactions of Organic Compounds I (Lower), Maruzen Group K.K, Oct. 31, 1958, pp. 403-404, with machine translated English Patent Technical Summary, 5 total pages.
The Chemical Society of Japan (Ed.), Experimental Chemistry Series, vol. 14: Synthesis of Organic Compounds II Alcohols and Amines, 5th ed., Maruzen Co., Ltd., pp. 52-56 (Aug. 31, 2005), with machine translated English Abstract, 8 total pages.
Vanlandingham, K. E. et al., "A Phase 2, Double-Blind, Placebo-Controlled Trial to Investigate Potential Drug-Drug Interactions Between Cannabidiol and Clobazam," J Clin Pharmacol., 60(10):1304-1313 (Oct. 2020); doi: 10.1002/jcph.1634. Epub Jul. 11, 2020.
Vree, T. B. et al., "Identification of hashish of tetrahydrocannabinol, cannabidiol and cannabinol analogues with a methyl side-chain," J. Pharm. Pharmac. 24:7-12 (Sep. 1971); doi: 10.1111/j.2042-7158.1972.tb08857.x.
Anagnostaki, E. E. & Zografo, A. L., "Non-natural elemane as the "stepping stone" for the synthesis of germacrane and guaiane sesquiterpenes," Org Lett, 15(1):152-155 (2013); doi: 10.1021/013031999. Epub Dec. 20, 2012.
Bailey, S. et al., "Lewis-Acid-Mediated Union of Epoxy-Carvone Diastereomers with Anisole Derivatives: Mechanistic Insight and Application to the Synthesis of Non-natural CBD Analogues," Org. Lett., 20:4618-4621 (2018).
Brown, W. C. et al., "Comparative Assay of Antiepileptic Drugs by "Psychomotor" Seizure Test and Minimal Electroshock Threshold Test," J. Pharmacol. Exp. Ter., 107: 273-283 (1953).
Durmuller, N. et al., "Proconvulsant and anticonvulsant effects of Evans blue dye in rodents," NeuroReport, 4(6):683-686 (1993).
Eadie, M. J., "Shortcomings in the current treatment of epilepsy," Expert Rev Neurother., 12(12):1419-1427 (2012).
Fisher, R.,S. et al., "A practical definition of epilepsy," Epilepsia, 55(4):475-482 (2014).
Fisher, R. S. et al., "Operational classification of seizure types by the International League Against Epilepsy: Position Paper of the ILAE Commission for Classification and Terminology," Epilepsia, 58(4):522-530 (2017); doi: 10.1111/epi.13670. Epub Mar. 8, 2017.
Harvey, D. J., "Characterization of the Butyl Homologues of Delta1-tetrahydrocannabinol, Cannabinol and Cannabidiol in Samples of Cannabis by Combined Gas Chromatography and Mass Spectrometry," J. Pharm. Pharmac., 28:280-285 (1976).
Hill, "Cannabidivarin-rich cannabis extracts are anticonvulsant in mouse and rat via a CB 1 receptor-independent mechanism," British Journal of Pharmacology, 170(3):679-692 (2013).
Jiang, R. et al., "Identification of cytochrome P450 enzymes responsible for metabolism of cannabidiol by human liver microsomes," Life Sciences, 89(5):165-170 (2011).
Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.
Lander, N. et al., "Total Syntheses of Cannabidiol and Δ1-Tetrahydrocannabiinol Metabolites," J Chem Soc Perkin 1, (1):8-16 (1976).
Morales, P. et al., "An Overview on Medicinal Chemistry of Synthetic and Natural Derivatives of Cannabidiol," Frontiers in Pharmacology, 8:422 (2017); doi:10.3389/fphar.2017.00422, 18 pages.
Naik, R. H. et al., "Cannibinoid Derivative," Indian Journal of Chemistry, pp. 306-307, Apr. 4, 1987, XP055942064, 1 page.

(56) References Cited

OTHER PUBLICATIONS

Shing, T. K. M. et al., "Mild Manganese (III) Acetate Catalyzed Allylic Oxidation: Application to Simple and Complex Alkalenes," Organic Letters, 8(14):3149-3151 (2006).
Thurman, D. J. et al., "Standards for epidemiologic studies and surveillance of epilepsy," Epilepsia, 52 (Suppl 7):2-26 (2011).

* cited by examiner

Figure 1. Effect of Compound 1 on the electroshock-induced generalised seizure threshold (mini-MEST) in the mouse
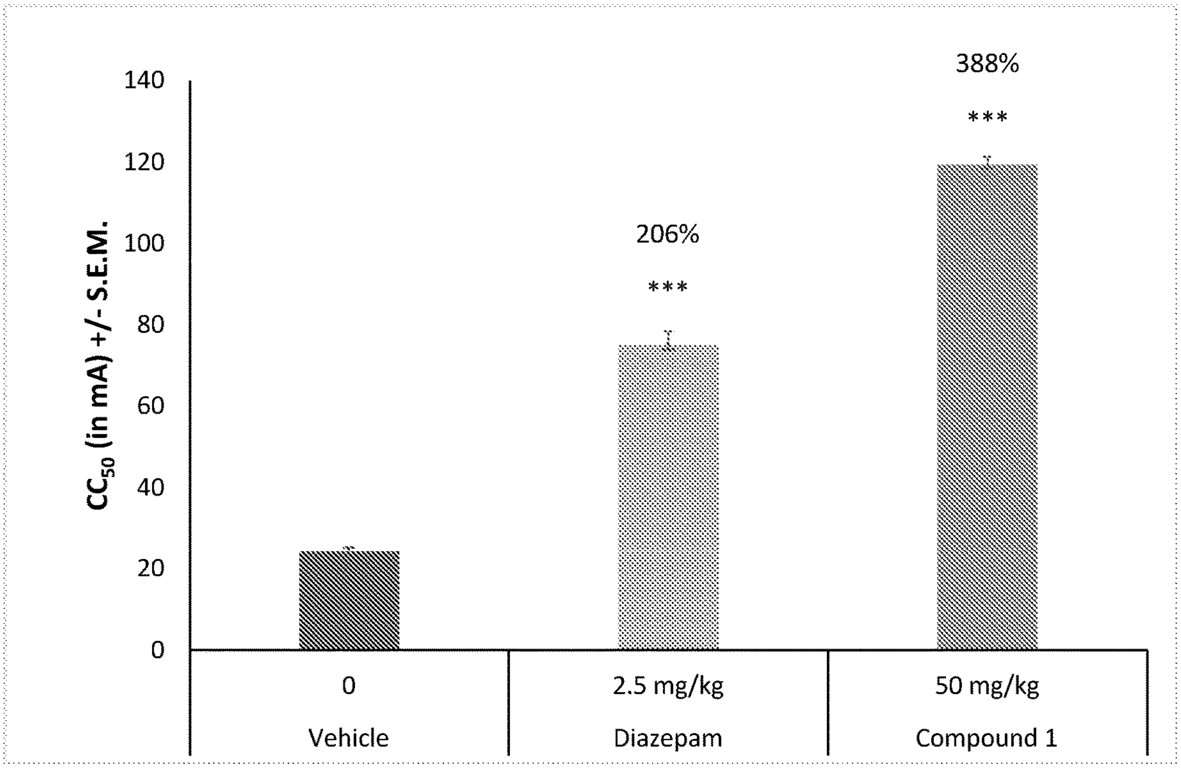
***p<0.001 when compared to the vehicle group

Figure 2. Effect of Compounds 2 and 3 on the electroshock-induced generalised seizure threshold (mini-MEST) in the mouse
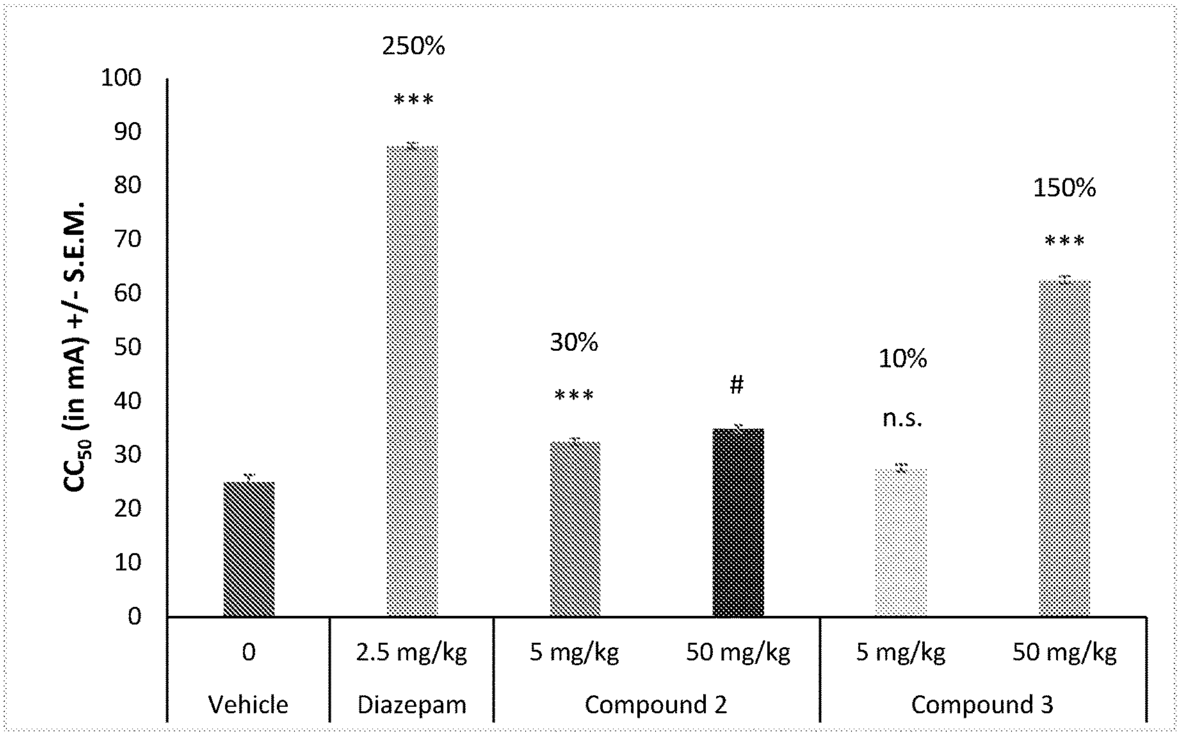
***p<0.001 when compared to the vehicle group
Statistical significance not determined as $CC_{50}$ was not reached
n.s. – No statistically significant differences from vehicle was observed

Figure 3. Effect of Compounds 4 and 5 on the electroshock-induced generalised seizure threshold (mini-MEST) in the mouse
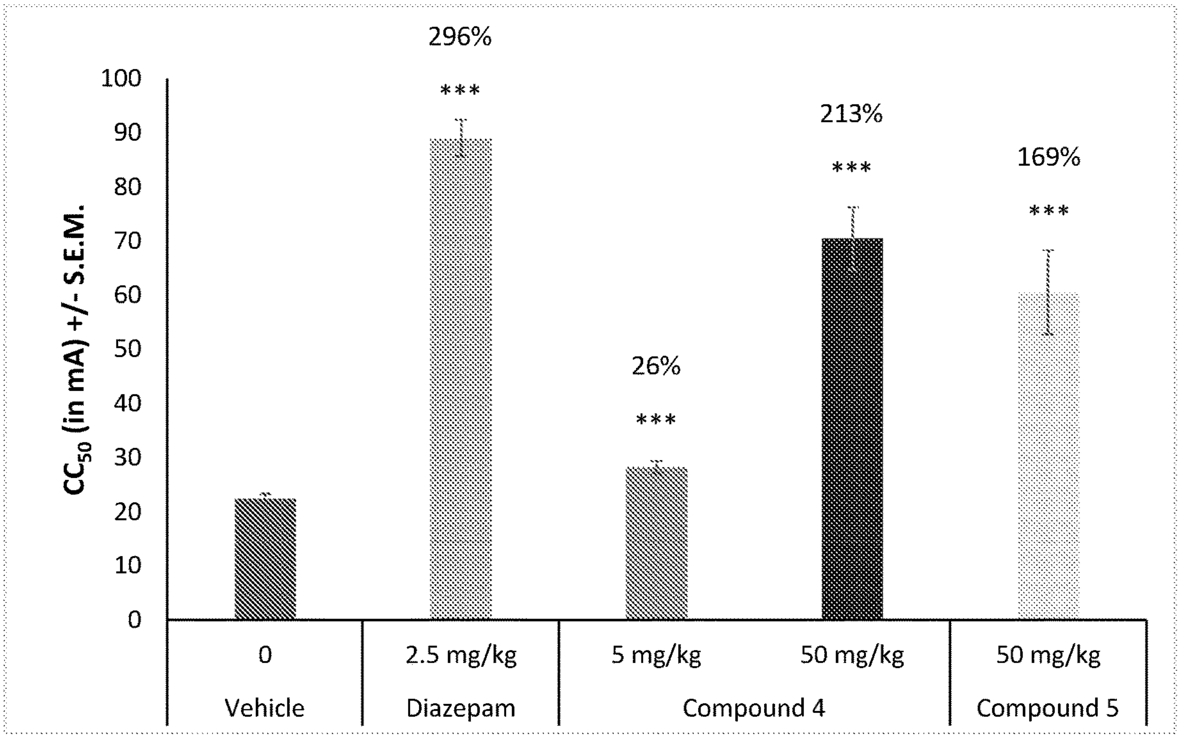
***p<0.001 when compared to the vehicle group

Figure 4. Effect of Compound 12 on the electroshock-induced generalised seizure threshold (mini-MEST) in the mouse
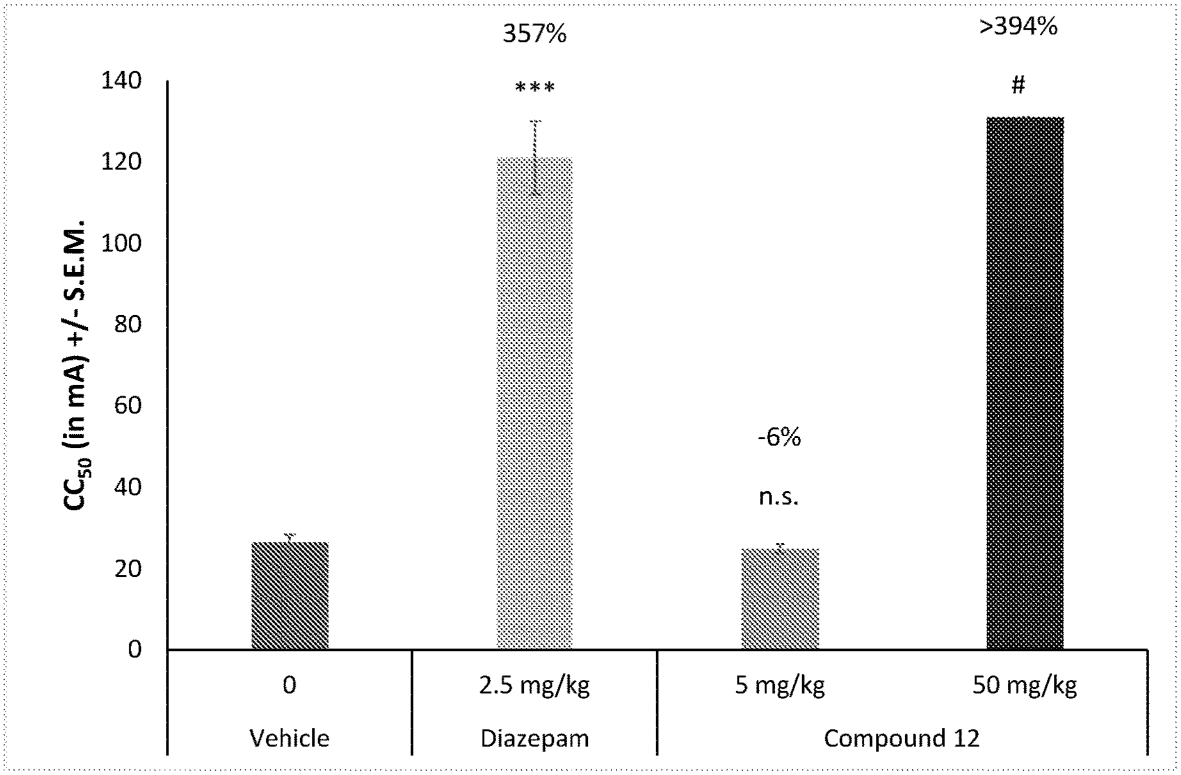
***p<0.001 when compared to the vehicle group
Statistical significance not determined as $CC_{50}$ was not reached
n.s. – No statistically significant differences from vehicle was observed

Figure 5. Effect of Compound 42 on the electroshock-induced generalised seizure threshold (mini-MEST) in the mouse
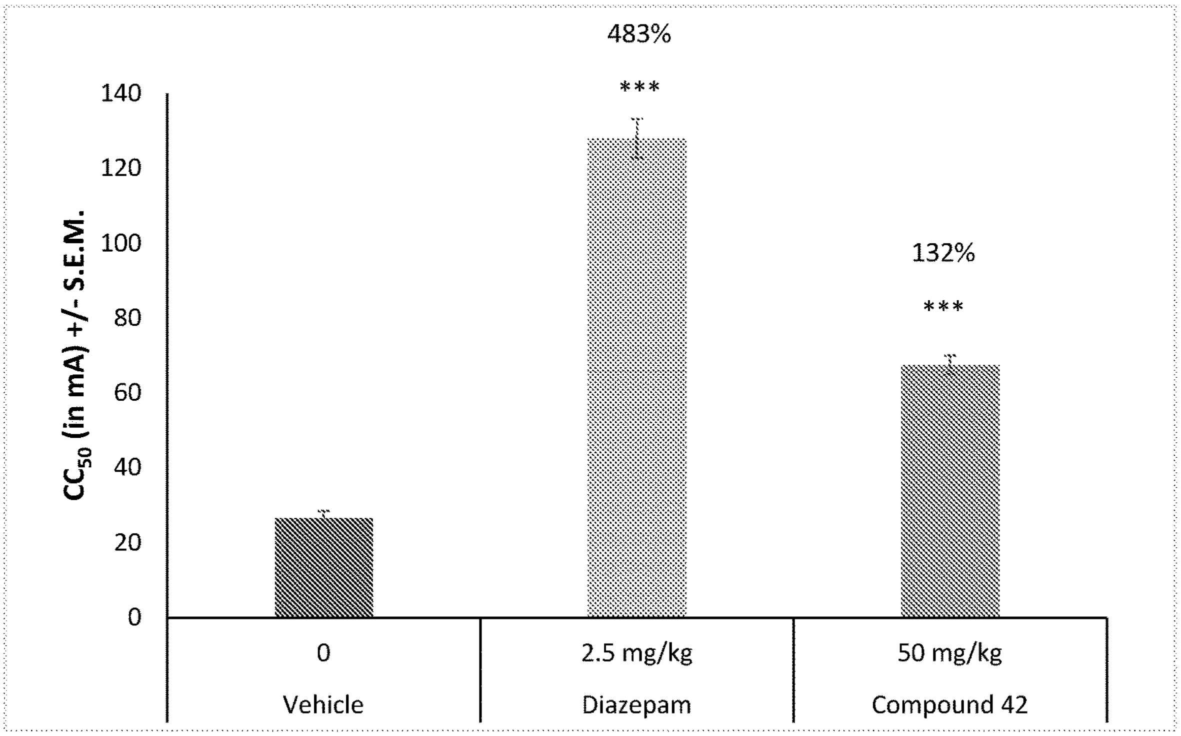
***p<0.001 when compared to the vehicle group

Figure 6. Effect of Compound 43 on the electroshock-induced generalised seizure threshold (mini-MEST) in the mouse
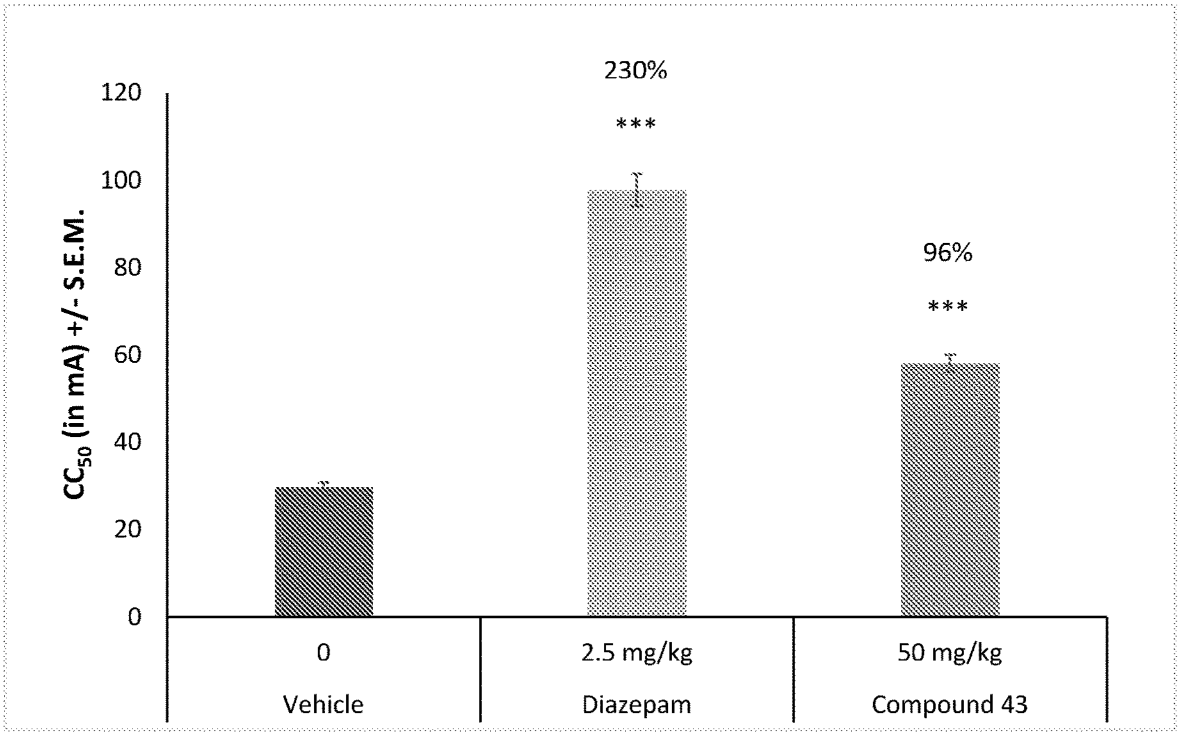
***p<0.001 when compared to the vehicle group

Figure 7. Effect of Compound 1 on the electroshock-induced generalised seizure threshold (MEST) in the mouse
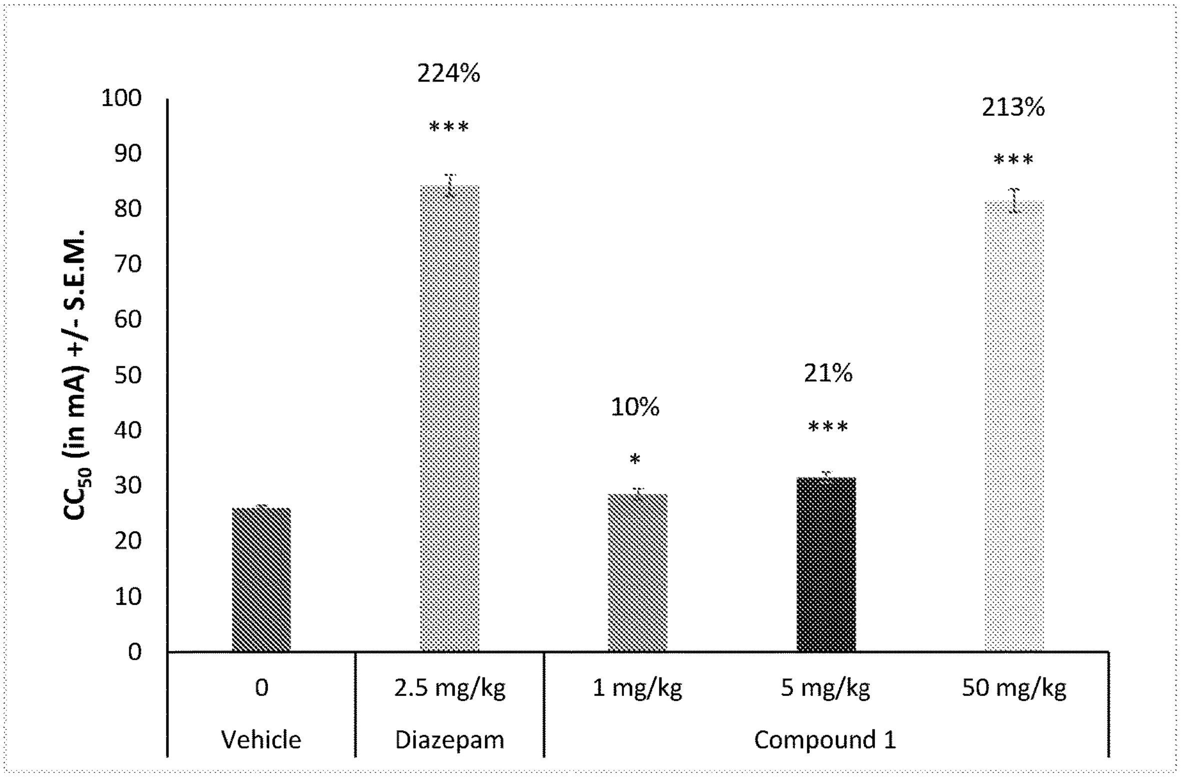
*p<0.05 when compared to the vehicle group
***p<0.001 when compared to the vehicle group

Figure 8. Effect of Compound 6 on the electroshock-induced generalised seizure threshold (mini-MEST) in the mouse
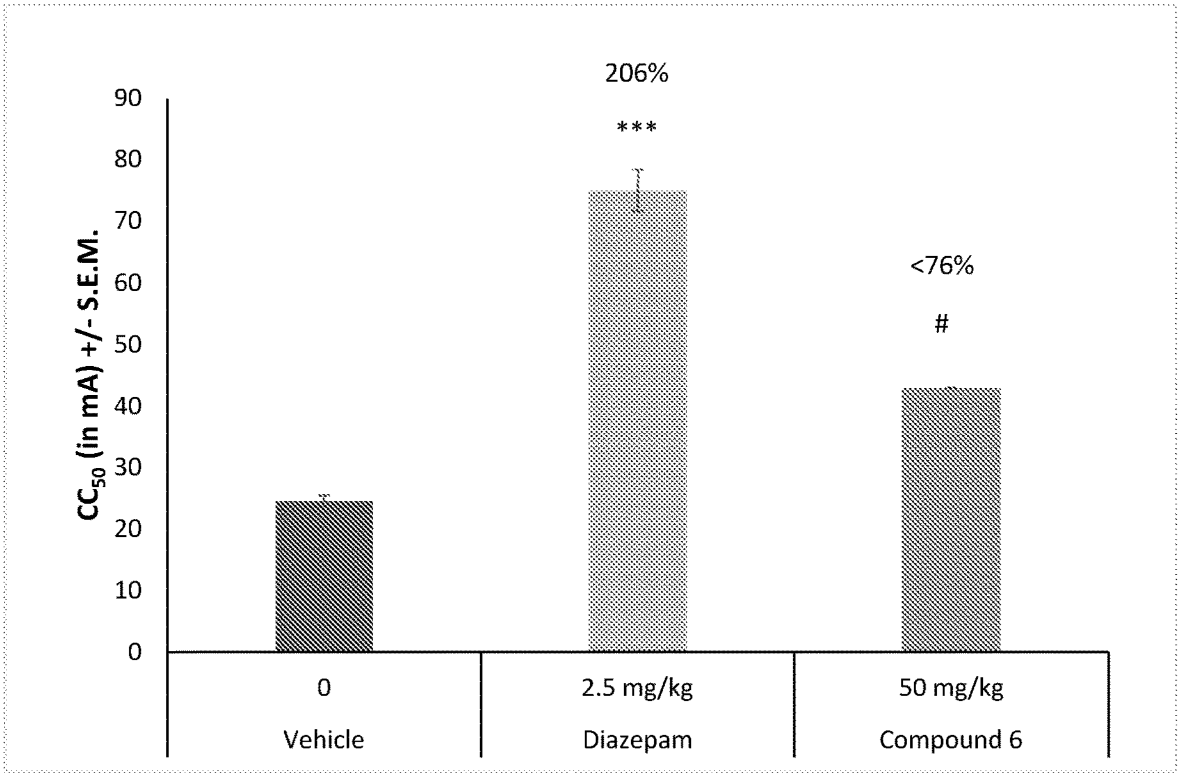
***p<0.001 when compared to the vehicle group
Statistical significance not determined as $CC_{50}$ was not reached Figure 9. Effect of Compound 13 on the electroshock-induced generalised seizure threshold (mini-MEST) in the mouse
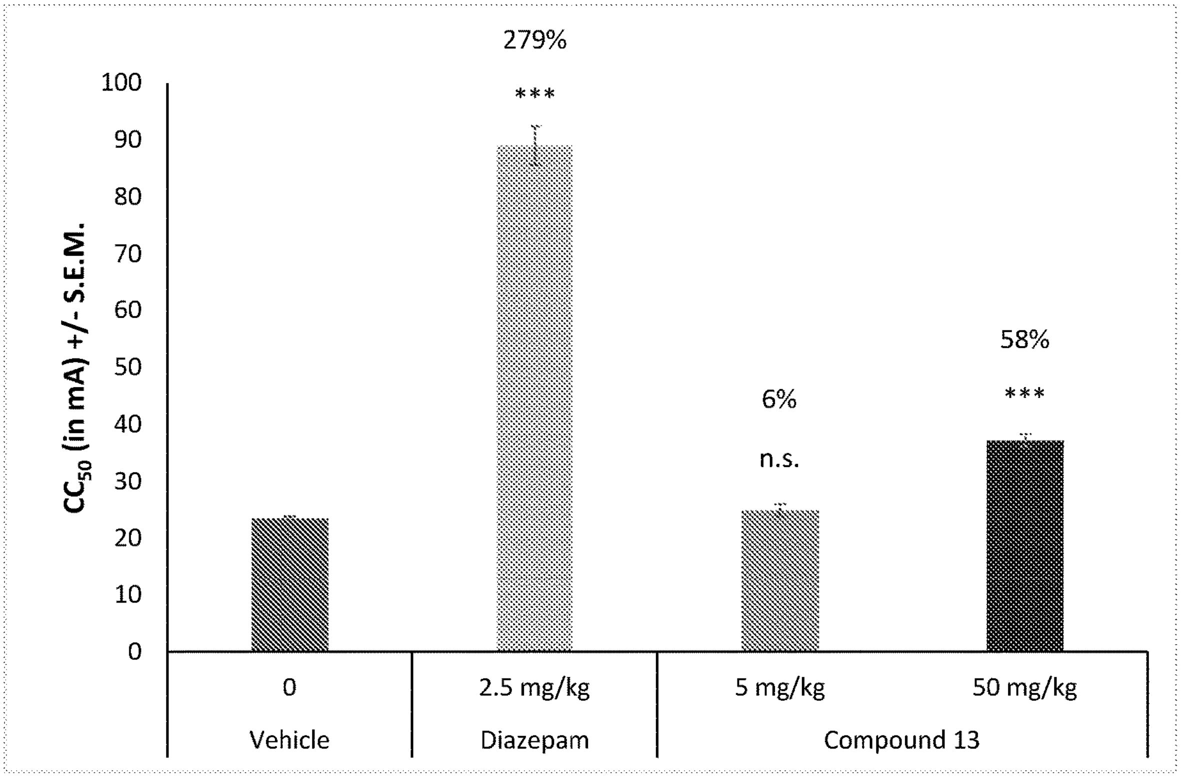
***p<0.001 when compared to the vehicle group
n.s. – No statistically significant differences from vehicle was observed

Figure 10. Effect of Compounds 22 and 38 on the electroshock-induced generalised seizure threshold (mini-MEST) in the mouse
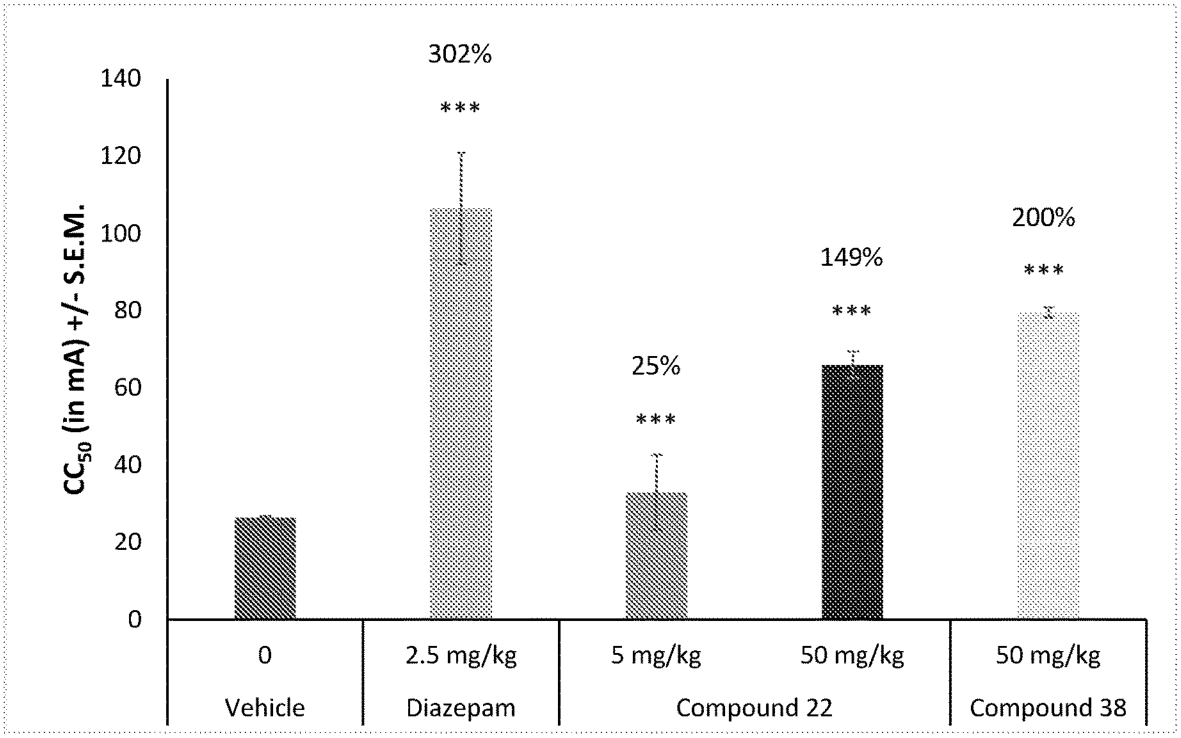
***p<0.001 when compared to the vehicle group

Figure 11. Effect of Compounds 26, 28 and 33 on the electroshock-induced generalised seizure threshold (mini-MEST) in the mouse
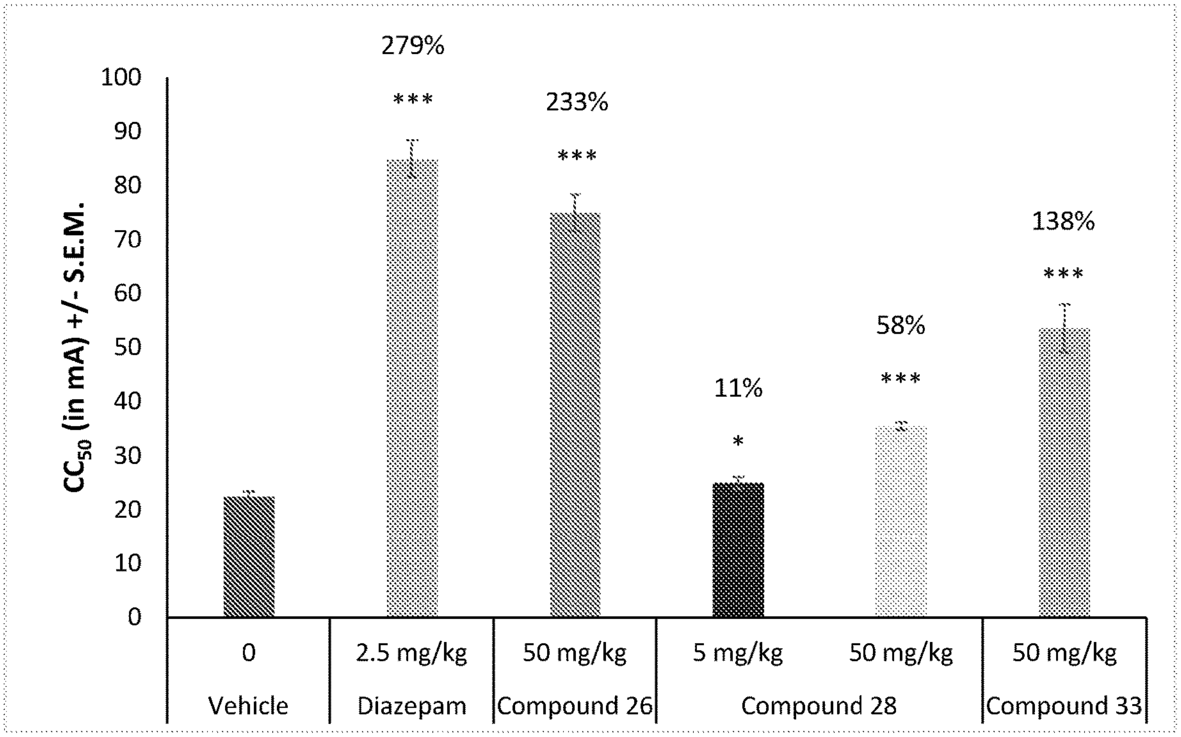
*p<0.05 when compared to the vehicle group
***p<0.001 when compared to the vehicle group

Figure 12. Effect of Compound 46 on the electroshock-induced generalised seizure threshold (mini-MEST) in the mouse
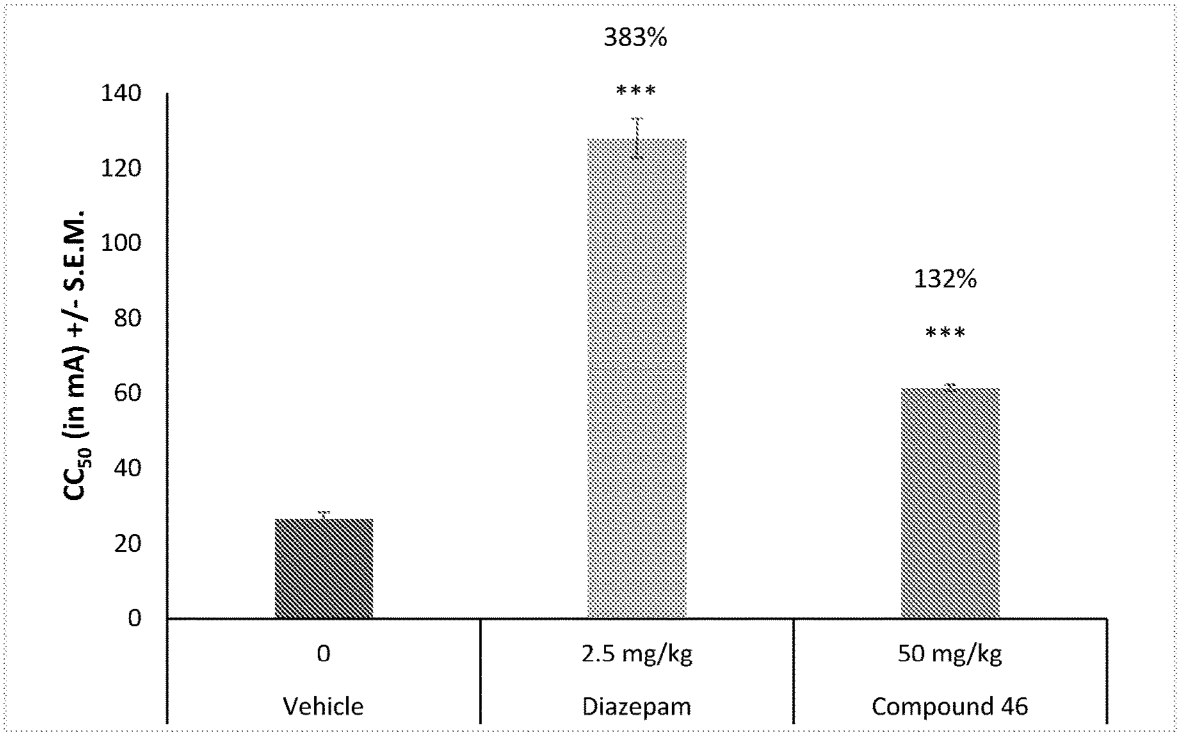
***p<0.001 when compared to the vehicle group

Figure 13. Effect of Compound 36 on the electroshock-induced generalised seizure threshold (mini-MEST) in the mouse
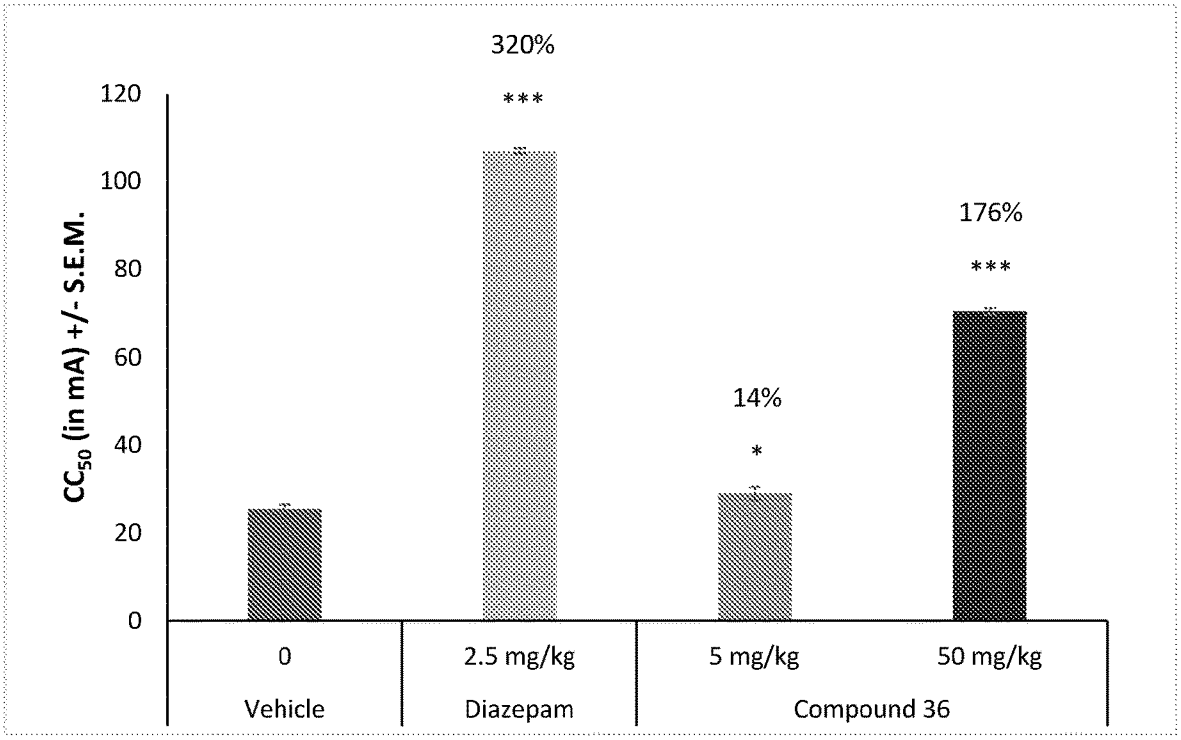
*p<0.05 when compared to the vehicle group
***p<0.001 when compared to the vehicle group

CANNABINOID DERIVATIVES AS PHARMACEUTICALLY ACTIVE COMPOUNDS AND METHOD OF PREPARATION THEREOF

CROSS-REFERENCE TO RELATED APPLICATIONS

This application is a U.S. National Phase application, filed under 35 U.S.C. § 371(c), of International Application No. PCT/GB2021/053314, filed Dec. 15, 2021, which claims priority to, and the benefit of, GB 2110512.7, filed Jul. 21, 2021, GB 2104278.3, filed Mar. 26, 2021 and GB 2019786.9, filed Dec. 15, 2020. Each of these documents is incorporated by reference herein in its entirety for all purposes.

FIELD OF THE INVENTION

The present invention relates to a group of novel compounds, methods for their manufacture and the use of these compounds as research tools and as pharmaceuticals.

The novel compounds are analogues of cannabidiol (CBD). CBD is a non-psychoactive cannabinoid which has been used to treat various diseases and disorders. While such treatments hold promise, there remains a need in the art for more effective treatments and this has been brought about by way of novel cannabidiol compounds.

BACKGROUND TO THE INVENTION

Cannabinoids are natural and synthetic compounds structurally or pharmacologically related to the constituents of the *Cannabis* plant or to the endogenous agonists (endocannabinoids) of the cannabinoid receptors CB1 or CB2. The only way in nature in which these compounds are produced is by the *Cannabis* plant. *Cannabis* is a genus of flowering plants in the family Cannabaceae, comprising the species *Cannabis sativa, Cannabis indica*, and *Cannabis ruderalis* (sometimes considered as part of *Cannabis sativa*).

*Cannabis* plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPR5. The principle cannabinoids present in *Cannabis* plants are cannabinoid acids Δ9-tetrahydrocannabinolic acid (Δ9-THCA) and cannabidiolic acid (CBDA) with small amounts of their respective neutral (decarboxylated) cannabinoids. In addition, *Cannabis* may contain lower levels of other minor cannabinoids.

There are currently four cannabinoid-based pharmaceutical approved products on the market. These are: dronabinol (Marinol®) which is a synthetic tetrahydrocannabinol (THC) approved for the treatment of loss of appetite in AIDS and the treatment of severe nausea and vomiting caused by cancer chemotherapy; nabilone (Cesamet®) which is a synthetic cannabinoid and an analog of THC which is approved for the treatment of nausea and vomiting caused by cytotoxic chemotherapy unresponsive to conventional antiemetics; nabiximols (Sativex®) a mixture of two *Cannabis* plant extracts approved for the treatment of neuropathic pain, spasticity, overactive bladder, and other symptoms of multiple sclerosis; and highly purified botanical CBD (Epidiolex®) approved in the United States for the treatment of Dravet syndrome and Lennox-Gastaut syndrome in children and adults over the age of 2 years.

As can be seen above cannabinoids are a class of compounds which may be derived naturally from the *Cannabis* plant or produced semi-synthetically or synthetically via chemical synthesis.

More than 100 different cannabinoids have been identified. These cannabinoids can be split into different groups as follows: phytocannabinoids; endocannabinoids and synthetic cannabinoids (which may be novel cannabinoids or synthetically produced versions of phytocannabinoids or endocannabinoids). The Handbook of *Cannabis*, Roger Pertwee, Chapter 1, pages 3 to 15 details the cannabinoids known to date.

Cannabidiol (CBD) is a major cannabinoid constituent of *Cannabis* species, such as the hemp plant (*Cannabis sativa*). Unlike other cannabinoids, such as THC, cannabidiol does not bind to CB1 or CB2 receptors, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

Cannabidiol administration has been the subject of research in an attempt to provide an alternative treatment for various diseases and disorders which may respond to such treatment.

Whilst literature such as Gong et al. (2019) have described possible synthetic routes to generate C4'-substituted derivatives of CBD, giving a broad range of compounds that could be potentially generated and potentially be tested, there is no provision of any data to suggest the efficacy of such compounds, let alone that any specific compounds would be of particular benefit compared to others in the treatment of a disease.

The present invention has been devised in light of these considerations.

BRIEF SUMMARY OF THE INVENTION

At its most general, the present invention relates to synthetic cannabinoid compounds which are biologically active and hence useful in the treatment of diseases. Such novel compounds may be administered by a wide variety of routes including but not limited to oral, transdermal, buccal, nasal, pulmonary, rectal or ocular. Such compounds may be used for the treatment or prevention of a medical condition such as epilepsy.

In a first aspect of the invention there is provided a compound of formula (I), or a salt thereof, (I)

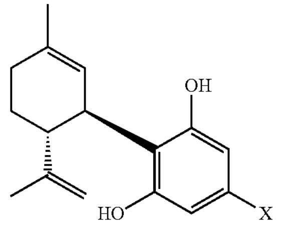

where X is selected from:

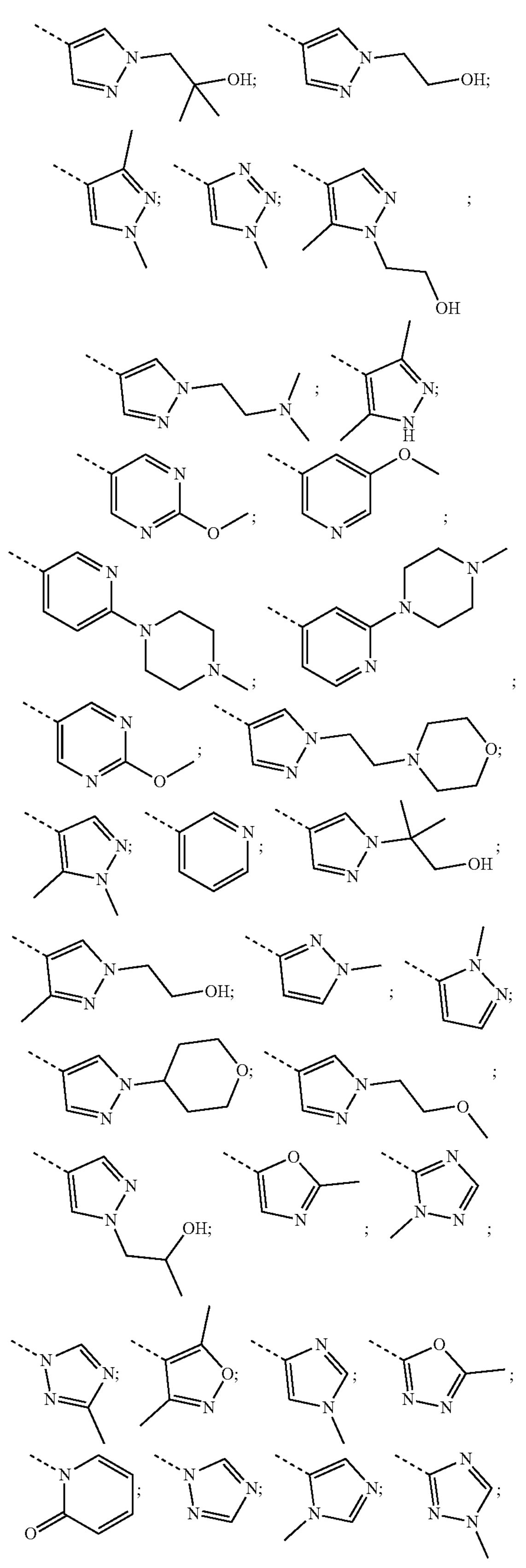

-continued

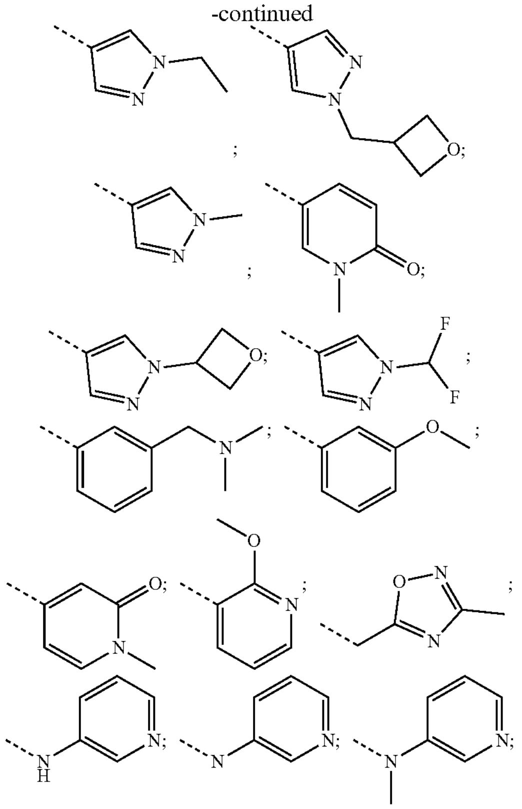

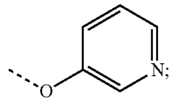 and 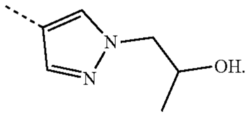

In a second aspect of the invention there is a pharmaceutical composition comprising the compound of the first aspect and one or more additional ingredients selected from carriers, diluents (e.g. oils), excipients, adjuvants, fillers, buffers, binders, disintegrants, preservatives, antioxidants, lubricants, stabilisers, solubilisers, surfactants, masking agents, colouring agents, flavouring agents, and sweetening agents.

Preferably the pharmaceutical composition of the second aspect is in a form selected from a liquid, a solution, a suspension, an emulsion, a syrup, an electuary, a mouthwash, a drop, a tablet, a granule, a powder, a lozenge, a pastille, a capsule, a cachet, a pill, an ampoule, a bolus, a suppository, a pessary, a tincture, a gel, a paste, an ointment, a cream, a lotion, an oil, a foam, a spray, and an aerosol.

In a third aspect of the invention there is provided a compound of the first aspect, or the pharmaceutical composition of the second aspect, for use in a method of treatment.

Preferably, the method of treatment in the third aspect is a method of treatment of epilepsy, generalised seizure or tonic-clonic seizure.

In a fourth aspect of the invention there is provided a compound of the first aspect, or the pharmaceutical composition of the second aspect, for use as a medicament.

Preferably, the medicament of the fourth aspect is a medicament for treating epilepsy, generalised seizure or tonic-clonic seizure.

In a fifth aspect of the invention there is provided a method of treatment comprising administering to a subject in need of treatment a therapeutically effective amount of the compound of the compound of the first aspect or the pharmaceutical composition of the second aspect.

In a sixth aspect of the invention there is provided a method of preparing a compound of formula (I), the method comprising:

(1a) reacting a compound of formula (II) with a compound of formula (III):

(II)

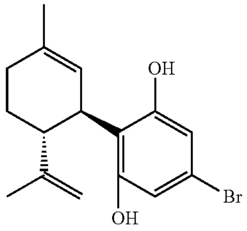

(III)

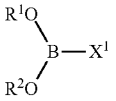

where:

$R^1$ and $R^2$ are OH; or $R^1$ and $R^2$ together form —OC(Me)$_2$C(Me)$_2$O—; and $X^1$ is defined below.

In a seventh aspect of the invention there is provided a method of preparing a compound of formula (I), the method comprising:

(2a) reacting a compound of formula (II) with bis(pinacolato)diboron; and (2b) reacting the product of step (2a) with a compound of formula (IV), (II)

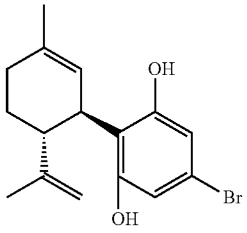

(IV)

$Br—X^2$ where:

$X^2$ is defined below.

In an eight aspect of the invention there is provided an intermediate for use in the preparation of a compound formula (I), wherein the intermediate is a compound of formula (II):

(II)

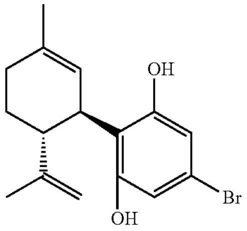

These and other aspects and embodiments of the invention are described in further detail below.

BRIEF SUMMARY OF THE DRAWINGS

Embodiments of the invention are further described hereinafter with reference to the accompanying drawings, in which:

FIG. 1 shows the effect of compound 1 in the mini-MEST test in the mouse.

FIG. 2 shows the effect of compounds 2 and 3 in the mini-MEST test in the mouse.

FIG. 3 shows the effect of compounds 4 and 5 in the mini-MEST test in the mouse.

FIG. 4 shows the effect of compound 12 in the mini-MEST test in the mouse.

FIG. 5 shows the effect of compound 42 in the mini-MEST test in the mouse.

FIG. 6 shows the effect of compound 43 in the mini-MEST test in the mouse.

FIG. 7 shows the effect of compound 1 in the MEST test in the mouse.

FIG. 8 shows the effect of compound 6 in the mini-MEST test in the mouse.

FIG. 9 shows the effect of compound 13 in the mini-MEST test in the mouse.

FIG. 10 shows the effect of compounds 22 and 38 in the mini-MEST test in the mouse.

FIG. 11 shows the effect of compounds 26, 28 and 33 in the mini-MEST test in the mouse.

FIG. 12 shows the effect of compound 46 in the mini-MEST test in the mouse.

FIG. 13 shows the effect of compound 36 in the mini-MEST test in the mouse.

DETAILED DESCRIPTION OF THE INVENTION

The present invention relates to synthetic cannabinoid compounds which are biologically active and hence useful in the treatment of diseases.

Synthetic Cannabinoids

The invention provides a compound of formula (I), (I)

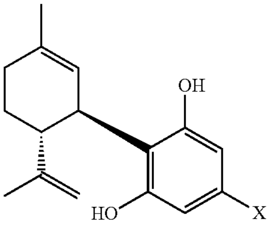

where X is selected from:
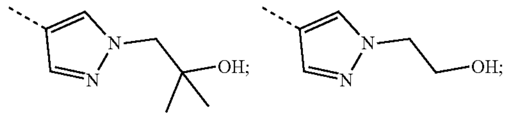
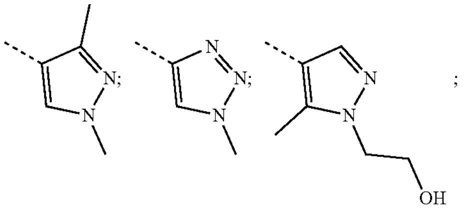
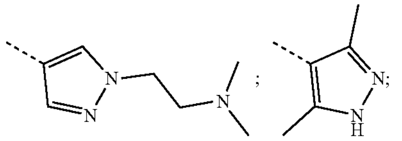
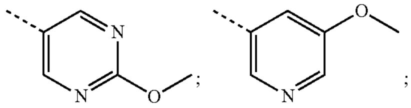
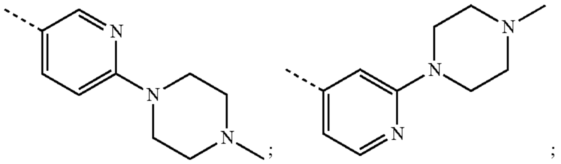
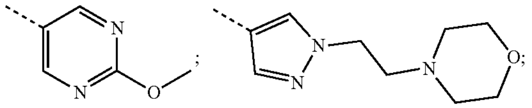
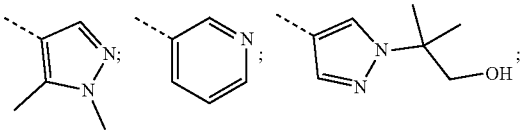
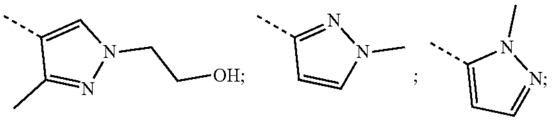
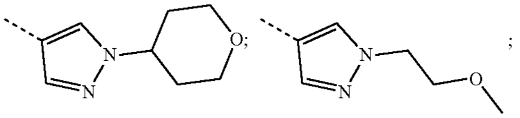
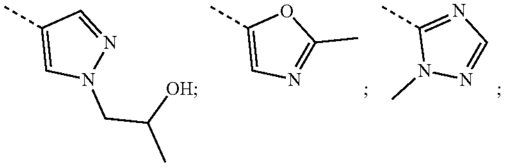
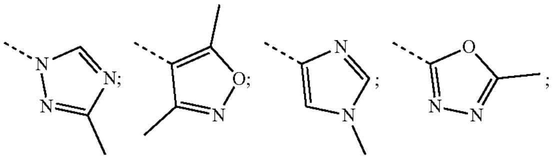
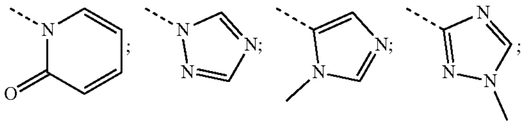
-continued
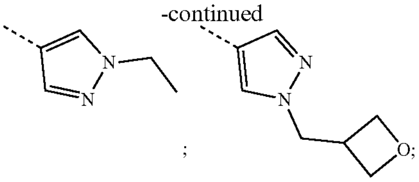
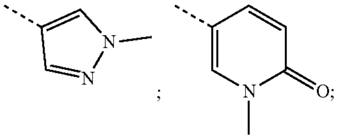
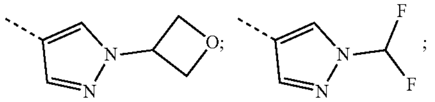
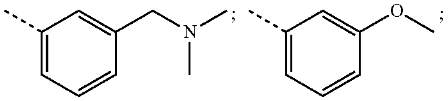
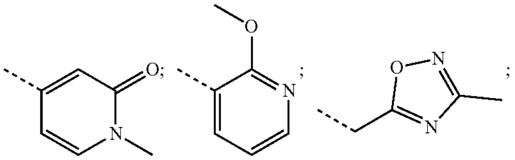
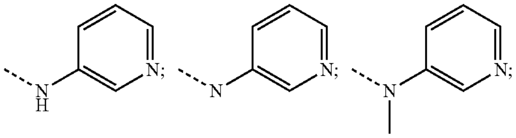
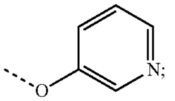
and
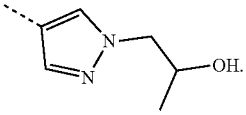
where, the dashed line indicated the connection point with the rest of the molecule.
In a preferred embodiment, X is selected from:
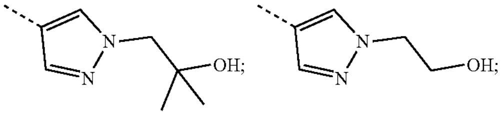
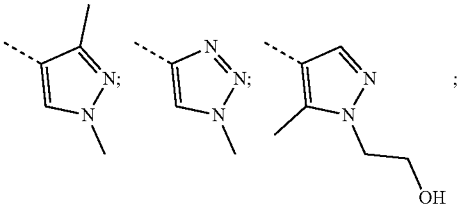
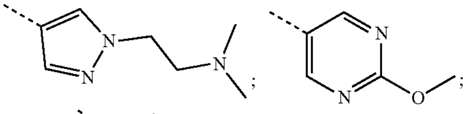
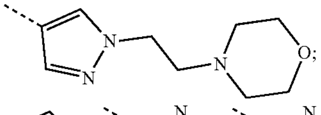
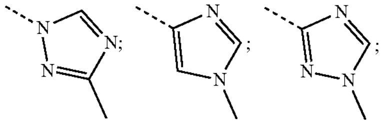

-continued

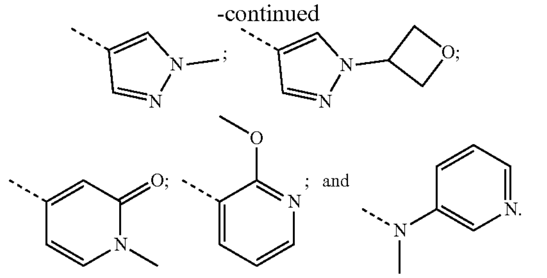

Salts

In some embodiments, the compounds of formula (I) are provided in free base form.

Alternatively, it may be convenient or desirable to prepare, purify, and/or handle a corresponding salt of the compound, for example, a pharmaceutically-acceptable salt. Examples of pharmaceutically acceptable salts are discussed in "Pharmaceutical Salts: Properties, Selection, and Use", 2nd Edition, 2002, Stahl and Wermuth (Eds), Wiley-VCH, Weinheim, Germany.

Accordingly, in some embodiments the compounds of formula (I) are provided as salts, for example in a protonated form together with a suitable counter anion.

Suitable counter anions include both organic and inorganic anions. Example of suitable inorganic anions include those derived from inorganic acids, including chloride (Cr), bromide ($Br^-$), iodide ($I^-$), sulfate ($SO_4^{2-}$), sulfite ($SO_3^{2-}$), nitrate ($NO_3^-$), nitrite ($NO_2^-$), phosphate ($PO_4^{3-}$), and phosphite ($PO_3^{3-}$). Examples of suitable organic anions include 2-acetoxybenzoate, acetate, ascorbate, aspartate, benzoate, camphorsulfonate, cinnamate, citrate, edetate, ethanedisulfonate, ethanesulfonate, formate, fumarate, gluconate, glutamate, glycolate, hydroxymalate, carboxylate, lactate, laurate, lactate, maleate, malate, methanesulfonate, oleate, oxalate, palmitate, phenylacetate, phenylsulfonate, propionate, pyruvate, salicylate, stearate, succinate, sulfanilate, tartarate, toluenesulfonate, and valerate. Examples of suitable polymeric organic anions include those derived from tannic acid and carboxymethyl cellulose.

Alternatively, in some embodiments the compounds of formula (I) are provided as salts, for example in a deprotonated form together with a suitable counter cation.

Suitable counter cations include both organic and inorganic cations. Examples of suitable inorganic cations include alkali metal ions such as $Na^+$ and $K^+$, alkaline earth cations such as $Ca^{2+}$ and $Mg^{2+}$, and other cations such as $Al^{3+}$. Examples of suitable organic cations include the ammonium ion (i.e., $NH_4^+$) and substituted ammonium ions (e.g., $NH_3R^+$, $NH_2R_2^+$, $NHR_3^+$, $NR_4^+$). Examples of substituted ammonium ions include those derived from ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Solvates

In some embodiments, the compounds of formula (I) are provided in desolvated form, for example, in dehydrated form.

Alternatively, it may be convenient or desirable to prepare, purify, and/or handle a corresponding solvate of the compound.

Accordingly, in some embodiments the compounds of formula (I) are provided in the form of a solvate (a complex of solute (e.g., compound, salt of compound) and solvent). Examples of solvates include hydrates, for example, a mono-hydrate, a di-hydrate and a tri-hydrate.

N-Oxides

Where compounds of formula (I) contain an sp 2 nitrogen atom (—N═), for example in a heteroaryl group, it may be convenient to prepare, purify, and/or handle the corresponding N-oxide (—N(→O)═), also denoted as (—$N^+(O^-)$═).

Accordingly, in some embodiments certain compounds of formula (I) are provided in the form of an N-oxide. For example, pyridine may be substituted to give pyridine N-oxide.

Certain Isomers

Certain compounds of formula (I) may exist in one or more particular optical, enantiomeric, diasteriomeric, epimeric, stereoisomeric, tautomeric, or conformational forms, including but not limited to, D- and L-forms; d- and I-forms; (+) and (−) forms; syn- and anti-forms; axial and equatorial forms; boat-, chair-, twistboat-, envelope-, and halfchair-forms; and combinations thereof, hereinafter collectively referred to as "isomers" or "isomeric forms".

Specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference 2-pyridinyl is not to be construed as a reference to its structural isomer, 3-pyridinyl.

The above exclusion does not pertain to tautomeric forms, for example, keto-, enol-, and enolate-forms, as in, for example, the following tautomeric pairs: keto/enol, imine/enamine, amide/imino alcohol, nitroso/oxime, and lactam/lactim.

Included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}C$; and the like.

Unless otherwise specified, a reference to a particular compound includes all such isomeric forms, including (wholly or partially) racemic and other mixtures thereof.

Methods of Synthesis

Methods for the synthesis of compounds of formula (I) are set out in the worked examples. Additional information relevant to the synthesis of synthetic cannabinoids can be found in Gong et al. (2019).

Method 1

The invention provides a first method of preparing a compound of formula (I), the method comprising:

(1a) reacting a compound of formula (II) with a compound of formula (III):

(II)

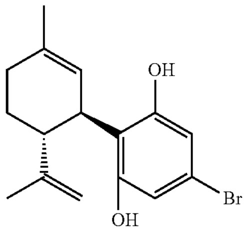

(III)

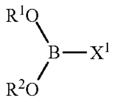

where:

$R^1$ and $R^2$ are OH; or $R^1$ and $R^2$ together form —OC(Me)$_2$C(Me)$_2$O—; and $X^1$ is selected from:

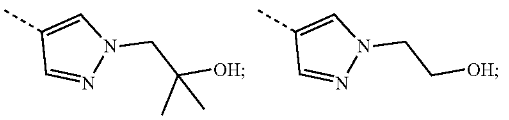

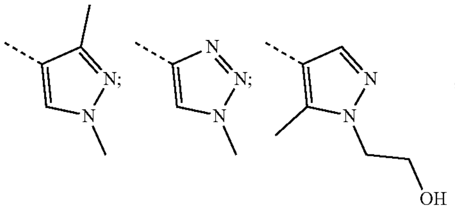

;

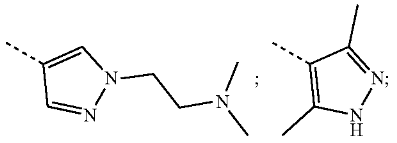

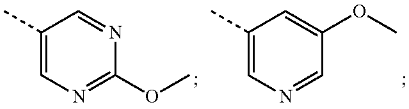

;

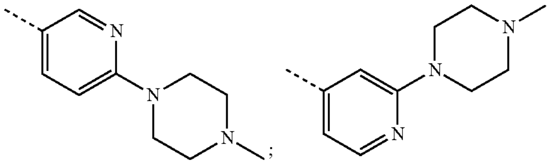

;

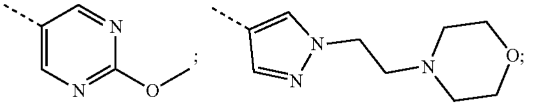

;

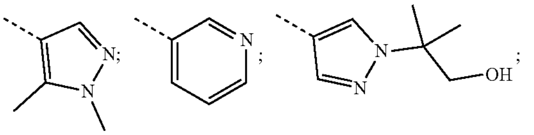

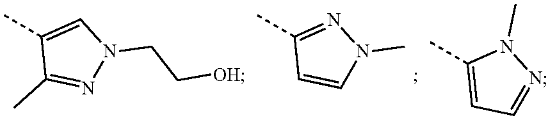

-continued

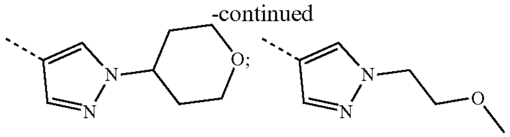

;

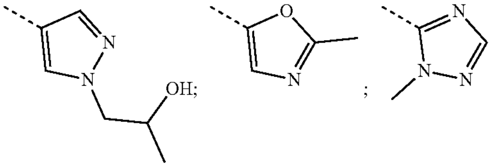

;

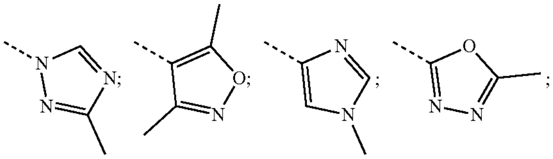

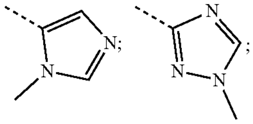

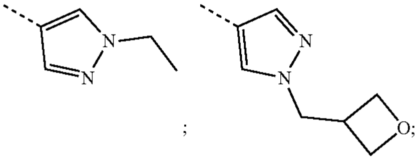

;

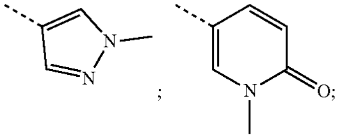

;

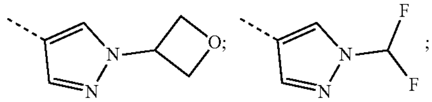

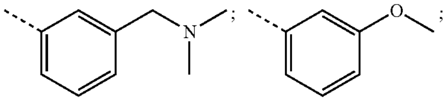

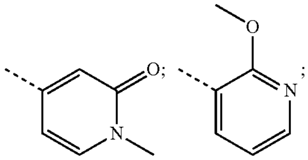

; and

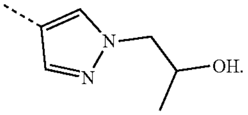

In a preferred embodiment, $R^1$ and $R^2$ together form —OC(Me)$_2$C(Me)$_2$O— (a boronic acid pinacol ester).

Preferably, step (1a) comprises reacting a compound of formula (II) with a compound of formula (III) and a palladium catalyst. Suitable palladium catalysts include Pd(dppf)$Cl_2$ and SPhos-Pd-G2 (Chloro(2-dicyclohexylphosphino-2',6'-dimethoxy-1,1'-biphenyl)[2-(2'-amino-1,1'-biphenyl)] palladium(II)).

Preferably, step (1a) further comprises reacting a compound of formula (II) with a compound of formula (III) and a base. Suitable bases include sodium carbonate ($Na_2CO_3$), caesium carbonate ($Cs_{12}CO_3$)

Typically, step (1a) is carried out in a solvent. Suitable solvents include dioxane, tetrahydrofuran (THF), dimethylformamide (DMF), water Optionally, certain additives may be used in step (1a). Suitable additives include caesium fluoride (CsF).

Step (1a) is typically performed at elevated temperature (above ambient temperature; approximately 20 °C). Methods for providing heat during the reaction are known and include, for example, using a reaction vessel having an external heating jacket or using microwave heating.

Typically, step (1a) comprises reacting a compound of formula (II) with a compound of formula (III) at a temperature of from 60 °C to 140 °C, preferably 80 °C to 140 °C, more preferably 80 °C to 120 °C Step (1a) may be performed for sufficient time to allow a desired quantity of the coupling product to form. Typically, the step (1a) is performed until substantially all of the compound of formula (II) has been consumed.

Typically, the step (1a) comprises reacting a compound of formula (II) with a compound of formula (III) for 1 hour to 24 hours.

Method 2

The invention also provides a second method of preparing a compound of formula (I), the method comprising:

(2a) reacting a compound of formula (II) with bis(pinacolato)diboron; and (2b) reacting the product of step (2a) with a compound of formula (IV), (II)

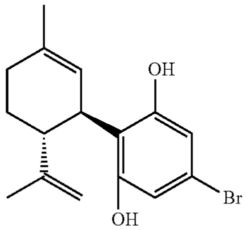

(IV)

$Br—X^2$ where:

$X^2$ is selected from:

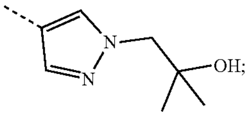
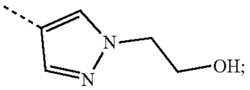
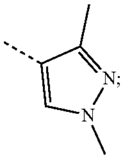
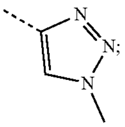
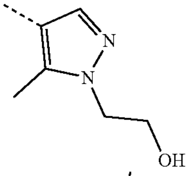
;
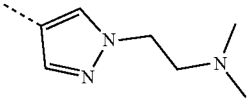
;
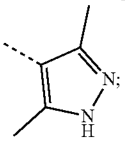
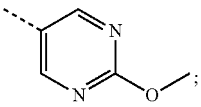
;

-continued

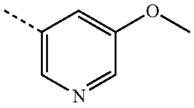
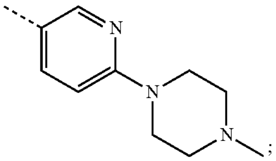
;
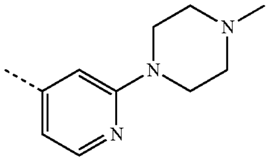
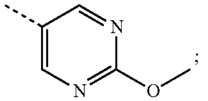
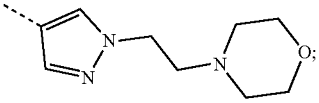
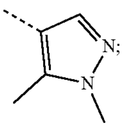
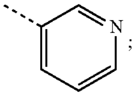
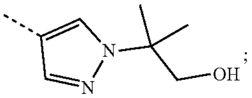
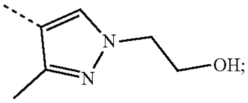
;
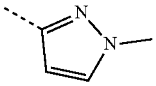
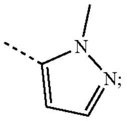
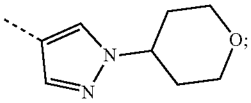
;
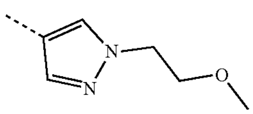
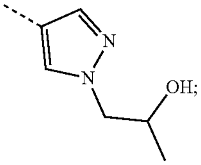
;
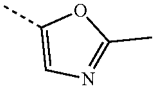
;
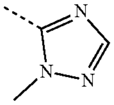
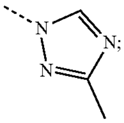
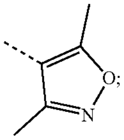
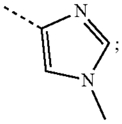
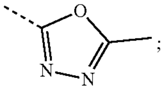
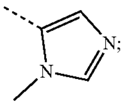
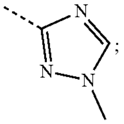
;
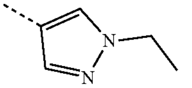
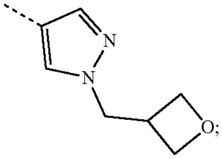
;
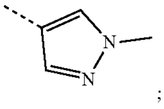
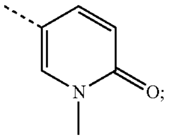
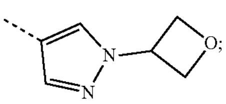
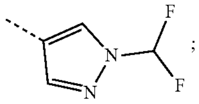
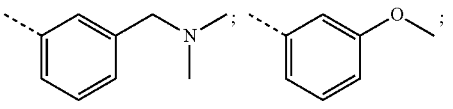

-continued

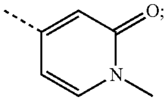
;
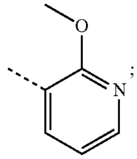
; and
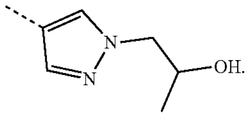

Preferably, step (2a) comprises reacting a compound of formula (II) with bis(pinacolato)diboron and a palladium catalyst. Suitable palladium catalysts include $Pd(dppf)Cl_2$ and SPhos-Pd-G2.

Preferably, step (2a) further comprises reacting a compound of formula (II) with bis(pinacolato)diboron and a base. Suitable bases include potassium acetate.

Typically, step (2a) is carried out in a solvent. Suitable solvents include dioxane and water.

Step (2a) typically comprises reacting a compound of formula (II) with bis(pinacolato)diboron at a temperature of from 60 °C to 140 °C, preferably 80 °C to 140 °C, more preferably 80 °C to 120 °C Step (2a) may be performed for sufficient time to allow a desired quantity of the coupling product to form. Typically, the step (2a) is performed until substantially all of the compound of formula (II) has been consumed.

Typically, the step (2a) comprises reacting a compound of formula (II) with bis(pinacolato)diboron for 1 hour to 24 hours.

Preferably, step (2b) comprises reacting the product of step (2a) with a compound of formula (IV) and a palladium catalyst. Suitable palladium catalysts include $Pd(dppf)Cl_2$ and SPhos-Pd-G2.

Preferably, step (2b) further comprises reacting the product of step (2a) with a compound of formula (IV) and a base. Suitable bases include sodium carbonate ($Na_2CO_3$), caesium carbonate ($Cs_{12}CO_3$)

Typically, step (2b) is carried out in a solvent. Suitable solvents include dioxane and water.

Optionally, certain additives may be used in step (2b). Suitable additives include caesium fluoride (CsF).

Step (2b) typically comprises reacting the product of step (2a) with a compound of formula (IV) at a temperature of from 60 °C to 140 °C, preferably 80 °C to 140 °C, more preferably 80 °C to 120 °C Step (2b) may be performed for sufficient time to allow a desired quantity of the coupling product to form.

Typically, the step (2b) comprises reacting the product of step (2a) with a compound of formula (IV) for 1 hour to 24 hours.

Intermediates

The invention provides an intermediate useful in the preparation of a compound formula (I). The intermediate of the invention is a compound of formula (II):

(II)

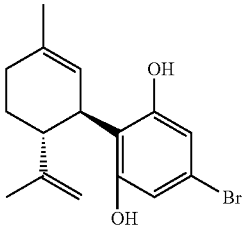

Pharmaceutical Compositions

While it is possible for the compounds of formula (I) to be administered alone, it is preferable to administer a pharmaceutical composition (e.g., a formulation, preparation, or medicament) comprising a compound of formula (I) together with one or more other pharmaceutically acceptable ingredients.

Accordingly, the invention provides a pharmaceutical composition comprising a compound of formula (I), or a salt thereof, together with one or more pharmaceutically acceptable ingredients.

Suitable pharmaceutically acceptable ingredients (e.g. carriers, diluents, excipients, etc.) can be found in standard pharmaceutical texts, for example, Remington: The Science and Practice of Pharmacy, 20th Edition, 2000, pub. Lippincott, Williams & Wilkins; and Handbook of Pharmaceutical Excipients, 2nd edition, 1994.

Examples of suitable pharmaceutically acceptable ingredients include pharmaceutically acceptable carriers, diluents (e.g. oils), excipients, adjuvants, fillers, buffers, binders, disintegrants, preservatives, antioxidants, lubricants, stabilisers, solubilisers, surfactants (e.g., wetting agents), masking agents, colouring agents, flavouring agents, and sweetening agents.

In a preferred embodiment, the pharmaceutical composition comprises, one or more of: an excipient selected among a carrier, an oil, a disintegrant, a lubricant, a stabilizer, a flavouring agent, an antioxidant, a diluent and another pharmaceutically effective compound.

The pharmaceutical composition may be in any suitable form. Examples of suitable forms include liquids, solutions (e.g., aqueous, nonaqueous), suspensions (e.g., aqueous, nonaqueous), emulsions (e.g., oil-in-water, water-in-oil), syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, and aerosols.

In a preferred embodiment, the form of the pharmaceutical composition is selected from a tablet, a capsule, a granule, a powder for inhalation, a sprinkle, an oral solution and a suspension.

Medical Treatment

The inventors have found that the compounds of formula (I) are biologically active. The worked examples demonstrate that compounds of formula (I) display anticonvulsant activity in a mouse model. As such, the compounds of formula (I) and their salts, as well as pharmaceutical compositions comprising the compounds of formula (I) or their salts, will be useful in medical treatment.

Accordingly, the invention provides a compound of formula (I), or a salt thereof, for use in a method of treatment, for example for use in a method of treatment of the human or animal body by therapy (i.e. a method of therapy).

The invention also provides a compound of formula (I), or a salt thereof, for use as a medicament.

The invention also provides a method of treatment comprising administering to a subject in need of treatment a therapeutically effective amount of compound (I), or a salt thereof.

The invention also provides the use of compound (I), or a salt thereof, for the manufacture of a medicament.

Conditions Treated

The inventors have found that the compounds of formula (I) display anticonvulsant activity in a mouse model of generalised seizure. Accordingly, the compounds of formula (I), their salts, as well as pharmaceutical compositions comprising the compounds of formula (I) or their salts, will be useful in the treatment of certain conditions associated with seizure.

Similarly, the compounds of formula (I), their salts, as well as pharmaceutical compositions comprising the compounds of formula (I) or their salts, will be useful as medicaments for treating (and in the manufacture of medicaments for treating) certain conditions associated with seizure.

In a preferred embodiment, the condition associated with seizure is epilepsy.

In one embodiment, the condition associated with seizure is generalised seizure, such as generalised seizure associated with epilepsy.

In one embodiment, the condition associated with seizure is tonic-clonic seizures, such as tonic-clonic seizures associated with epilepsy.

The Subject/Patient

The method of treatment typically comprises administering a compound of formula (I), or a salt thereof, to a subject or patient.

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utan, gibbon), or a human. Furthermore, the subject/patient may be any of its forms of development, for example, an infant or child.

In a preferred embodiment, the subject/patient is a human, more preferably an adult human.

The subject/patient may also be a non-human mammal used in laboratory research, such as a rodent. Rodents include rats, mice, guinea pigs and chinchillas.

Routes of Administration

The method of treatment may comprise administering a compound of formula (I), or a salt thereof, to a subject by any convenient route of administration, whether systemically/peripherally or topically (i.e., at the site of desired action).

The route of administration may be oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection or infusion, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; or by implant of a depot or reservoir, for example, subcutaneously or intramuscularly.

Dosages

The method of treatment typically comprises administering a therapeutically effective amount of a compounds of formula (I), or a salt thereof, to a subject.

Appropriate dosages of the compounds of formula (I), their salts, as well as pharmaceutical compositions comprising the compounds of formula (I) or their salts, can vary from patient to patient. Determining the optimal dosage will generally involve balancing the level of therapeutic benefit against any risk or deleterious side effects. The selected dosage level will depend on a variety of factors including, but not limited to, the activity of the particular compound of formula (I), the route of administration, the time of administration, the rate of excretion of the compound, the duration of the treatment, other active agents, compounds, and/or materials used in combination, the severity of the condition, and the species, sex, age, weight, condition, general health, and prior medical history of the patient. The dosage and route of administration will ultimately be at the discretion of the clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Single or multiple administrations can be carried out with the dose level and pattern being selected by the treating clinician.

Other Aspects and Embodiments

Each and every compatible combination of the embodiments described above is explicitly discloses herein, as if each and every combination was individually and explicitly recited.

Carious further aspects and embodiment of the present invention will be apparent to those skilled in the arti in view of the present disclosure.

Where used, “and/or” is to be taken as a specific disclosure of each of the relevant components or features alone as well as a specific disclosure of the combination of the components or features. For example, “A and/or B” is to be taken as specific disclosure of each of i) A, ii) B, and ii) A and B, just as if each were set out individually.

Unless context dictates otherwise, the descriptions and definitions of the features set out above are not limited to any particular aspect or embodiment of the invention and apply equally to all aspects ad embodiments which are described.

Definitions

The following terms are defined below, to aid understanding of the invention.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the *Cannabis* plant. The phytocannabinoids can be present in an extract including a botanical drug substance, isolated, or reproduced synthetically.

"Syntho-cannabinoids" are those compounds that are not found endogenously or in the *Cannabis* plant. Examples include WIN 55212 and rimonabant.

An "isolated phytocannabinoid" is one which has been extracted from the *Cannabis* plant and purified to such an extent that all the additional components such as secondary and minor cannabinoids and the non-cannabinoid fraction have been removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is a cannabinoid which is present at greater than 95% (w/w) pure. More preferably greater than 96% (w/w) through 97% (w/w) thorough 98% (w/w) to 99% % (w/w) and greater.

Epilepsy is considered to be a disease of the brain defined by any of the following conditions: (1) At least two unprovoked (or reflex) seizures occurring >24 h apart; (2) one unprovoked (or reflex) seizure and a probability of further seizures similar to the general recurrence risk (at least 60%) after two unprovoked seizures, occurring over the next 10 years; (3) diagnosis of an epilepsy syndrome (A practical clinical definition of epilepsy by the International League Against Epilepsy (ILAE), 2014).

The term "generalized seizure" ("generalized onset seizures") refers to seizures conceptualized as originating at some point within the brain and rapidly engaging bilaterally distributed networks (Operational Classification of Seizure Types by the ILAE, 2017.

A "tonic-clonic seizure" occurs in two phases, a tonic phase typically involving muscle stiffening and loss of consciousness, and a clonic phase typically involving rhythmically jerking of the limbs.

The term "pharmaceutically acceptable" pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each ingredient (e.g. carrier, diluent, excipient, etc.) must also be "acceptable" in the sense of being compatible with the other ingredients of the composition.

The term "therapeutically-effective amount" pertains to that amount of a compound, or a material, composition or dosage form comprising a compound, which is effective for producing some desired therapeutic effect, commensurate with a reasonable benefit/risk ratio, when administered in accordance with a desired treatment regimen.

WORKED EXAMPLES

Certain aspects and embodiments of the invention will not be illustrated by way of example and with reference to the figures described above.

Example 1: Synthetic Production Method for CBD Derivatives

This example describes methods of synthesis which were used to produce novel analogues of normal CBD (1-48) which demonstrated pharmacological activity. Schemes 1a and 1b below describe the initial routes to prepare intermediates (1aa, 1ab and 1ba), and Schemes 2a-2r describe the subsequent production of the CBD derivatives 1-48 which were formed via a number of intermediates resulting from either one of Schemes 1a or 1 b, or from specified starting materials (Schemes 2p, 2q, 2r).

Scheme 1a Synthetic route to prepare intermediates 1aa and 1ab

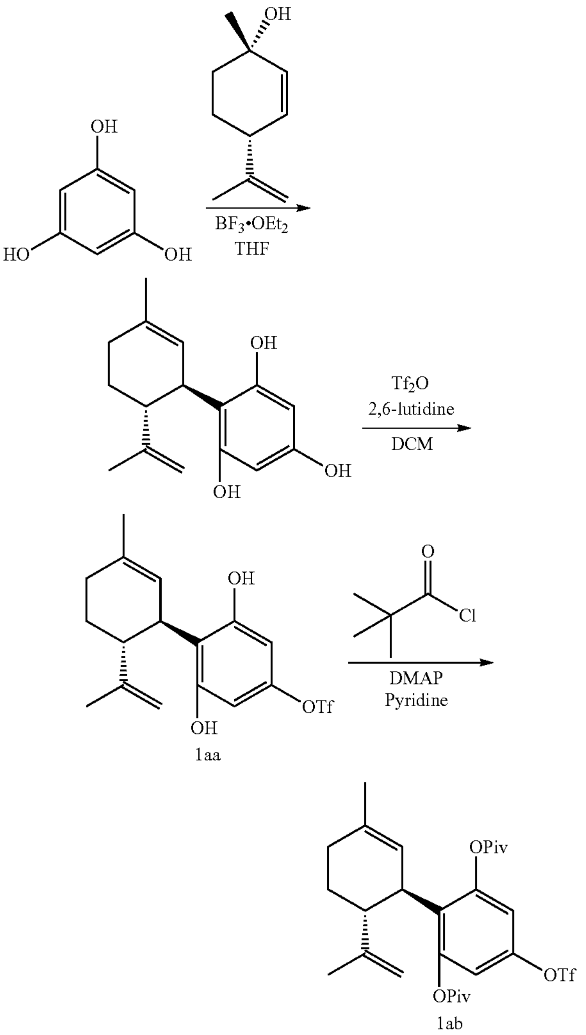

1aa

1ab

The intermediates of Scheme 1a were prepared according to the method of Gong et al. (2019).

Scheme 1b Synthetic route to prepare intermediate 1ba

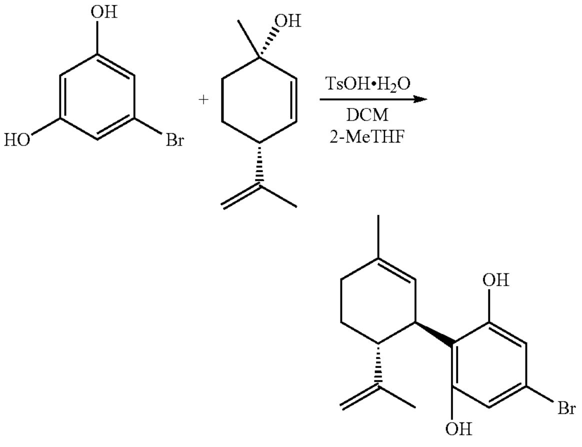

1ba

A solution of 5-bromobenzene-1,3-diol (20.88 g, 110 mmol) and p-toluenesulfonic acid monohydrate (10.51 g, 55.2 mmol) in a mixture of 2-methyltetrahydrofuran (132 mL) and dichloromethane (465 mL) was cooled to 0 °C with an ice/brine bath under nitrogen. (4R)-4-isopropenyl-1-methyl-cyclohex-2-en-1-ol (13 mL, 77.5 mmol) was added and the resulting solution stirred for 5 min. The cooling bath was removed and the colourless solution stirred for 2 hours, warming to 20 °C. The mixture was diluted with dichloromethane (200 mL) and basified to pH 8 by careful addition of saturated aqueous sodium hydrogen carbonate (300 ml). The organic layer was separated and washed with water (50 mL) and saturated brine (50 mL), dried (magnesium sulfate) and concentrated in vacuo to give a colourless gum. This was purified by column chromatography on silica (800 g, Interchim cartridge), eluting with 0-50% diethyl ether in cyclohexane to give the title compound (2.53 g) as a colourless gum. This was repurified by column chromatography on silica gel (40 g, 15 micron Interchim column), eluting with 5-20% diethyl ether in cyclohexane to give the title compound (0.92 g) as well as some impure material.

The initial column also yielded recovered 5-bromobenzene-1,3-diol (8.17 g) as a colourless gum that solidified on standing. This was dissolved in a mixture of 2-methyltetrahydrofuran (55 mL) and dichloromethane (185 mL), treated with (4R)-4-isopropenyl-1-methyl-cyclohex-2-en-1-ol (4.9 mL, 30.3 mmol), cooled to 0 °C with an ice/brine bath under nitrogen. p-Toluenesulfonic acid monohydrate (4.11 g, 21.6 mmol) was added and the resulting solution was stirred for 5 minutes. The cooling bath was removed and the colourless solution was stirred for 2 hours, warming to 20 °C. The mixture was diluted with dichloromethane (100 mL) and basified to pH 8 by careful addition of saturated aqueous sodium hydrogen carbonate (300 mL). The organic layer was separated and washed with water (50 mL) and saturated brine (50 mL), dried (magnesium sulfate) and concentrated in vacuo to give a colourless gum. The residue was purified by column chromatography on silica (40 g Interchim cartridge), eluting with 0-50% diethyl ether in cyclohexane to give the title compound as a colourless gum. This was combined with impure material from the first reaction and purified by column chromatography on silica (40 g Interchim cartridge), eluting with 5-20% diethyl ether in cyclohexane to give the title compound as a colourless gum (2.10 g, 91% LCMS purity).

The total yield of 5-bromo-2-[(1R,6R)-6-isopropenyl-3-methyl-cyclohex-2-en-1-yl]benzene-1,3-diol (1 ba) obtained was 3.02 g (8.5%).

The analytical data of compound 1ba is as follows: $^1$H NMR (400 MHz, DMSO) δ 9.37 (s, 2H), 6.38 (s, 2H), 5.08 (s, 1H), 4.49 (d, J=2.8 Hz, 1H), 4.44 (dd, J=1.6, 2.8 Hz, 1H), 3.86-3.83 (m, 1H), 3.06-2.98 (m, 1H), 2.12-2.07 (m, 1H), 1.96-1.92 (m, 1H), 1.63-1.59 (m, 8H).

Formation of biaryl compounds from aryl bromides (1ba) and triflates (1aa and 1ab) could be achieved using one of a number of sets of conditions, as illustrated by the following schemes 2a-2o. Schemes 2p-2r illustrate synthetic routes of analogues from other specified starting materials.

Scheme 2a

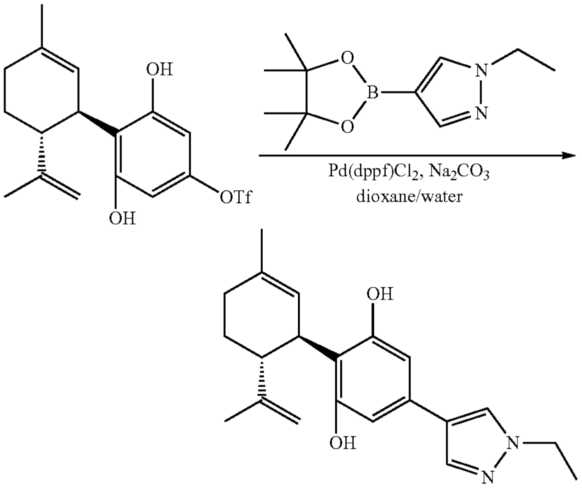

1,1'-Bis(diphenylphosphino)ferrocene]dichloropalladium (II) (19 mg, 0.025 mmol), [3,5-dihydroxy-4-[(1R,6R)-6-isopropenyl-3-methyl-cyclohex-2-en-1-yl]phenyl] trifluoromethanesulfonate (200 mg, 0.510 mmol), 1-ethyl-1H-pyrazole-4-boronic acid pinacol ester (147 mg, 0.663 mmol) and sodium carbonate (216 mg, 2.04 mmol) in 1,4-dioxane (3 mL) and water (1 mL) were heated in a sealed tube at 100 °C for 24 hours. The reaction mixture was cooled to room temperature, filtered through celite and washed with ethyl acetate (20 mL). The filtrate was washed with saturated aqueous sodium hydrogen carbonate solution (10 mL), dried (phase separating paper) and concentrated in vacuo. The residue was purified by reverse phase preparative HPLC to give the compound 34 as an off-white solid (20.5 mg, 12%).

The same method, using the appropriate boronic acid pinacol ester, was used to generate compounds 1 and 5-17.

Scheme 2b

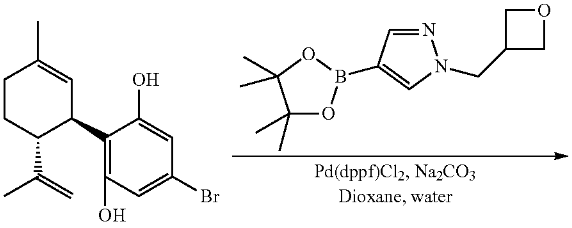

-continued

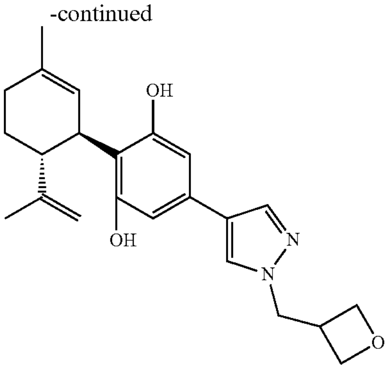

[1,1'-Bis(diphenylphosphino)ferrocene]dichloropalladium(II) (11 mg, 0.015 mmol), 5-bromo-2-[(1R,6R)-6-isopropenyl-3-methyl-cyclohex-2-en-1-yl]benzene-1,3-diol (100 mg, 0.309 mmol), 1-(oxetan-3-ylmethyl)-4-(4,4,5,5-tetramethyl-1,3,2-dioxaborolan-2-yl)pyrazole (106 mg, 0.402 mmol) and sodium carbonate (131 mg, 1.24 mmol) in 1,4-dioxane (2 mL) and water (0.70 mL) were heated in a sealed tube at 100 °C for 24 hours. The reaction mixture was cooled to room temperature, filtered through celite and washed through with ethyl acetate (30 mL). The filtrate was washed with saturated aqueous sodium hydrogen carbonate solution (20 mL), the layers separated and the aqueous extracted with ethyl acetate (20 mL). The combined organic layers were dried (phase separating paper) and concentrated in vacuo. The residue was purified by preparative HPLC to give the compound 35 as an off-white solid (55.9 mg, 48%).

The same method, using the appropriate boronic acid pinacol ester, was used to generate compounds 2, 3, 18-23, 35 and 48.

Scheme 2c

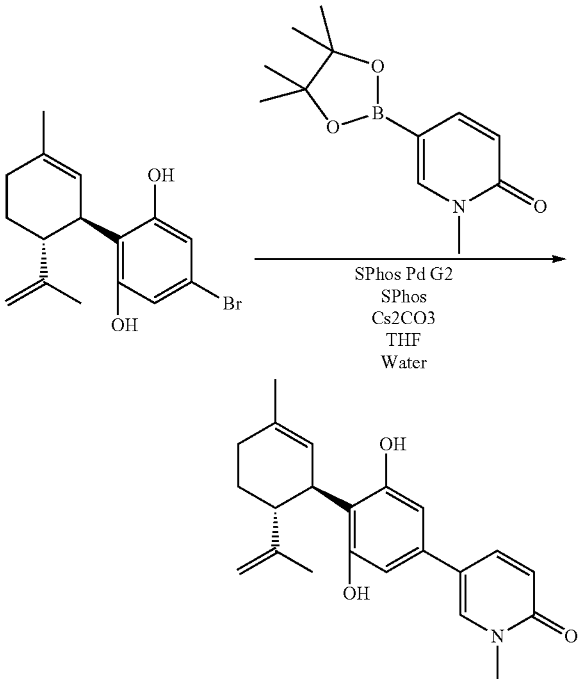

(1'R,2'R)-4-Bromo-5'-methyl-2'-(prop-1-en-2-yl)-1',2',3',4'-tetrahydro-[1,1'-biphenyl]-2,6-diol (119 mg, 0.368 mmol), 1-methyl-5-(4,4,5,5-tetramethyl-1,3,2-dioxaborolan-2-yl)pyridin-2-one (130 mg, 0.553 mmol), cesium carbonate (360 mg, 1.10 mmol) and SPhos (6.0 mg, 0.0146 mmol) in tetrahydrofuran (1.70 mL) and water (170 uL) were degassed with nitrogen, treated with SPhos Pd G2 (6.0 mg, 8.33 μmol) and heated at 80 °C overnight. The reaction mixture was partitioned between diethyl ether (5 mL) and water (5 mL). The layers were separated and the aqueous layer was extracted further with diethyl ether (3×3 mL). The combined organic phases were dried (hydrophobic frit) and concentrated in vacuo. The residue was purified by column chromatography, eluting with 0-100% ethyl acetate in dichloromethane to give the compound 37 as a light brown solid (47 mg, 35%).

The same method, using the appropriate boronic acid pinacol ester, was used to generate compound 41.

Scheme 2d

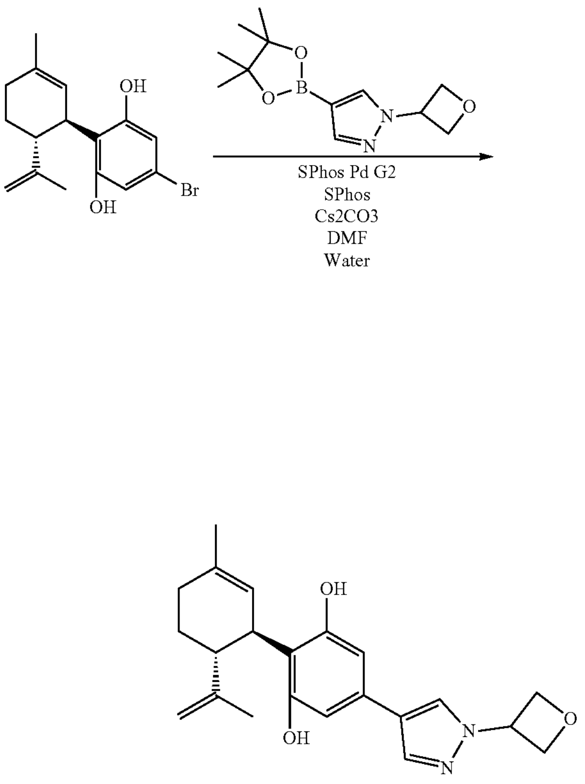

A solution of (1'R,2'R)-4-Bromo-5'-methyl-2'-(prop-1-en-2-yl)-1',2',3',4'-tetrahydro-[1,1'-biphenyl]-2,6-diol (150 mg, 0.464 mmol), 1-(oxetan-3-yl)-4-(4,4,5,5-tetramethyl-1,3,2-dioxaborolan-2-yl)pyrazole (151 mg, 0.603 mmol), cesium carbonate (464 mg, 1.39 mmol) and SPhos Pd G2 (6.7 mg, 9.28 μmol) in N,N-dimethylformamide (4.0 mL), and water (1.0 mL) was degassed with nitrogen and treated with SPhos (7.6 mg, 0.0186 mmol). The reaction mixture was heated in a microwave reactor at 140 °C for 90 minutes then diluted with water (10 mL) and extracted with ethyl acetate (3×25 mL). The organic phases were combined and concentrated in vacuo. The residue was purified by column chromatography, eluting with 0-100% ethyl acetate in cyclohexane followed by reverse phase preparative HPLC to give the compound 38 as an off-white solid (88.5 mg, 51%).

Scheme 2e

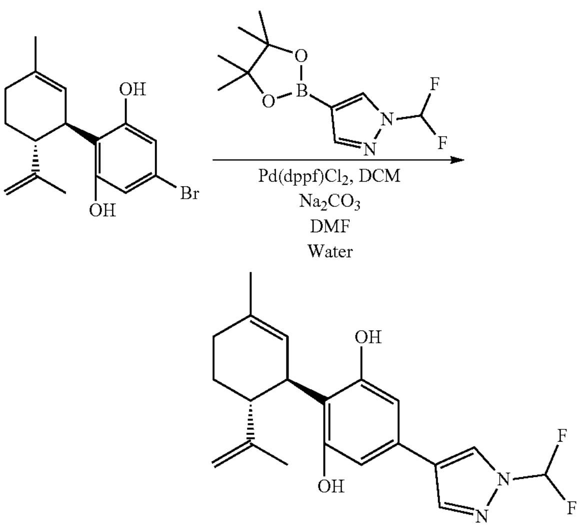

A solution of (1'R,2'R)-4-Bromo-5'-methyl-2'-(prop-1-en-2-yl)-1',2',3',4'-tetrahydro-[1,1'-biphenyl]-2,6-diol (150 mg, 0.464 mmol), 1-(difluoromethyl)-4-(4,4,5,5-tetramethyl-1,3,2-dioxaborolan-2-yl)pyrazole (147 mg, 0.603 mmol) and sodium carbonate (148 mg, 1.39 mmol) in N,N-dimethylformamide (4.0 mL), and water (1.0 mL) was degassed with nitrogen and treated with [1,1-bis(diphenylphosphino)ferrocene]dichloropalladium(II) complex with dichloromethane (19 mg, 0.023 mmol). The reaction mixture was heated in a microwave reactor at 140 °C for 90 minutes then diluted with water (10 mL) and extracted with ethyl acetate (3×25 mL). The organic phases were combined and concentrated in vacuo. The residue was purified by column chromatography, eluting with 0-100% ethyl acetate in cyclohexane followed by reverse phase preparative HPLC to give the compound 39 as an off-white solid (36.9 mg, 24%).

Scheme 2f

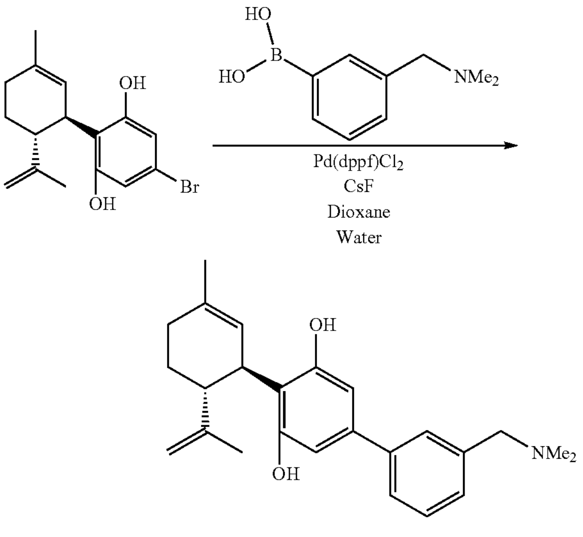

A solution of (1'R,2'R)-4-bromo-5'-methyl-2'-(prop-1-en-2-yl)-1',2',3',4'-tetrahydro-[1,1'-biphenyl]-2,6-diol (80 mg, 0.248 mmol), [3-[(dimethylamino)methyl]phenyl]boronic acid (44 mg, 0.248 mmol) and cesium fluoride (113 mg, 0.743 mmol) in 1,4-dioxane (2.00 mL) and water (1.00 mL) was degassed with nitrogen and treated with [1,1'-bis(diphenylphosphino)-ferrocene]dichloropalladium(II) (9.2 mg, 0.012 mmol). The reaction mixture was heated at 90 °C for 60 minutes then diluted with ethyl acetate (25 mL), washed with water (25 mL), dried (phase separating filter paper) and concentrated in vacuo. The residue was purified by column chromatography, eluting with 0-50% ethyl acetate/ethanol/NH3 75:25:1 in cyclohexane to give the compound 40 as a beige solid (32.6 mg, 32%).

The same method, using the appropriate boronic acid pinacol ester, was used to generate compound 43.

Scheme 2g

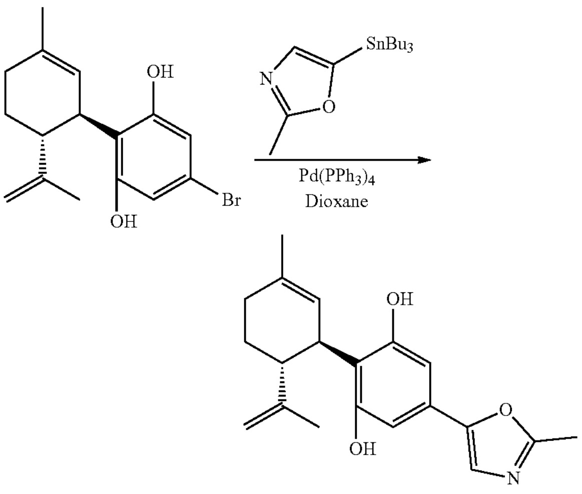

(1'R,2'R)-4-Bromo-5'-methyl-2'-(prop-1-en-2-yl)-1',2',3',4'-tetrahydro-[1,1'-biphenyl]-2,6-diol (100 mg, 0.254 mmol) was dissolved in dry 1,4-dioxane (3 mL) and degassed with nitrogen. 2-Methyl-5-(tributylstannyl)oxazole (104 mg, 0.279 mmol) and tetrakis(triphenylphosphine)-palladium(0) (29 mg, 0.025 mmol) were added and the reaction mixture was heated at 100 °C overnight. The reaction mixture was diluted with ethyl acetate (20 mL), filtered through celite, washed with water (10 mL) and 1M aqueous potassium fluoride solution (3×20 mL). The organic layer was separated, dried (magnesium sulfate) and concentrated in vacuo. The residue was purified by column chromatography on silica, eluting with 0-100% diethyl ether in cyclohexane followed by reverse phase preparative HPLC to give the compound 24 as an off-white solid (19.4 mg, 23%).

Scheme 2h

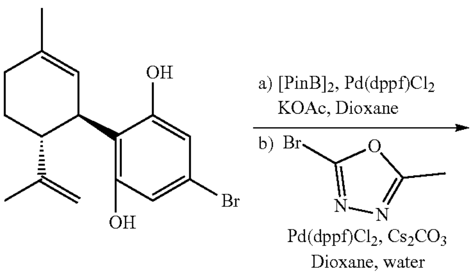

-continued

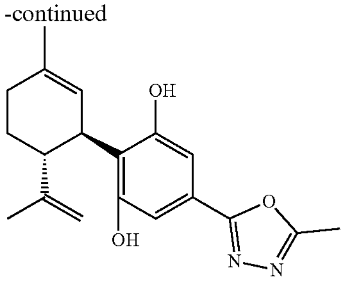

(1'R,2'R)-4-Bromo-5'-methyl-2'-(prop-1-en-2-yl)-1',2',3',4'-tetrahydro-[1,1'-biphenyl]-2,6-diol (100 mg, 0.309 mmol), bis(pinocolato)diboron (94 mg, 0.371 mmol) and potassium acetate (61 mg, 0.619 mmol) in dioxane (4.0 mL) were degassed with nitrogen, treated with [1,1'-bis(diphenylphosphino)ferrocene]dichloropalladium(II) (11 mg, 0.015 mmol) and heated at 100 °C overnight. The reaction mixture was cooled to room temperature and treated with 2-bromo-5-methyl-1,3,4-oxadiazole (53 mg, 0.325 mmol), cesium carbonate (202 mg, 0.619 mmol) and [1,1-bis(diphenylphosphino)ferrocene]dichloropalladium(II) (11 mg, 0.015 mmol). The reaction mixture was heated at 100 °C for 5 hours. Further 2-bromo-5-methyl-1,3,4-oxadiazole (53 mg, 0.325 mmol) and [1,1-bis(diphenylphosphino)ferrocene]dichloropalladium(II) (11 mg, 0.015 mmol) were added and the reaction mixture was heated at 100 °C overnight. The mixture was diluted with ethyl acetate (3 mL) and washed with water (4 mL) and brine (2 mL). The aqueous phases were combined, extracted with ethyl acetate (2×3 mL) and the combined organic phases were washed with water (4 mL) and brine (2 mL), dried (hydrophobic frit) and concentrated in vacuo. The residue was purified by reverse phase preparative HPLC followed by column chromatography on silica, eluting with 0-10% methanol in dichloromethane, to give the compound 29 as an off-white solid (30.3 mg, 30%).

The same method, using the appropriate boronic acid pinacol ester, was used to generate compounds 4.

Scheme 2i

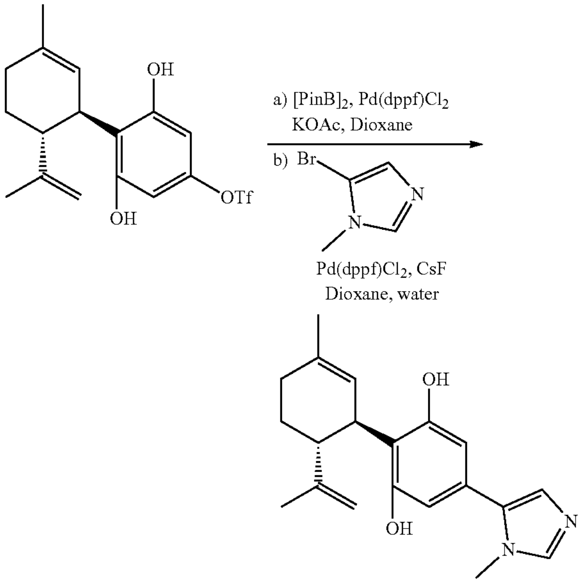

(1'R,2'R)-2,6-Dihydroxy-5'-methyl-2'-(prop-1-en-2-yl)-1',2',3',4'-tetrahydro-[1,1'-biphenyl]-4-yl trifluoromethanesulfonate (200 mg, 0.510 mmol), bis(pinacolato)diboron (194 mg, 0.765 mmol), potassium acetate (200 mg, 2.04 mmol) and [1,1'-bis(diphenylphosphino)ferrocene]dichloropalladium(II) (19 mg, 0.025 mmol) in 1,4-dioxane (5 mL) were heated in a sealed tube at 100 °C for 24 hours. The reaction mixture was cooled to room temperature and water (2 mL), cesium fluoride (310 mg, 2.04 mmol), 5-bromo-1-methyl-1H-imidazole (107 mg, 0.663 mmol) and [1,1-bis(diphenylphosphino)ferrocene]-dichloropalladium(II) (19 mg, 0.025 mmol) were added. The mixture was heated in a sealed tube at 100 °C for 24 hours. The reaction mixture was cooled to room temperature, filtered through celite and washed through with ethyl acetate (30 mL). The filtrate was washed with saturated aqueous sodium hydrogen carbonate solution (20 mL). The layers were separated and aqueous extracted with ethyl acetate (2×20 mL). The combined organic layers were dried (phase separating paper) and concentrated in vacuo. The residue was purified by reverse phase preparative HPLC to give the compound 32 as an off-white solid (0.5 equivalent formate salt) (4.76 mg, 3%).

The same method, using the appropriate boronic acid pinacol ester, was used to generate compound 25.

Scheme 2j

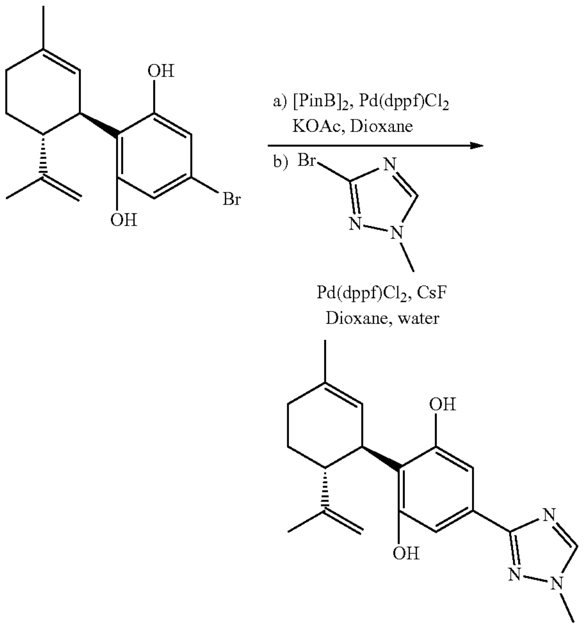

5-Bromo-2-[(1R,6R)-6-isopropenyl-3-methyl-cyclohex-2-en-1-yl]benzene-1,3-diol (100 mg, 0.309 mmol), bis(pinacolato)diboron (118 mg, 0.464 mmol), potassium acetate (121 mg, 1.24 mmol) and [1,1'-bis(diphenylphosphino)ferrocene]dichloropalladium(II) (11 mg, 0.0155 mmol) in 1,4-dioxane (3 mL) were heated in a sealed tube at 100 °C for 24 hours. The reaction mixture was cooled to room temperature and water (1 mL), cesium fluoride (188 mg, 1.24 mmol), 3-bromo-1-methyl-1H-1,2,4-triazole (65 mg, 0.402 mmol) and [1,1'-bis(diphenylphosphino)ferrocene]dichloropalladium(II) (11 mg, 0.015 mmol) were added. The reaction mixture was heated in a sealed tube at 100 °C for 24 hours. The mixture was cooled to room temperature, 3-bromo-1-methyl-1H-1,2,4-triazole (65 mg, 0.402 mmol), sodium carbonate (131 mg, 1.24 mmol) and [1,1-bis(diphenylphosphino)ferrocene]-dichloropalladium(II) (11 mg, 0.015 mmol) were added and heated in a sealed tube at 100 °C for 4 hours. The reaction mixture was cooled to room temperature and filtered through celite and washed through with ethyl acetate (30 mL). The filtrate was washed with saturated aqueous sodium hydrogen carbonate solution (20 mL). The layers were separated and aqueous extracted with ethyl acetate (2×20 mL). The combined organics were dried (phase separating paper) and concentrated in vacuo. The residue was purified by reverse phase preparative HPLC to give the compound 33 as an off-white solid (6.96 mg, 7%).

The same method, using the appropriate boronic acid pinacol ester, was used to generate compounds 42.

Scheme 2k

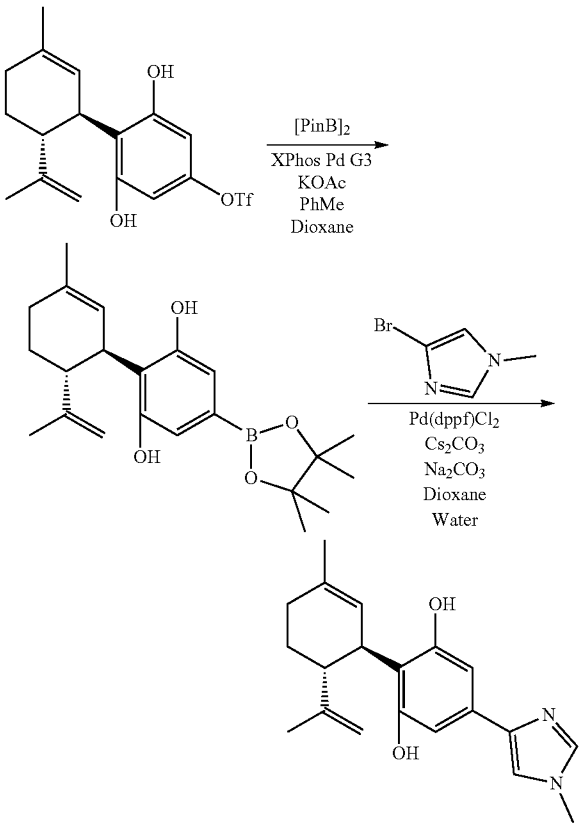

(1'R,2'R)-2,6-Dihydroxy-5'-methyl-2'-(prop-1-en-2-yl)-1',2',3',4'-tetrahydro-[1,1'-biphenyl]-4-yl trifluoromethanesulfonate (975 mg, 2.16 mmol) was dissolved in toluene (10 mL) and dry 1,4-dioxane (6.0 mL) and degassed with nitrogen. Bis(pinacolato)diboron (604 mg, 2.38 mmol), potassium acetate (636 mg, 6.49 mmol) and XPhos Pd G3 (37 mg, 0.043 mmol) were added and the mixture was stirred at 95 °C overnight. The reaction was poured into water (10 mL) and extracted with diethyl ether (3×10 mL). The combined organic phases were dried (hydrophobic frit) and concentrated in vacuo. The residue was purified by column chromatography on silica, eluting with 0-20% diethyl ether in cyclohexane to give the title compound as a colourless gum (172 mg, 13%, NMR showed contamination with 40% pinacol).

A solution of (1'R,2'R)-5'-methyl-2'-(prop-1-en-2-yl)-4-(4,4,5,5-tetramethyl-1,3,2-dioxaborolan-2-yl)-1',2',3',4'-tetrahydro-[1,1'-biphenyl]-2,6-diol (172 mg, 60% purity, 0.279 mmol), 4-bromo-1-methyl-1H-imidazole (0.028 mL, 0.279 mmol) and sodium carbonate (118 mg, 1.11 mmol) in 1,4-dioxane (2.0 mL) and water (0.50 mL) was degassed with nitrogen and treated with [1,1-bis(diphenylphosphino)ferrocene]dichloropalladium(II) (10 mg, 0.014 mmol). The reaction mixture was heated at 100 °C overnight then treated with further 4-bromo-1-methyl-1H-imidazole (0.056 mL, 0.558 mmol), cesium carbonate (91 mg, 0.279 mmol) and [1,1'-bis(diphenylphosphino)ferrocene]dichloropalladium (II) (10 mg, 0.0139 mmol). The reaction mixture was heated at 100 °C for a further 6 hours then partitioned between ethyl acetate (20 mL) and water (20 mL). The aqueous phase was extracted with ethyl acetate (2×20 mL). The combined organic phases were washed with brine (20 mL), dried (magnesium sulfate) and concentrated in vacuo. The residue was purified by reverse phase preparative HPLC to give the compound 28 as an off-white solid (7.1 mg, 7.9%).

Scheme 2l

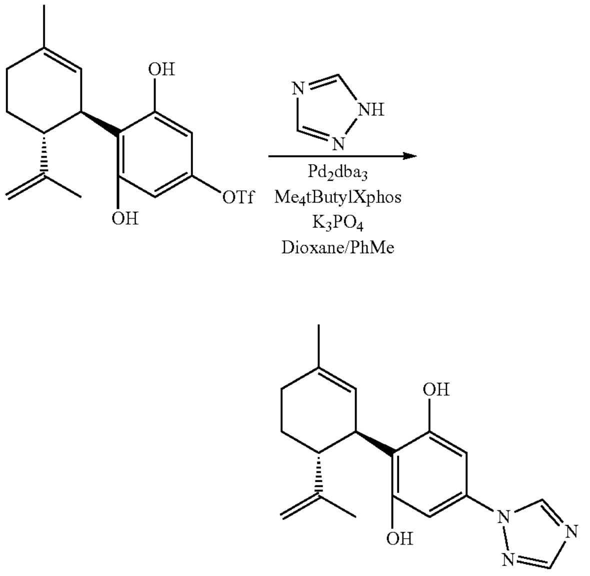

A degassed solution of tris(dibenzylideneacetone)dipalladium(0) (18 mg, 0.019 mmol) and Me4tButylXphos (22 mg, 0.046 mmol) in toluene (2.50 mL) and 1,4-dioxane (0.50 mL) was heated to 120 °C and stirred for 10 minutes. After cooling to room temperature (1'R,2'R)-2,6-Dihydroxy-5'-methyl-2'-(prop-1-en-2-yl)-1',2',3',4'-tetrahydro-[1,1'-biphenyl]-4-yl trifluoromethanesulfonate (150 mg, 0.382 mmol), potassium phosphate tribasic (243 mg, 1.15 mmol) and 1,2,4-triazole (26 mg, 0.382 mmol) were added and the mixture was degassed, heated to 120 °C and stirred for 4 hours. The reaction mixture was diluted with ethyl acetate (30 ml), washed with water (20 mL) and brine (20 mL), dried (magnesium sulfate) and concentrated in vacuo. The residue was purified by column chromatography on silica, eluting with 0-100% ethyl acetate in cyclohexane) followed by reverse phase preparative HPLC to give the compound 31 as an off-white solid (1 equivalent trifluoroacetate salt) (8.75, mg, 7.4%).

The same method, using the appropriate boronic acid pinacol ester, was used to generate compound 26.

Scheme 2m

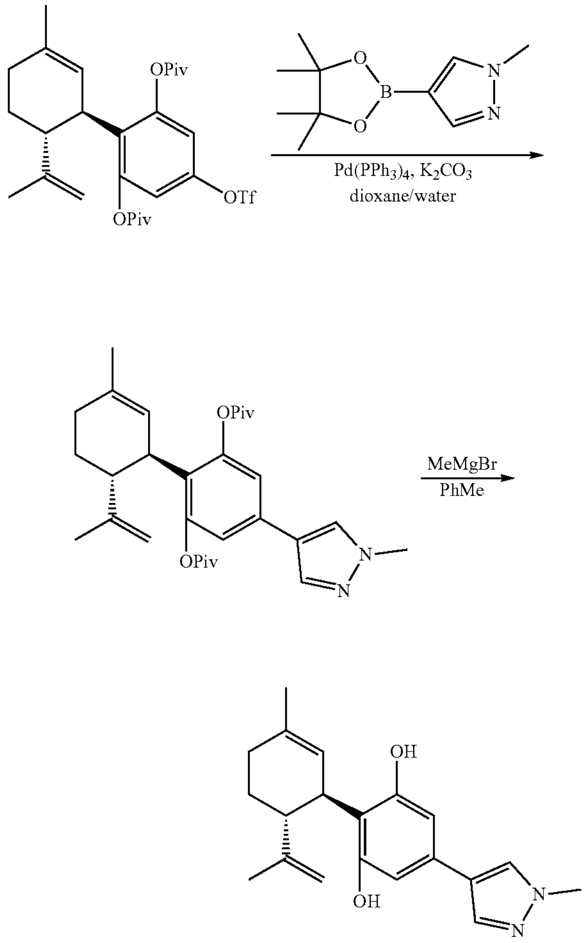

(1'R,2'R)-5'-Methyl-2'-(prop-1-en-2-yl)-4-(((trifluoromethypsulfonyl)oxy)-1',2',3',4'-tetrahydro-[1,1'-biphenyl]-2,6-diylbis(2,2-dimethylpropanoate) (200 mg, 0.357 mmol), 1-methyl-4-(4,4,5,5-tetramethyl-1,3,2-dioxaborolan-2-yl)-1H-pyrazole and potassium carbonate (99 mg, 0.713 mmol) in dioxane (5.0 mL) and water (1.0 mL) were treated with tetrakis(triphemnylphosphine)palladium (0) (21 mg, 0.018 mmol). The mixture was heated in a microwave reactor at 140 °C for 30 minutes and concentrated in vacuo. The residue was dissolved in dichloromethane (20 mL) and washed with water (5 mL). The organic layer was dried (hydrophobic frit) and concentrated in vacuo to give crude (1'R,2'R)-5'-methyl-4-(1-methyl-1H-pyrazol-4-yl)-2'-(prop-1-en-2-yl)-1',2',3',4'-tetrahydro-[1,1'-biphenyl]-2,6-diyl bis (2,2-dimethylpropanoate) (149 mg). This was dissolved in toluene (5.0 mL) and treated with methylmagnesium bromide (3M in tetrahydrofuran, 0.57 mL, 1.71 mmol). The reaction mixture was heated to 110 °C for 7 hours. After cooling to room temperature the mixture was quenched with saturated ammonium chloride solution (2 mL). The mixture was extracted with dichloromethane (2×25 mL). The combined organic phases were dried (hydrophobic frit) and concentrated in vacuo. The residue was purified by reverse phase preparative HPLC to give the compound 36 as a colourless solid (21 mg, 18%).

The same method using the appropriate boronic acid pinacol ester, was used to generate compounds 27.

Scheme 2n

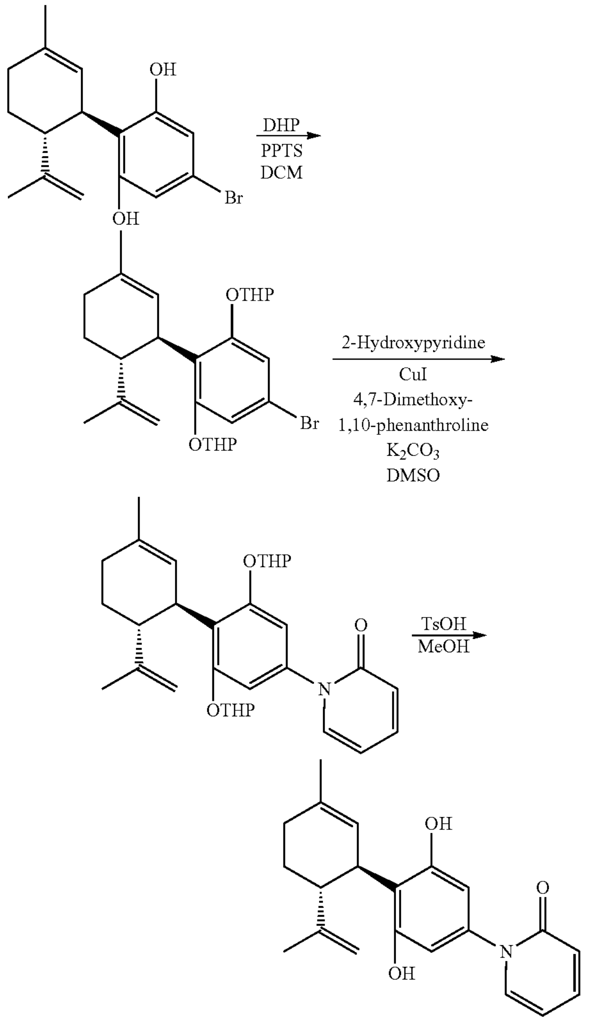

A solution of 5-bromo-2-[(1R,6R)-6-isopropenyl-3-methyl-cyclohex-2-en-1-yl]benzene-1,3-dial (300 mg, 0.928 mmol) and pyridinium p-toluenesulfonate (47 mg, 0.186 mmol) in dichloromethane (6.0 mL) was treated with 3,4-dihydro-2H-pyran (0.25 mL, 2.78 mmol) and stirred at room temperature overnight. The reaction mixture was diluted with ethyl acetate (50 mL) and the organic layer was washed with saturated aqueous sodium hydrogen carbonate solution (20 mL), water (20 mL) and brine (20 mL), dried (magnesium sulfate) and concentrated in vacuo to give crude 2,2'-(((1'R,2'R)-4-bromo-5'-methyl-2'-(prop-1-en-2-yl)-1',2',3',4'-tetrahydro-[1,1'-biphenyl]-2,6-diyl)bis(oxy))bis(tetrahydro-2H-pyran) as a yellow oil (391 mg, 86% crude yield).

A portion of this material (50 mg, 0.102 mmol) was dissolved in DMSO (0.5 mL) and treated with 2-hydroxypyridine (12 mg, 0.122 mmol), potassium carbonate (42 mg, 0.305 mmol), 4,7-dimethoxy-1,10-phenanthroline (4.9 mg, 0.0203 mmol) and copper(I) iodide (1.9 mg, 0.010 mmol). The reaction mixture was heated in a microwave reactor reaction at 120 °C and stirred for 5 hours then treated with further 2-hydroxypyridine (12 mg, 0.122 mmol) and copper (I) iodide (1.9 mg, 0.010 mmol) and heated at 150 °C for a further 2 hours. The reaction mixture was diluted with ethyl acetate (20 mL) and washed with water (10 mL) and brine (10 mL). The organic layer was dried (magnesium sulfate) and concentrated to give crude 1-((1'R,2'R)-5'-methyl-2'-(prop-1-en-2-yl)-2,6-bis((tetrahydro-2H-pyran-2-yl)oxy)-1',2',3',4'-tetrahydro-[1,1'-biphenyl]-4-yl)pyridin-2(1H)-one as a brown oil (35 mg). Without further purification this was dissolved in methanol (1.0 mL), treated with p-toluenesulfonic acid monohydrate (2.4 mg, 0.013 mmol) and stirred at room temperature overnight. The reaction mixture was diluted with ethyl acetate (20 mL), washed with saturated aqueous sodium hydrogen carbonate solution (10 mL), water (10 mL) and brine (10 mL). The organic layer was dried (magnesium sulfate) and concentrated in vacuo. The residue was purified by reverse phase preparative HPLC to give the compound 30 as an off-white solid (2.0 mg, 5.8%).

Scheme 2o

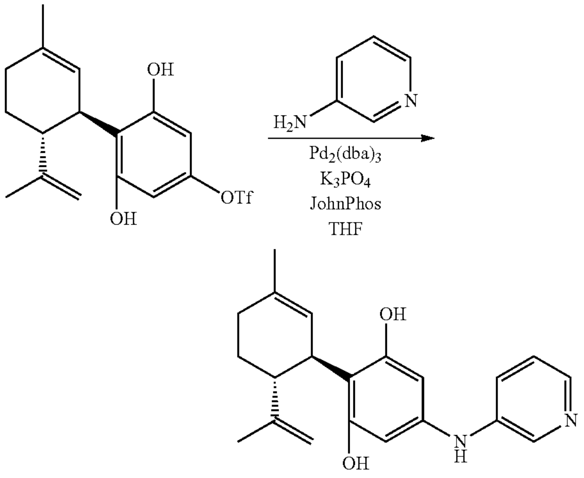

A degassed solution of (1'R,2'R)-2,6-dihydroxy-5'-methyl-2'-(prop-1-en-2-yl)-1',2',3',4'-tetrahydro-[1,1'-biphenyl]-4-yl trifluoromethanesulfonate (200 mg, 0.510 mmol), 3-aminopyridine (58 mg, 0.612 mmol), JohnPhos (7.6 mg, 0.025 mmol) and potassium phosphate tribasic (325 mg, 1.53 mmol) in tetrahydrofuran (2.50 mL) was treated with tris(dibenzylideneacetone)dipalladium(0) (2.3 mg, 2.55 µmol). The mixture was degassed and heated at 85 °C for 3 hours. The reaction mixture was diluted with ethyl acetate (30 mL) and washed with water (20 mL) and brine (20 mL), dried (magnesium sulfate) and concentrated in vacuo. The residue was purified by column chromatography on silica, eluting with 0-60% 3:1 ethyl acetate/ethanol in cyclohexane to give the compound 45 as a brown solid (44 mg, 26%).

The same method, using the appropriate boronic acid pinacol ester, was used to generate compound 46.

Scheme 2p

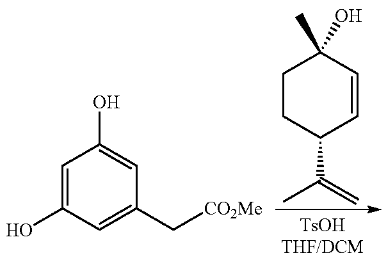

-continued

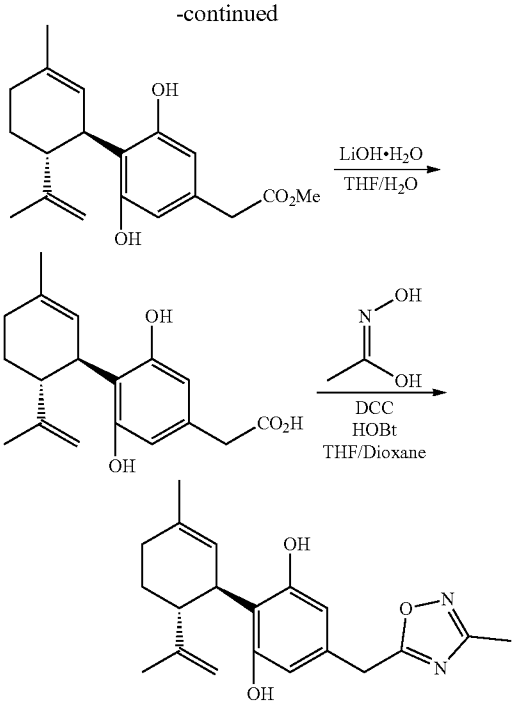

Methyl 3,5-dihydroxyphenylacetate (5.25 g, 28.8 mmol) was dissolved in tetrahydrofuran (20 mL) and diluted with dichloromethane (80 mL). p-Toluenesulfonic acid monohydrate (548 mg, 2.88 mmol) was added and the mixture cooled to 4 °C (1S,4R)-4-isopropenyl-1-methyl-cyclohex-2-en-1-ol (5.8 mL, 36.0 mmol) was added in one portion and the mixture was warmed to room temperature and stirred overnight. Saturated aqueous sodium hydrogen carbonate solution (20 mL) was added and the mixture stirred for 10 minutes and diluted with water (40 mL). The layers were separated and the aqueous layer was extracted with dichloromethane (3×40 mL). The combined organic layers were dried (hydrophobic frit) and concentrated in vacuo. The residue was purified by column chromatography on silica, eluting with 0-70% diethyl ether in cyclohexane to give 75% pure methyl 2-((1'R,21R)-2,6-dihydroxy-5'-methyl-2'-(prop-1-en-2-yl)-1',2',3',4'-tetrahydro-[1,1'-biphenyl]-4-yl) acetate (3.2 g, 20%) as a yellow oil.

Methyl 2-[3,5-dihydroxy-4-[(1R,6R)-6-isopropenyl-3-methyl-cyclohex-2-en-1-yl]phenyl]acetate (75%, 3.13 g, 7.42 mmol) was dissolved in tetrahydrofuran (72 mL). Water (12.00 mL) was added followed by lithium hydroxide monohydrate (996 mg, 23.7 mmol) and the mixture was stirred at room temperature for 2 hours. The mixture was acidified to pH 5 with 2M HCl (10.5 mL). Water (75 mL) and EtOAc (75 mL) were added and the organic layer was separated and washed with 1:1 brine:water (60 mL). The organic phase was dried (hydrophobic frit) and concentrated in vacuo. The aqueous phases were extracted further with EtOAc (60 mL). The organic phase was dried (hydrophobic frit) and the solvent was concentrated in vacuo. The residues were combined and purified by column chromatography on silica, eluting with 50-100% diethyl ether in cyclohexane to give 2-((1'R,2'R)-2,6-dihydroxy-5'-methyl-2'-(prop-1-en-2-yl)-1',2',3',4'-tetrahydro-[1,1'-biphenyl]-4-yl)acetic acid (2.0 g, 91%) as a yellow oil.

2-((1' R,2'R)-2,6-Dihydroxy-5'-methyl-2'-(prop-1-en-2-yl)-1',2',3',4'-tetrahydro-[1,1'-biphenyl]-4-yl)acetic acid (100 mg, 0.331 mmol) was dissolved in tetrahydrofuran (4 mL) and cooled to 0 °C. N,N'-Dicyclohexylcarbodiimide (75 mg, 0.364 mmol) and 1-hydroxybenzotriazole (49 mg, 0.364 mmol) were added and the mixture was stirred at 0 °C for 3.5 hours. N-Hydroxyacetimidamide (25 mg, 0.331 mmol) was added and the reaction mixture was warmed to room temperature and stirred overnight. The reaction mixture was cooled to 0 °C and the insoluble material was removed by filtration. The filtrate was concentrated in vacuo to give a dark brown oil. This was dissolved in dioxane (5 mL) and the mixture was heated at 110 °C for 7 hours, cooled to room temperature and stirred overnight. The mixture was concentrated in vacuo. The residue was purified by column chromatography on silica, eluting with 0-100% diethyl ether in cyclohexane, followed by reverse phase preparative HPLC to give the compound 44 as an off-white solid (32 mg, 29%).

Scheme 2q

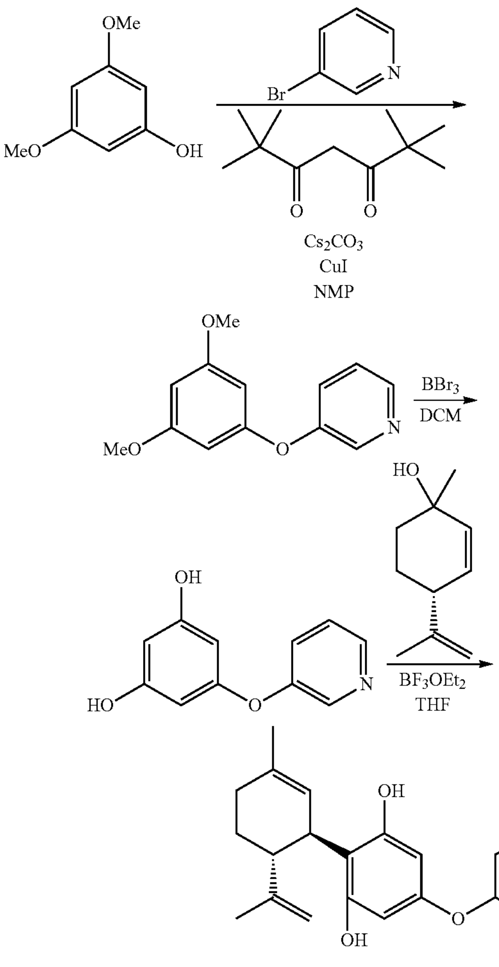

2,2,6,6-Tetramethyl-3,5-heptanedione (0.54 mL, 2.59 mmol) was added to stirred mixture of 3-bromopyridine (2.5 mL, 25.9 mmol), 3,5-dimethoxyphenol (2 g, 13.0 mmol), cesium carbonate (12.7 g, 38.9 mmol) and copper(I) iodide (247 mg, 1.30 mmol) in 1-methyl-2-pyrrolidinone (80 mL). The reaction was degassed for 5 min and heated at 140 °C for 24 hours. The reaction mixture was cooled to room temperature and filtered through celite. The filtrate was diluted with diethyl ether (150 mL) and washed with brine (5×30 mL). The organic layer was separated, dried (hydrophobic frit) and concentrated in vacuo. The residue was purified by column chromatography on silica, eluting with 0-100% ethyl acetate in cyclohexane to give 3-(3,5-dimethoxyphenoxy)pyridine (2.2 g, 73%) as a yellow oil.

Boron tribromide (30 mL, 29.8 mmol, 1.0M in dichloromethane) was added dropwise to a stirred solution of 3-(3,5-dimethoxyphenoxy)pyridine (2.3 g, 9.95 mmol) in dichloromethane (50 mL) at −10 °C. The reaction was allowed to warm slowly to room temperature and stirred overnight. The reaction was cooled to 0 °C and quenched with methanol (10 mL, 0.247 mol). The mixture was diluted with dichloromethane (50 mL) and neutralised to pH 8 with aqueous sodium hydrogen carbonate solution. The layers were separated and the aqueous layer extracted with dichloromethane (2×50 mL). The combined organic layers were combined, dried (hydrophobic frit) and concentrated in vacuo. The residue was purified by column chromatography on silica, eluting with 0-20% methanol in dichloromethane to give 5-(pyridin-3-yloxy)benzene-1,3-diol (900 mg, 44%) as a light brown solid.

Boron trifluoride diethyl etherate (0.35 mL, 2.87 mmol) was added to a stirred mixture of 5-(pyridin-3-yloxy)benzene-1,3-diol (530 mg, 2.61 mmol) in tetrahydrofuran (20 mL) at 0 °C (1S,4R)-4-isopropenyl-1-methyl-cyclohex-2-en-1-ol (0.51 mL, 3.13 mmol) was added dropwise. The reaction mixture was stirred at 0 °C for 1 hour and then allowed to warm to room temperature. Saturated aqueous sodium hydrogen carbonate solution (20 mL) was added and the mixture was extracted with ethyl acetate (2×30 mL). The combined organic layers were dried (hydrophobic frit) and concentrated in vacuo. The residue was purified by column chromatography on silica, eluting with 0-80% ethyl acetate in cyclohexane followed by reverse phase preparative HPLC to give the compound 47 as an off-white solid (7.4 mg, 0.8%).

Scheme 2r

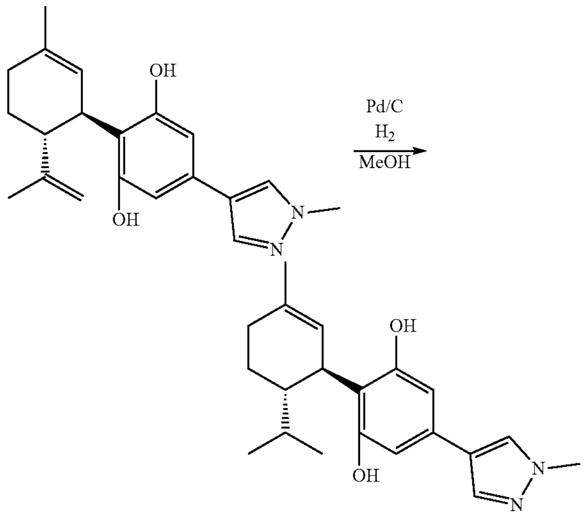

A solution of (1'R,2'R)-5'-methyl-4-(1-methyl-1H-pyrazol-4-yl)-2'-(prop-1-en-2-yl)-1',2',3',4'-tetrahydro-[1,1'-biphenyl]-2,6-diol (300 mg, 0.925 mmol) in methanol (10 mL) was treated with palladium on carbon (10%, 98 mg, 0.0925 mmol) and the reaction mixture stirred at room temperature under an atmosphere of hydrogen for 3 days. The reaction mixture was filtered through a pad of Celite, washing with methanol. The filtrate was concentrated in vacuo and the residue was purified by reverse phase preparative HPLC to give the compound 36 as an off-white solid (32 mg, 10%).
Compounds 1-48
1
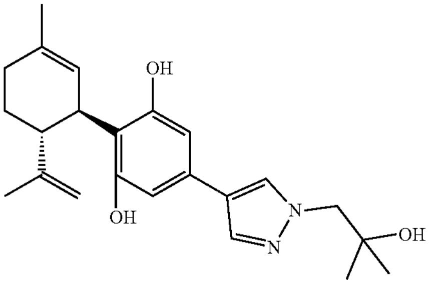
2
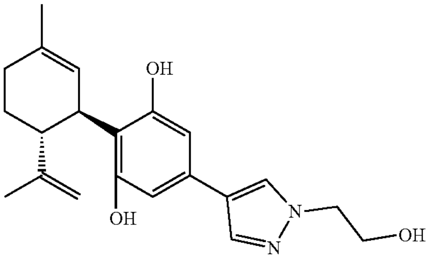
3
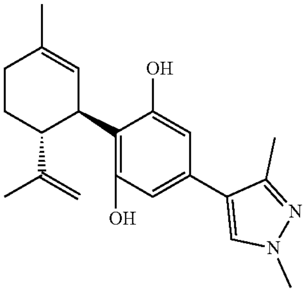
4
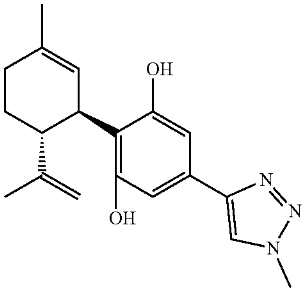
5
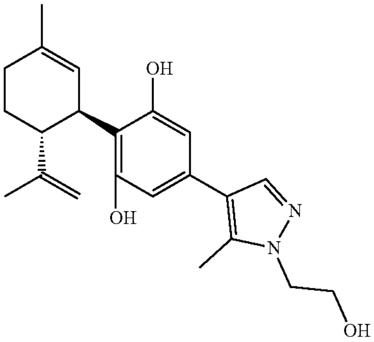
-continued
6
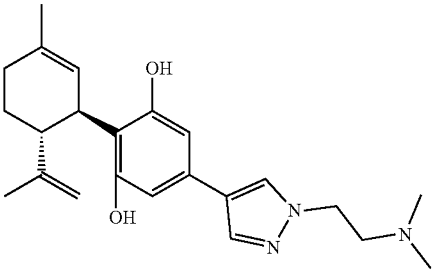
7
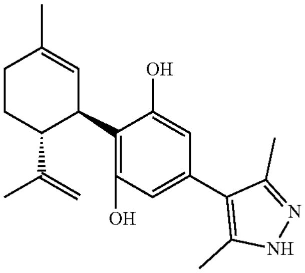
8
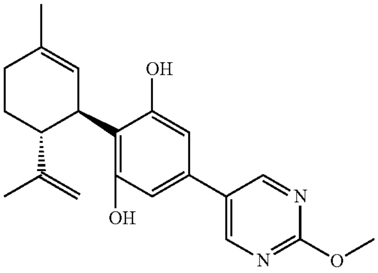
9
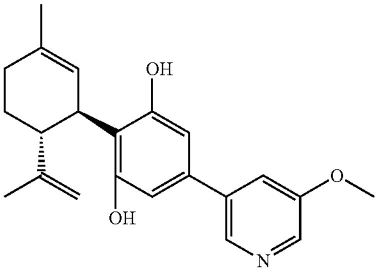
10
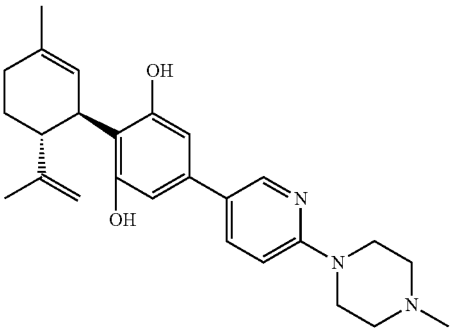

-continued
11
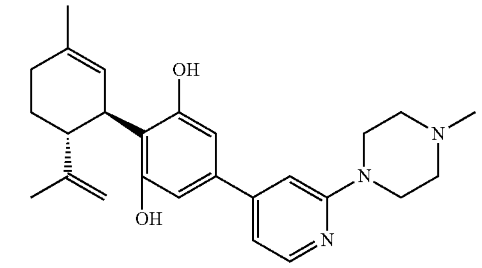
12
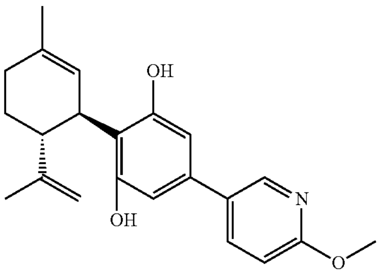
13
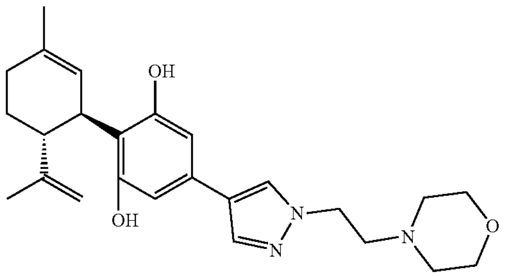
14
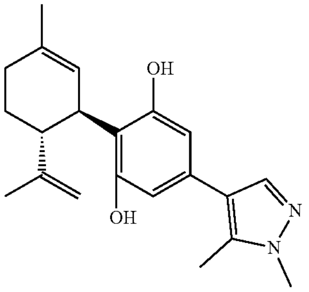
15
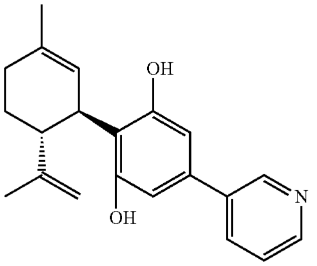
-continued
16
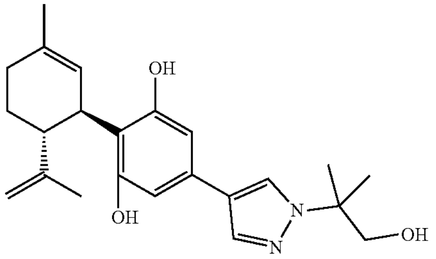
17
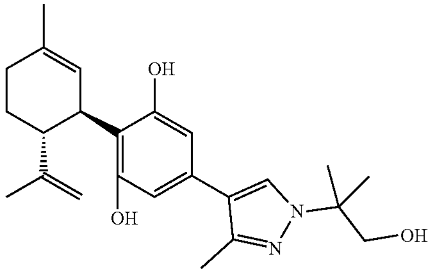
18
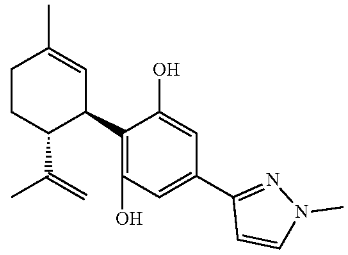
19
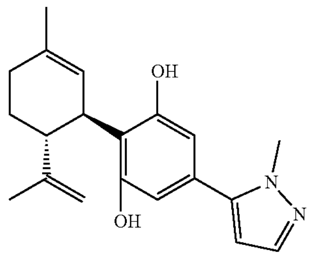
20
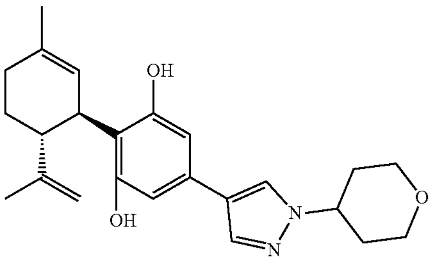
21
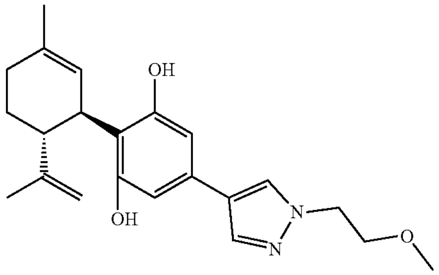

22
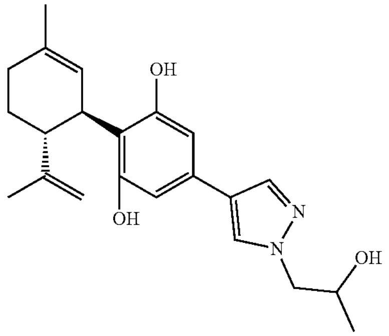
(Epimer 1)
23
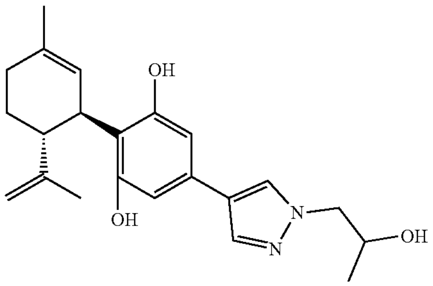
(Epimer 2)
24
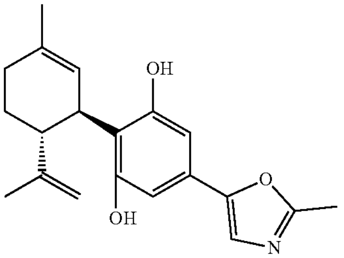
25
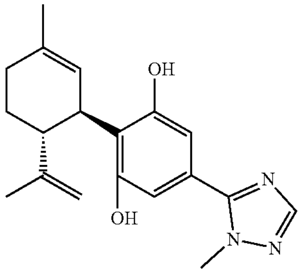
26
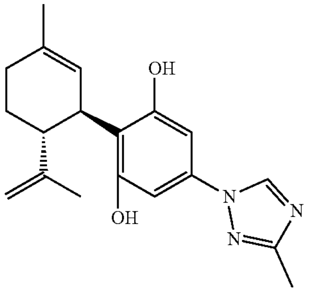
27
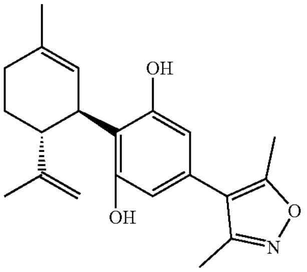
28
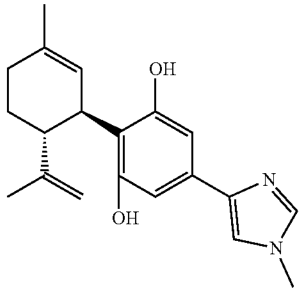
29
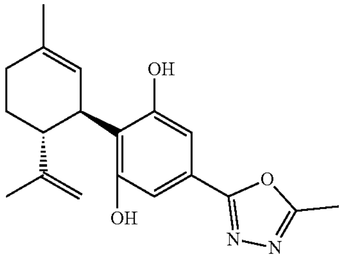
30
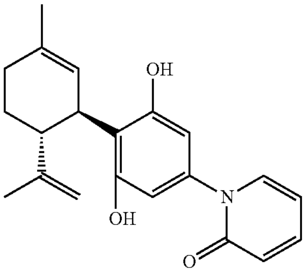
31
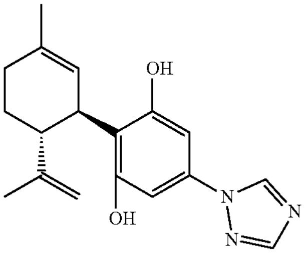

-continued
32
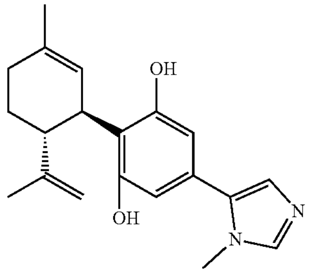
33
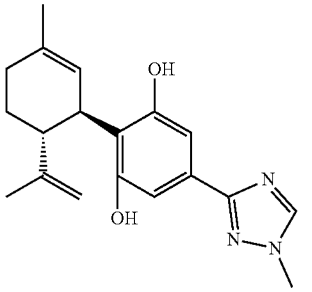
34
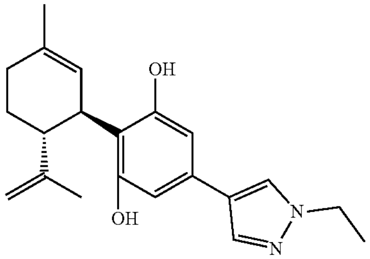
35
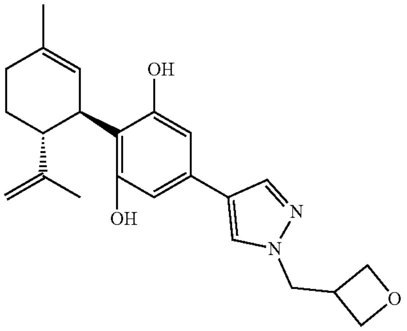
36
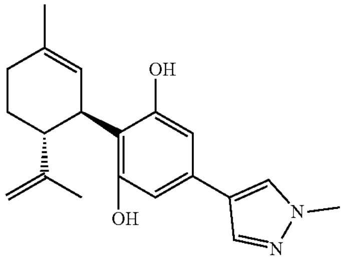
-continued
37
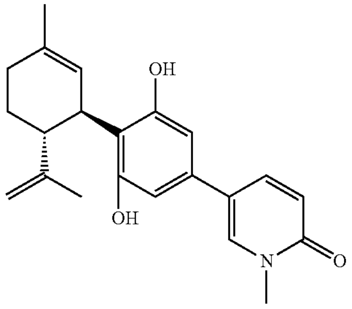
38
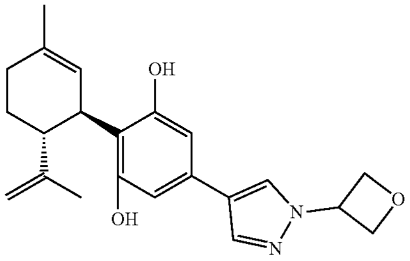
39
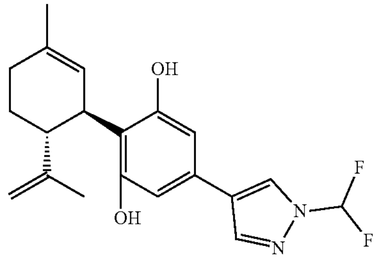
40
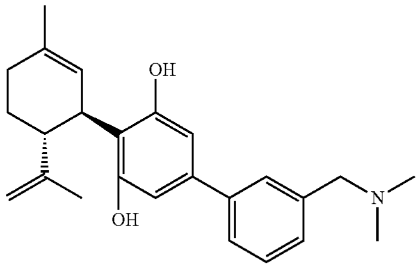
41
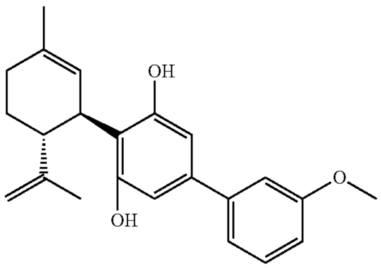

-continued

42

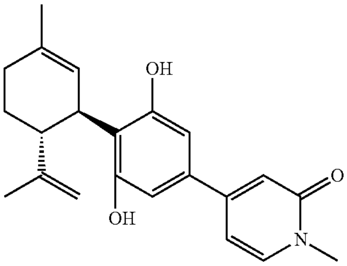

43

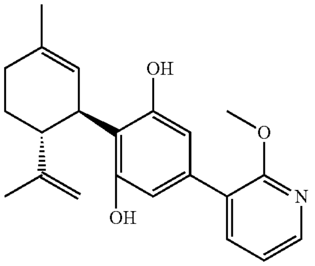

44

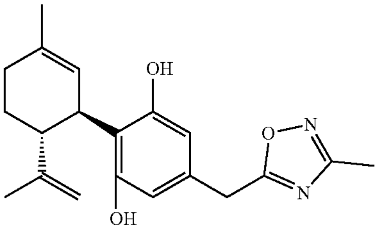

45

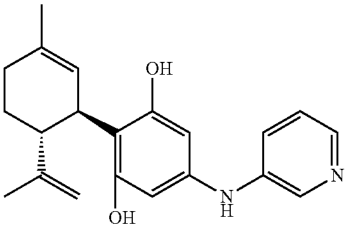

-continued

46

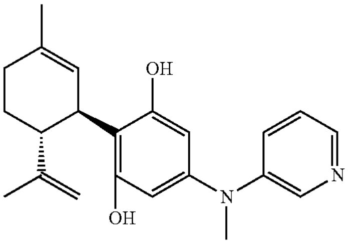

47

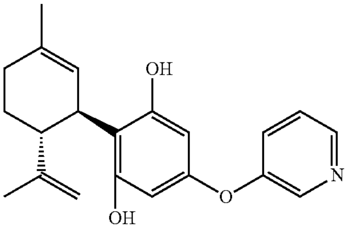

48

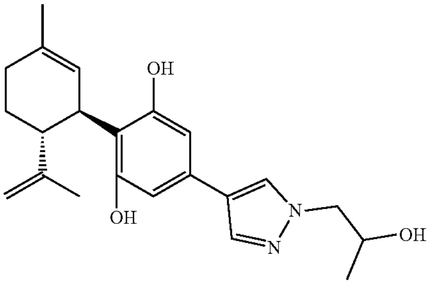

The compounds 1 to 48 were prepared by one of the synthetic routes of schemes 2a to 2r, substituting the appropriate boronic acid, boronate ester, tributylarylstannane, aryl bromide or nitrogen heterocycle. Table 1 below details the synthetic route and analytical data of each compound.

Note: Compounds 22 and 23 were formed as a mixture of epimers from racemic boronate ester and separated by chiral SFC.

TABLE 1

Detailed information of each compound 1-48 including name, analytical data and indication of synthetic route

| Compound | Name | Analytical data | Synthetic route (Scheme no.) |
|---|---|---|---|
| 1 | (1'R,2'R)-4-(1-(2-Hydroxy-2-methylpropyl)-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 8.88 (s, 2H), 7.80 (d, J = 0.6 Hz, 1H), 7.56 (d, J = 0.7 Hz, 1H), 6.37 (s, 2H), 5.13 (s, 1H), 4.72 (s, 1H), 4.52 (d, J = 2.6 Hz, 1H), 4.43 (dd, J = 1.4, 2.7 Hz, 1H), 4.03 (s, 2H), 3.89-3.86 (m, 1H), 3.10-3.02 (m, 1H), 2.17-2.08 (m, 1H), 1.97-1.92 (m, 1H), 1.73-1.64 (m, 2H), 1.63 (s, 3H), 1.61 (s, 3H), 1.08 (s, 6H). MS (ESI): m/z 383.3 (M + 1). HPLC purity: 99.0%. | 2a |
| 2 | (1'R,2'R)-4-(1-(2-Hydroxyethyl)-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 8.87 (s, 2H), 7.83 (s, 1H), 7.57 (s, 1H), 6.35 (s, 2H), 5.13 (s, 1H), 4.91 (t, J = 5.3 Hz, 1H), 4.52 (d, J = 2.6 Hz, 1H), 4.44 (s, 1H), 4.16 (t, J = 5.6 Hz, 2H), 3.89-3.84 (m, 1H), 3.75 (q, J = 5.6 Hz, 2H), 3.10-3.02 (m, 1H), 1.95 (d, J = 16.2 Hz, 1H), 1.73-1.64 (m, 2H), 1.62 (s, 3H), 1.63 (s, 3H). MS (ESI): m/z 355.5 (M + 1). HPLC purity: 99.0%. | 2b |
| 3 | (1'R,2'R)-4-(1,3-Dimethyl-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 8.86 (s, 2H), 7.64 (s, 1H), 6.28 (s, 2H), 5.13 (s, 1H), 4.55 (d, J = 2.6 Hz, 1H), 4.45 (dd, J = 1.4, 2.7 Hz, 1H), 3.91-3.87 (m, 1H), 3.77 (s, 3H), 3.13-3.05 (m, 1H), 2.25 (s, 3H), 2.18-2.10 (m, 1H), 1.96-1.92 (m, 1H), 1.75-1.65 (m, 2H), 1.62 (s, 3H), 1.62 (s, 3H). MS (ESI): m/z 339.3 (M + 1). HPLC purity: 98.6%. | 2b |
| 4 | (1'R,2'R)-5'-Methyl-4-(1-methyl-1H-1,2,3-triazol-4-yl)-2'-(prop-1-en-2-yl)-1',2',3',4'-tetrahydro-[1, 1'-biphenyl]-2,6-diol | $^1$H NMR (400 MHz, DMSO) d 9.05 (s, 2H), 8.21 (s, 1H), 6.67 (s, 2H), 5.14 (s, 1H), 4.53 (d, J = 2.6 Hz, 1H), 4.44 (dd, J = 1.3, 2.7 Hz, 1H), 3.93-3.89 (m, 1H), 3.13-3.05 (m, 1H), 2.15-2.10 (m, 1H), 2.00-1.92 (m, 1H), 1.76-1.62 (m, 8H). m/z 326.3 (M + 1). HPLC purity: 99.7%. | 2h |

TABLE 1-continued

Detailed information of each compound 1-48 including name, analytical data and indication of synthetic route

| Compound | Name | Analytical data | Synthetic route (Scheme no.) |
|---|---|---|---|
| 5 | (1'R,2'R)-4-(1-(2-Hydroxyethyl)-5-methyl-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 8.87 (s, 2H), 7.41 (s, 1H), 6.26 (s, 2H), 5.13 (s, 1H), 4.89 (t, J = 5.5 Hz, 1H), 4.55 (d, J = 2.8 Hz, 1H), 4.45 (dd, J = 1.4, 2.7 Hz, 1H), 4.10 (t, J = 5.8 Hz, 2H), 3.92 -3.86 (m, 1H), 3.72 (q, J = 5.6 Hz, 2H), 3.13-3.05 (m, 1H), 2.36 (s, 3H), 2.18-2.09 (m, 1H), 1.99-1.92 (m, 1H), 1.75-1.65 (m, 2H), 1.63 (s, 3H), 1.63 (s, 3H). MS (ESI): m/z 369.4 (M + 1). HPLC purity: 99.2%. | 2a |
| 6 | (1'R,2'R)-4-(1-(2-(Dimethylamino)ethyl)-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 8.89 (s, 2H), 7.87 (s, 1H), 7.55 (s, 1H), 6.35 (s, 2H), 5.13 (s, 1H), 4.52 (d, J = 2.6 Hz, 1H), 4.43 (s, 1H), 4.20 (dd, J = 6.5, 6.5 Hz, 2H), 3.89-3.84 (m, 1H), 3.10-3.02 (m, 1H), 2.65 (dd, J = 6.5, 6.5 Hz, 2H), 2.18 (s, 6H), 2.11 (d, J = 14.3 Hz, 1H), 2.01-1.92 (m, 1H), 1.73-1.64 (m, 2H), 1.63 (s, 3H), 1.62 (s, 3H). MS (ESI): m/z 382.3 (M + 1). HPLC purity: 97.8%. | 2a |
| 7 | (1'R,2'R)-4-(3,5-dimethyl-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 12.17 (s, 1H), 8.80 (s, 2H), 6.17 (s, 2H), 5.14 (s, 1H), 4.57 (d, J = 2.6 Hz, 1H), 4.47 (dd, J = 1.5, 2.7 Hz, 1H), 3.93-3.87 (m, 1H), 3.14-3.06 (m, 1H), 2.21 (s, 3H), 2.17 (s, 3H), 2.13-2.10 (m, 1H), 1.97-1.92 (m, 1H), 1.76-1.66 (m, 2H), 1.63 (s, 6H)MS (ESI): m/z 339.3 (M + 1). HPLC purity: 99.8%. | 2a |
| 8 | (1'R,2'R)-4-(2-methoxypyrimidin-5-yl)-5'-methyl-2'-(prop-1-en-2-yl)-1',2',3',4'-tetrahydro-[1,1'-biphenyl]-2,6-diol 2a | $^1$H NMR (400 MHz, DMSO) δ 9.22-9.22 (m, 2H), 8.70 (s, 2H), 6.45 (s, 2H), 5.12 (s, 1H), 4.55 (d, J = 2.8 Hz, 1H), 4.46 (s, 1H), 3.96 (s, 4H), 3.15-3.07 (m, 1H), 2.15 (s, 1H), 1.98-1.94 (m, 1H), 1.75-1.65 (m, 2H), 1.63 (s, 3H), 1.63 (s, 3H). MS (ESI): m/z 353.2 (M + 1). HPLC purity: 98.6%. | 2a |
| 9 | (1'R,2'R)-4-(5-methoxypyridin-3-yl)-5'-methyl-2'-(prop-1-en-2-yl)-1',2',3',4'-tetrahydro-[1,1'-biphenyl]-2,6-diol | $^1$H NMR (400 MHz, DMSO) δ 9.18 (s, 2H), 8.28 (d, J = 1.8 Hz, 1H), 8.25 (d, J = 2.8 Hz, 1H), 7.39 (dd, J = 2.3, 2.3 Hz, 1H), 6.51 (s, 2H), 5.13 (s, 1H), 4.56 (d, J = 2.6 Hz, 1H), 4.46 (s, 1H), 3.96-3.92 (m, 1H), 3.89 (s, 3H), 3.15-3.08 (m, 1H), 2.21-2.08 (m, 1H), 1.98-1.94 (m, 1H), 1.76-1.66 (m, 2H), 1.64 (s, 3H), 1.63 (s, 3H). MS (ESI): m/z 352.3 (M + 1). HPLC purity: 97.0%. | 2a |
| 10 | (1'R,2'R)-5'-methyl-4-(6-(4-methylpiperazin-1-yl)pyridin-3-yl)-2'-(prop-1-en-2-yl)-1',2',3',4'-tetrahydro-[1,1'-biphenyl]-2,6-diol | $^1$H NMR (400 MHz, DMSO) δ 9.01 (s, 2H), 8.24 (d, J = 2.4 Hz, 1H), 7.62 (dd, J = 2.6, 8.8 Hz, 1H), 6.89 (d, J = 8.9 Hz, 1H), 6.40 (s, 2H), 5.12 (s, 1H), 4.55 (d, J = 2.6 Hz, 1H), 4.45 (dd, J = 1.4, 2.6 Hz, 1H), 3.92-3.88 (m, 1H), 3.51 (t, J = 5.0 Hz, 4H), 3.14-3.06 (m, 1H), 2.41 (t, J = 5.0 Hz, 4H), 2.23 (s, 3H), 2.15-2.06 (m, 1H), 1.98-1.91 (m, 1H), 1.75-1.65 (m, 2H), 1.63 (s, 3H), 1.63 (s, 3H). MS (ESI): m/z 420.4 (M + 1). HPLC purity: 97.0%. | 2a |
| 11 | (1'R,2'R)-5'-methyl-4-(2-(4-methylpiperazin-1-yl)pyridin-4-yl)-2'-(prop-1-en-2-yl)-1',2',3',4'-tetrahydro-[1, 1'-biphenyl]-2,6-diol | $^1$H NMR (400 MHz, DMSO) δ 9.12 (s, 2H), 8.12 (d, J = 5.1 Hz, 1H), 6.82 (s, 1H), 6.73 (dd, J = 1.2, 5.2 Hz, 1H), 6.53 (s, 2H), 5.12 (s, 1H), 4.54 (d, J = 2.5 Hz, 1H), 4.45 (dd, J = 1.4, 2.7 Hz, 1H), 3.97-3.92 (m, 1H), 3.53 (t, J = 4.7 Hz, 4H), 3.15-3.07 (m, 1H), 2.43 (t, J = 5.0 Hz, 4H), 2.24 (s, 3H), 2.20-2.10 (m, 1H), 2.00-1.92 (m, 1H), 1.75-1.65 (m, 2H), 1.63 (s, 3H), 1.63 (s, 3H). m/z 420.4 (M + 1). HPLC purity: 99.3%. | 2a |
| 12 | (1'R,2'R)-4-(6-Methoxypyridin-3-yl)-5'-methyl-2'-(prop-1-en-2-yl)-1',2',3',4'-tetrahydro-[1,1'-biphenyl]-2,6-diol | $^1$H NMR (400 MHz, DMSO) δ 9.10 (s, 2H), 8.27 (d, J = 2.3 Hz, 1H), 7.79 (dd, J = 2.6, 8.6 Hz, 1H), 6.88 (dd, J = 0.7, 8.6 Hz, 1H), 6.43 (s, 2H), 5.13 (s, 1H), 4.56 (d, J = 2.6 Hz, 1H), 4.46 (dd, J = 1.5, 2.7 Hz, 1H), 3.96-3.90 (m, 1H), 3.89 (s, 3H), 3.15-3.07 (m, 1H), 2.20-2.09 (m, 1H), 1.98-1.93 (m, 1H), 1.64 (s, 3H), 1.63 (s, 3H). m/z 352.3 (M + 1). HPLC purity: 99.8%. | 2a |
| 13 | (1'R,2'R)-5'-Methyl-4-(1-(2-morpholinoethyl)-1H-pyrazol-4-yl)-2'-(prop-1-en-2-yl)-1',2',3',4'-tetrahydro-[1,1'-biphenyl]-2,6-diol | $^1$H NMR (400 MHz, DMSO) δ 8.89 (s, 2H), 7.89 (s, 1H), 7.56 (s, 1H), 6.35 (s, 2H), 5.13 (s, 1H), 4.52 (d, J = 2.6 Hz, 1H), 4.44 (dd, J = 1.4, 2.6 Hz, 1H), 4.24 (t, J = 6.5 Hz, 2H), 3.89-3.86 (m, 1H), 3.56 (t, J = 4.6 Hz, 4H), 3.11-3.03 (m, 1H), 2.72 (dd, J = 6.5, 6.5 Hz, 2H), 2.42 (dd, J = 4.3, 4.3 Hz, 4H), 2.18-2.09 (m, 1H), 1.97-1.92 (m, 1H), 1.77-1.64 (m, 2H), 1.63 (s, 3H), 1.62 (s, 3H). m/z 424.4 (M + 1). HPLC purity: 99.8%. | 2a |
| 14 | (1'R,2'R)-4-(1,5-Dimethyl-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) d 8.89 (s, 2H), 7.37 (s, 1H), 6.26 (s, 2H), 5.12 (s, 1H), 4.55 (d, J = 2.6 Hz, 1H), 4.45 (dd, J = 1.4, 2.8 Hz, 1H), 3.90-3.86 (m, 1H), 3.76 (s, 3H), 3.13-3.05 (m, 1H), 2.34 (s, 3H), 2.16-2.09 (m, 1H), 1.97-1.92 (m, 1H), 1.75-1.65 (m, 2H), 1.63 (s, 3H), 1.62 (s, 3H). m/z 339.3 (M + 1). HPLC purity: 98.9%. | 2a |
| 15 | (1'R,2'R)-5'-Methyl-2'-(prop-1-en-2-yl)-4-(pyridin-3-yl)-1',2',3',4'-tetrahydro-[1,1'-biphenyl]-2,6-diol | $^1$H NMR (400 MHz, DMSO) δ 9.19-9.19 (m, 2H), 8.69 (d, J = 1.9 Hz, 1H), 8.53 (dd, J = 1.4, 4.7 Hz, 1H), 7.86 (d, J = 8.3 Hz, 1H), 7.45 (dd, J = 4.8, 7.9 Hz, 1H), 6.50 (s, 2H), 5.14 (s, 1H), 4.56 (d, J = 2.4 Hz, 1H), 4.47 (s, 1H), 3.95 (d, J = 8.8 Hz, 1H), 3.16-3.08 (m, 1H), 2.15-2.08 (m, 1H), 2.01-1.91 (m, 1H), 1.65-1.62 (m, 8H). MS (ESI): m/z 322.4 (M + 1). HPLC purity: 99.1%. | 2a |
| 16 | (1'R,2'R)-4-(1-(1-Hydroxy-2-methylpropan-2-yl)-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) d 8.83 (s, 2H), 7.86 (d, J = 0.7 Hz, 1H), 7.58 (d, J = 0.7 Hz, 1H), 6.37 (s, 2H), 5.14 (s, 1H), 5.01 (t, J = 5.7 Hz, 1H), 4.51 (d, J = 2.6 Hz, 1H), 4.43 (dd, J = 1.5, 2.9 Hz, 1H), 3.88-3.85 (m, 1H), 3.60 (d, J = 5.6 Hz, 2H), 3.10-3.01 (m, 1H), 2.17-2.10 (m, 1H), 1.98-1.92 (m, 1H), 1.73-1.64 (m, 2H), 1.63 (s, 3H), 1.61 (s, 3H), 1.49 (s, 6H). MS (ESI): m/z 383.4 (M + 1). HPLC purity: 98.6%. | 2a |
| 17 | (1'R,2'R)-4-(1-(2-Hydroxyethyl)-3-methyl-1H-pyrazol-4-yl)-5'-methyl-2'-(prop-1-en-2-yl)-1',2',3',4'-tetrahydro-[1,1'-biphenyl]-2,6-diol | $^1$H NMR (400 MHz, DMSO) δ 8.87 (s, 2H), 7.66 (s, 1H), 6.30 (s, 2H), 5.13 (s, 1H), 4.88 (t, J = 5.3 Hz, 1H), 4.54 (d, J = 2.8 Hz, 1H), 4.45 (dd, J = 1.4, 2.6 Hz, 1H), 4.06 (t, J = 5.6 Hz, 2H), 3.90-3.86 (m, 1H), 3.72 (q, J = 5.5 Hz, 2H), 3.12-3.04 (m, 1H), 2.27 (s, 3H), 2.18-2.10 (m, 1H), 1.97-1.92 (m, 1H), 1.74-1.66 (m, 2H), 1.63 (s, 3H), 1.63 (s, 3H). MS (ESI): m/z 369.4 (M + 1). HPLC purity: 97.1%. | 2a |
| 18 | (1'R,2'R)-5'-Methyl-4-(1-methyl-1H-pyrazol-3-yl)-2'-(prop-1-en-2-yl)-1',2',3',4'-tetrahydro-[1,1'-biphenyl]-2,6-diol | $^1$H NMR (400 MHz, DMSO) δ 8.90 (s, 2H), 7.67 (d, J = 2.3 Hz, 1H), 6.64 (s, 2H), 6.35 (d, J = 2.3 Hz, 1H), 5.14 (s, 1H), 4.52 (d, J = 2.8 Hz, 1H), 4.43 (dd, J = 1.5, 2.7 Hz, 1H), 3.91-3.86 (m, 1H), 3.85 (s, 3H), 3.12-3.03 (m, 1H), 2.17-2.08 (m, 1H), 1.97-1.92 (m, 1H), 1.74-1.67 (m, 2H), 1.63 (s, 3H), 1.62 (s, 3H). MS (ESI): m/z 325.0 (M + 1). HPLC purity: 97.5%. | 2b |

TABLE 1-continued

Detailed information of each compound 1-48 including name, analytical data and indication of synthetic route

| Compound | Name | Analytical data | Synthetic route (Scheme no.) |
|---|---|---|---|
| 19 | (1'R,2'R)-5'-Methyl-4-(1-methyl-1H-pyrazol-5-yl)-2'-(prop-1-en-2-yl)-1',2',3',4'-tetrahydro-[1,1'-biphenyl]-2,6-diol | $^{1}$H NMR (400 MHz, DMSO) δ 9.17 (s, 2H), 7.42 (d, J = 1.9 Hz, 1H), 6.34 (s, 2H), 6.25 (d, J = 1.8 Hz, 1H), 5.14 (s, 1H), 4.55 (d, J = 2.6 Hz, 1H), 4.47 (dd, J = 1.5, 2.8 Hz, 1H), 3.99-3.90 (m, 1H), 3.81 (s, 3H), 3.19-3.07 (m, 1H), 2.14-2.09 (m, 1H), 1.98-1.93 (m, 1H), 1.79-1.62 (m, 8H). MS (ESI): m/z 325.2 (M + 1). HPLC purity: 99.3%. | 2b |
| 20 | (1'R,2'R)-5'-Methyl-2'-(prop-1-en-2-yl)-4-(1-(tetrahydro-2H-pyran-4-yl)-1H-pyrazol-4-yl)-1',2',3',4'-tetrahydro-[1,1'-biphenyl]-2,6-diol | $^{1}$H NMR (400 MHz, DMSO) δ 8.88 (s, 2H), 7.93 (s, 1H), 7.59 (s, 1H), 6.36 (s, 2H), 5.14 (s, 1H), 4.51 (d, J = 2.5 Hz, 1H), 4.43-4.39 (m, 2H), 4.00-3.96 (m, 2H), 3.86 (dd, J = 2.0, 8.5 Hz, 1H), 3.52-3.40 (m, 3H), 3.10-3.02 (m, 1H), 2.14 -2.08 (m, 1H), 2.00-1.94 (m, 4H), 1.73-1.64 (m, 2H), 1.63 (s, 3H), 1.61 (s, 3H). MS (ESI): m/z 395.5 (M + 1). HPLC purity: 98.3%. | 2b |
| 21 | (1'R,2'R)-4-(1-(2-Methoxyethyl)-1H-pyrazol-4-yl)-5'-methyl-2'-(prop-1-en-2-yl)-1',2',3',4'-tetrahydro-[1,1'-biphenyl]-2,6-diol | $^{1}$H NMR (400 MHz, DMSO) δ 8.88 (s, 2H), 7.84 (d, J = 0.7 Hz, 1H), 7.57 (d, J = 0.8 Hz, 1H), 6.35 (s, 2H), 5.13 (s, 1H), 4.52 (d, J = 2.8 Hz, 1H), 4.43 (dd, J = 1.5, 2.7 Hz, 1H), 4.27 (t, J = 5.3 Hz, 2H), 3.89-3.86 (m, 1H), 3.70 (t, J = 5.3 Hz, 2H), 3.25 (s, 3H), 3.10-3.02 (m, 1H), 2.18-2.09 (m, 1H), 1.98-1.92 (m, 1H), 1.73-1.64 (m, 2H), 1.63 (s, 3H), 1.62 (s, 3H).MS (ESI): m/z 369.3 (M + 1). HPLC purity: 98.5%. | 2b |
| 22 | (1'R,2'R)-4-(1-(2-Hydroxypropyl)-1H-pyrazol-4-yl)-5'-methyl-2'-(prop-1-en-2-yl)-1',2',3',4'-tetrahydro-[1,1'-biphenyl]-2,6-diol (Epimer 1) | $^{1}$H NMR (400 MHz, DMSO) δ 8.88 (s, 2H), 7.81 (d, J = 0.7 Hz, 1H), 7.56 (d, J = 0.7 Hz, 1H), 6.35 (s, 2H), 5.13 (s, 1H), 4.93 (d, J = 4.8 Hz, 1H), 4.52 (d, J = 2.5 Hz, 1H), 4.43 (dd, J = 1.4, 2.7 Hz, 1H), 4.04-3.97 (m, 3H), 3.89-3.85 (m, 1H), 3.10-3.03 (m, 2H), 2.70-2.67 (m, 1H), 2.36-2.33 (m, 1H), 2.17-2.08 (m, 1H), 1.98-1.92 (m, 1H), 1.70-1.64 (m, 2H), 1.63 (s, 3H), 1.61 (s, 3H), 1.04 (d, J = 5.9 Hz, 3H). MS (ESI): m/z 369.3 (M + 1). HPLC purity: 97.4%. | 2b |
| 23 | (1'R,2'R)-4-(1-(2-Hydroxypropyl)-1H-pyrazol-4-yl)-5'-methyl-2'-(prop-1-en-2-yl)-1',2',3',4'-tetrahydro-[1,1'-biphenyl]-2,6-diol (Epimer 2) | $^{1}$H NMR (400 MHz, DMSO) δ 8.88 (s, 2H), 7.81 (d, J = 0.8 Hz, 1H), 7.56 (d, J = 0.8 Hz, 1H), 6.35 (s, 2H), 5.13 (s, 1H), 4.93 (d, J = 4.8 Hz, 1H), 4.52 (d, J = 2.6 Hz, 1H), 4.43 (dd, J = 1.3, 2.8 Hz, 1H), 4.04-4.00 (m, 3H), 3.89-3.86 (m, 1H), 3.45-3.39 (m, 1H), 3.31 (s, 1H), 3.10-3.02 (m, 1H), 2.69-2.67 (m, 1H), 2.35 (dd, J = 1.9, 3.6 Hz, 1H), 2.18-2.10 (m, 1H), 1.97-1.92 (m, 1H), 1.71-1.64 (m, 2H), 1.63 (s, 3H), 1.61 (s, 3H), 1.04 (d, J = 5.9 Hz, 3H). MS (ESI): m/z 369.4 (M + 1). HPLC purity: 95.1%. | 2b |
| 24 | (1'R,2'R)-5'-Methyl-4-(2-methyloxazol-5-yl)-2'-(prop-1-en-2-yl)-1',2',3',4'-tetrahydro-[1,1'-biphenyl]-2,6-diol | $^{1}$H NMR (400 MHz, DMSO) δ 9.17 (s, 2H), 7.18 (s, 1H), 6.50 (s, 2H), 5.13 (s, 1H), 4.50 (d, J = 2.6 Hz, 1H), 4.43 (s, 1H), 3.90 (dd, J = 1.8, 10.6 Hz, 1H), 3.10-3.02 (m, 1H), 2.45 (s, 3H), 2.17-2.08 (m, 1H), 1.98-1.93 (m, 1H), 1.75-1.64 (m, 2H), 1.63 (s, 3H), 1.62 (s, 3H). m/z 326.4 (M + 1). HPLC purity: 99.8%. | 2g |
| 25 | (1'R,2'R)-5'-Methyl-4-(1-methyl-1H-1,2,4-triazol-5-yl)-2'-(prop-1-en-2-yl)-1',2',3',4'-tetrahydro-[1,1'-biphenyl]-2,6-diol | $^{1}$H NMR (400 MHz, DMSO) δ 9.33 (s, 2H), 7.93 (s, 1H), 6.65 (s, 2H), 5.14 (s, 1H), 4.54 (d, J = 2.6 Hz, 1H), 4.46 (dd, J = 1.5, 2.7 Hz, 1H), 3.99-3.95 (m, 1H), 3.94 (s, 3H), 3.15-3.08 (m, 1H), 2.17-2.10 (m, 1H), 2.01-1.94 (m, 1H), 1.76-1.66 (m, 2H), 1.64 (s, 6H). | 2 |
| 26 | (1'R,2'R)-5'-Methyl-4-(3-methyl-1H-1,2,4-triazol-1-yl)-2'-(prop-1-en-2-yl)-1',2',3',4'-tetrahydro-[1,1'-biphenyl]-2,6-diol | $^{1}$H NMR (400 MHz, DMSO) d 9.46 (s, 2H), 8.86 (s, 1H), 6.64 (s, 2H), 5.18 (s, 1H), 4.55 (s, 1H), 4.51-4.47 (m, 1H), 3.94 (d, J = 10.1 Hz, 1H), 3.13-3.06 (m, 1H), 2.37 (s, 3H), 2.22-2.13 (m, 1H), 2.04-1.96 (m, 1H), 1.78-1.69 (m, 2H), 1.68 (s, 3H), 1.66 (s, 3H). m/z 326.4 (M + 1). HPLC purity: 98.1%. | 21 |
| 27 | (1'R,2'R)-4-(3,5-dimethylisoxazol-4-yl)-5'-methyl-2'-(prop-1-en-2-yl)-1',2',3',4'-tetrahydro-[1,1'-biphenyl]-2,6-diol | $^{1}$H NMR (400 MHz, DMSO) δ 9.05 (s, 2H), 6.22 (s, 2H), 5.13 (s, 1H), 4.56 (d, J = 2.6 Hz, 1H), 4.47 (s, 1H), 3.92 (dd, J = 1.9, 8.7 Hz, 1H), 3.19-3.06 (m, 1H), 2.39 (s, 3H), 2.21 (s, 3H), 2.21-2.10 (m, 1H), 1.97-1.88 (m, 1H), 1.75-1.70 (m, 1H), 1.66-1.60 (m, 1H), 1.63 (s, 3H), 1.63 (s, 3H). | 2m |
| 28 | (1'R,2'R)-5'-Methyl-4-(1-methyl-1H-imidazol-4-yl)-2'-(prop-1-en-2-yl)-1',2',3',4'-tetrahydro-[1,1'-biphenyl]-2,6-diol | $^{1}$H NMR (400 MHz, DMSO) d 8.82 (s, 2H), 7.55 (s, 1H), 7.25 (d, J = 1.2 Hz, 1H), 6.60 (s, 2H), 5.14 (s, 1H), 4.52 (d, J = 2.6 Hz, 1H), 4.43 (dd, J = 1.5, 2.8 Hz, 1H), 3.90-3.85 (m, 1H), 3.67 (s, 3H), 3.11-3.03 (m, 1H), 2.18-2.08 (m, 1H), 1.96-1.91 (m, 1H), 1.62 (s, 8H). MS (ESI): m/z 325.3 (M + 1). HPLC purity: 91.4%. | 2k |
| 29 | (1'R,2'R)-5'-Methyl-4-(5-methyl-1,3,4-oxadiazol-2-yl)-2'-(prop-1-en-2-yl)-1',2',3',4'-tetrahydro-[1,1'-biphenyl]-2,6-diol | $^{1}$H NMR (400 MHz, DMSO) δ 9.49 (s, 2H), 6.86 (s, 2H), 5.13 (s, 1H), 4.50 (d, J = 2.4 Hz, 1H), 4.45-4.43 (m, 1H), 3.97-3.94 (m, 1H), 3.13-3.05 (m, 1H), 2.55 (s, 3H), 2.19-2.10 (m, 1H), 2.01-1.93 (m, 1H), 1.75-1.65 (m, 2H), 1.64 (s, 3H), 1.62 (s, 3H). MS (ESI): m/z 327.3 (M + 1). HPLC purity: 97.0%. | 2h |
| 30 | 1-((1'R,2'R)-2,6-dihydroxy-5'-methyl-2'-(prop-1-en-2-yl)-1',2',3',4'-tetrahydro-[1,1'-biphenyl]-4-yl)pyridin-2(1H)-one | $^{1}$H NMR (400 MHz, DMSO) d 9.35 (s, 2H), 7.55 (dd, J = 1.8, 6.8 Hz, 1H), 7.47 (ddd, J = 2.3, 6.7, 9.1 Hz, 1H), 6.44 (d, J = 9.2 Hz, 1H), 6.25 (dt, J = 1.3, 6.7 Hz, 1H), 6.20 (s, 2H), 5.12 (s, 1H), 4.60 (d, J = 2.5 Hz, 1H), 4.49 (dd, J = 1.5, 2.6 Hz, 1H), 3.96-3.93 (m, 1H), 3.16-3.08 (m, 1H), 2.15-2.09 (m, 1H), 1.99 (d, J = 4.4 Hz, 1H), 1.77-1.71 (m, 1H), 1.70-1.58 (m, 7H). MS (ESI): m/z 338.3 (M + 1). HPLC purity: 95.0%. | 2n |
| 31 | 2-[(1R,6R)-6-Isopropenyl-3-methyl-cyclohex-2-en-1-yl]-5-(1,2,4-triazol-1-yl)benzene-1,3-diol | $^{1}$H NMR (400 MHz, DMSO) δ 9.50 (s, 2H), 9.00 (s, 1H), 8.16 (s, 1H), 6.64 (s, 2H), 5.14 (s, 1H), 4.52 (d, J = 2.6 Hz, 1H), 4.45 (dd, J = 1.4, 2.7 Hz, 1H), 3.95-3.90 (m, 1H), 3.12-3.04 (m, 1H), 2.20-2.09 (m, 1H), 1.98-1.94 (m, 1H), 1.79-1.65 (m, 2H), 1.64 (s, 3H), 1.63 (s, 3H). MS (ESI): m/z 312.2 (M + 1). HPLC purity: 95.8%. | 21 |
| 32 | (1'R,2'R)-5'-Methyl-4-(1-methyl-1H-imidazol-5-yl)-2'-(prop-1-en-2-yl)-1',2',3',4'-tetrahydro-[1,1'-biphenyl]-2,6-diol | $^{1}$H NMR (400 MHz, DMSO) δ 9.12 (s, 2H), 8.42 (s, 1H), 7.62 (s, 1H), 6.89 (d, J = 1.2 Hz, 1H), 6.32 (s, 2H), 5.14 (s, 1H), 4.55 (d, J = 2.6 Hz, 1H), 4.46 (dd, J = 1.5, 2.7 Hz, 1H), 3.94-3.90 (m, 1H), 3.64 (s, 3H), 3.14-3.06 (m, 1H), 2.20-2.10 (m, 1H), 1.99-1.93 (m, 1H), 1.75-1.62 (m, 8H). MS (ESI): m/z 325.3 (M + 1). HPLC purity: 94.1%. | 2i |
| 33 | (1'R,2'R)-5'-Methyl-4-(1-methyl-1H-1,2,4-triazol-3-yl)-2'-(prop-1-en-2-yl)-1',2',3',4'-tetrahydro-[1, 1'-biphenyl]-2,6-diol | $^{1}$H NMR (400 MHz, DMSO) δ 9.06 (s, 2H), 8.42 (s, 1H), 6.92 (s, 2H), 5.14 (s, 1H), 3.13-4.52 (d, J = 2.6 Hz, 1H), 4.43 (dd, J = 1.4, 2.8 Hz, 1H), 3.95-3.88 (m, 4H), 3.05 (m, 1H), 2.18-2.09 (m, 1H), 2.00-1.92 (m, 1H), 1.74-1.65 (m, 2H), 1.64 (s, 3H), 1.62 (s, 3H). MS (ESI): m/z 326.3 (M + 1). HPLC purity: 98.9%. | 2j |

TABLE 1-continued

Detailed information of each compound 1-48 including name, analytical data and indication of synthetic route

| Compound | Name | Analytical data | Synthetic route (Scheme no.) |
|---|---|---|---|
| 34 | (1'R,2'R)-4-(1-Ethyl-1H-pyrazol-4-yl)-5'-methyl-2'-(prop-1-en-2-yl)-1',2',3',4'-tetrahydro-[1,1'-biphenyl]-2,6-diol | $^{1}$H NMR (400 MHz, DMSO) δ 8.87 (s, 2H), 7.87 (s, 1H), 7.56 (d, J = 0.8 Hz, 1H), 6.35 (s, 2H), 5.13 (s, 1H), 4.52 (d, J = 2.8 Hz, 1H), 4.43 (dd, J = 1.4, 2.8 Hz, 1H), 4.14 (q, J = 7.2 Hz, 2H), 3.89-3.85 (m, 1H), 3.10-3.02 (m, 1H), 2.17-2.08 (m, 1H), 1.97-1.92 (m, 1H), 1.73-1.64 (m, 2H), 1.63 (s, 3H), 1.62 (s, 3H), 1.39 (t, J = 7.3 Hz, 3H). MS (ESI): m/z 339.4 (M + 1). HPLC purity: 96.7%. | 2a |
| 35 | (1'R,2'R)-5'-Methyl-4-(1-(oxetan-3-ylmethyl)-1H-pyrazol-4-yl)-2'-(prop-1-en-2-yl)-1',2',3',4'-tetrahydro-[1,1'-biphenyl]-2,6-diol | $^{1}$H NMR (400 MHz, DMSO) δ 8.89 (s, 2H), 7.91 (d, J = 0.7 Hz, 1H), 7.58 (d, J = 0.7 Hz, 1H), 6.35 (s, 2H), 5.13 (s, 1H), 4.65 (dd, J = 6.2, 7.8 Hz, 2H), 4.51 (d, J = 2.6 Hz, 1H), 4.45-4.41 (m, 5H), 3.90-3.84 (m, 1H), 3.46-3.38 (m, 1H), 3.10-3.02 (m, 1H), 2.15-2.09 (m, 1H), 1.97-1.91 (m, 1H), 1.73-1.64 (m, 2H), 1.63 (s, 3H), 1.61 (s, 3H). MS (ESI): m/z 381.4 (M + 1). HPLC purity: 97.5%. | 2b |
| 36 | (1'S,2'S)-2'-Isopropyl-5'-methyl-4-(1-methyl-1H-pyrazol-4-yl)-1',2',3',4'-tetrahydro-[1,1'-biphenyl]-2,6-diol | $^{1}$H NMR (400 MHz, DMSO) d 8.86-8.86 (m, 2H), 7.84 (s, 1H), 7.56 (s, 1H), 6.37 (s, 2H), 5.11 (s, 1H), 3.86 (s, 3H), 3.75-3.72 (m, 1H), 2.19-2.02 (m, 2H), 1.96-1.92 (m, 1H), 1.75-1.69 (m, 1H), 1.61 (s, 3H), 1.53-1.45 (m, 1H), 1.32-1.20 (m, 1H), 0.81 (d, J = 7.0 Hz, 3H), 0.77 (d, J = 6.8 Hz, 3H) | 2r |
| 37 | 5-((1'R,2'R)-2,6-Dihydroxy-5'-methyl-2'-(prop-1-en-2-yl)-1',2',3',4'-tetrahydro-[1,1'-biphenyl]-4-yl)-1-methylpyridin-2(1H)-one | $^{1}$H NMR (400 MHz, DMSO) □ 9.03 (s, 2H), 7.87 (d, J = 2.5 Hz, 1H), 7.60 (dd, J = 2.7, 9.5 Hz, 1H), 6.50 (d, J = 9.3 Hz, 1H), 6.35 (s, 2H), 5.16 (s, 1H), 4.57 (d, J = 2.5 Hz, 1H), 4.48 (dd, J = 1.5, 2.5 Hz, 1H), 3.98-3.91 (m, 1H), 3.53 (s, 3H), 3.16-3.08 (m, 1H), 2.22-2.12 (m, 1H), 2.02-1.95 (m, 1H), 1.80-1.72 (m, 1H), 1.71-1.62 (m, 8H). MS (ESI): m/z 352 (M + 1). HPLC purity: 96.7%. | 2c |
| 38 | (1'R,2'R)-5'-Methyl-4-(1-(oxetan-3-yl)-1H-pyrazol-4-yl)-2'-(prop-1-en-2-yl)-11,2',3',4'-tetrahydro-[1, 1'-biphenyl]-2,6-diol | $^{1}$H NMR (400 MHz, DMSO) □□8.91 (s, 2H), 8.02 (d, J = 0.6 Hz, 1H), 7.73 (s, 1H), 6.37 (s, 2H), 5.65-5.58 (m, 1H), 5.13 (s, 1H), 4.92 (d, J = 7.0 Hz, 4H), 4.52 (d, J = 2.6 Hz, 1H), 4.43 (dd, J = 1.4, 2.7 Hz, 1H), 3.91-3.85 (m, 1H), 3.11-3.02 (m, 1H), 2.17-2.10 (m, 1H), 1.97-1.92 (m, 1H), 1.73-1.67 (m, 1H), 1.67-1.64 (m, 1H), 1.63 (s, 3H), 1.62 (s, 3H). MS (ESI): m/z 367.2 (M + 1). HPLC purity: 98.7%. | 2d |
| 39 | (1'R,2'R)-4-(1-(Difluoromethyl)-1H-pyrazol-4-yl)-5'-methyl-2'-(prop-1-en-2-yl)-1',2',3',4'-tetrahydro-[1,1'-biphenyl]-2,6-diol | $^{1}$H NMR (400 MHz, DMSO) □ 9.03 (s, 2H), 8.37 (d, J = 0.5 Hz, 1H), 7.96 (s, 1H), 7.81 (t, J = 58.6 Hz, 1H), 6.42 (s, 2H), 5.13 (s, 1H), 4.52 (d, J = 2.8 Hz, 1H), 4.44 (dd, J = 1.4, 2.7 Hz, 1H), 3.94-3.87 (m, 1H), 3.12-3.04 (m, 1H), 2.17-2.08 (m, 1H), 1.98-1.92 (m, 1H), 1.76-1.65 (m, 2H), 1.64 (s, 3H), 1.63 (s, 3H). MS (ESI): m/z 361.3 (M + 1). HPLC purity: 99.4%. | 2e |
| 40 | (1R,2R)-3''-((Dimethylamino)methyl)-5-methyl-2-(prop-1-en-2-yl)-1,2,3,4-tetrahydro-[1,1':4',1''-terphenyl]-2',6'-diol | $^{1}$H NMR (400 MHz, DMSO) □ 9.06 (s, 2H), 7.47 (s, 1H), 7.42-7.39 (m, 2H), 7.27-7.23 (m, 1H), 6.55 (s, 2H), 5.18 (s, 1H), 4.59 (d, J = 2.5 Hz, 1H), 4.49 (dd, J = 1.4, 2.6 Hz, 1H), 3.98-3.94 (m, 1H), 3.47 (s, 2H), 3.19-3.11 (m, 1H), 2.21 (s, 6H), 2.17 (d, J = 8.6 Hz, 1H), 2.05-1.96 (m, 1H), 1.81-1.70 (m, 2H), 1.67 (s, 3H), 1.67 (s, 3H). | 2f |
| 41 | (1R,2R)-3''-Methoxy-5-methyl-2-(prop-1-en-2-yl)-1,2,3,4-tetrahydro-[1,1':4', 1''-terphenyl]-2',6'-diol (GWP04205258) | $^{1}$H NMR (400 MHz, DMSO) □ 9.07 (s, 2H), 7.38 (t, J = 7.8 Hz, 1H), 7.08 (d, J = 7.8 Hz, 1H), 7.03 (s, 1H), 6.93 (dd, J = 2.3, 8.1 Hz, 1H), 6.52 (s, 2H), 5.17 (s, 1H), 4.61-4.59 (m, 1H), 4.50 (s, 1H), 3.97 (d, J = 9.9 Hz, 1H), 3.85 (s, 3H), 3.19-3.11 (m, 1H), 2.25-2.13 (m, 1H), 2.04-1.97 (m, 1H), 1.81-1.73 (m, 1H), 1.73-1.63 (m, 7H). MS (ESI): m/z 351.2 (M + 1). HPLC purity: 98.8%. | 2c |
| 42 | 4-((1'R,2'R)-2,6-dihydroxy-5'-methyl-2'-(prop-1-en-2-yl)-1',2',3',4'-tetrahydro-[1,1'-biphenyl]-4-yl)-1-methylpyridin-2(1H)-one | $^{1}$H NMR (400 MHz, DMSO) δ 9.21 (s, 2H), 7.72 (d, J = 7.0 Hz, 1H), 6.49 (s, 2H), 6.39 (d, J = 2.0 Hz, 1H), 6.33 (dd, J = 2.1, 7.1 Hz, 1H), 5.11 (s, 1H), 4.54 (d, J = 2.5 Hz, 1H), 4.45 (dd, J = 1.4, 2.6 Hz, 1H), 3.95-3.92 (m, 1H), 3.44 (s, 3H), 3.14-3.06 (m, 1H), 2.15-2.10 (m, 1H), 1.97 (s, 1H), 1.77-1.64 (m, 2H), 1.63 (s, 3H), 1.63 (s, 3H). m/z 352.3 (M + 1). HPLC purity: 97.7%. | 2j |
| 43 | (1'R,2'R)-4-(2-methoxypyridin-3-yl)-5'-methyl-2'-(prop-1-en-2-yl)-1',2',3',4'-tetrahydro-[1,1'-biphenyl]-2,6-diol | $^{1}$H NMR (400 MHz, DMSO) δ 9.04 (s, 2H), 8.17 (dd, J = 1.9, 4.9 Hz, 1H), 7.66 (dd, J = 2.0, 7.3 Hz, 1H), 7.09 (dd, J = 5.1, 7.3 Hz, 1H), 6.46 (s, 2H), 5.17 (s, 1H), 4.63 (d, J = 2.8 Hz, 1H), 4.52 (dd, J = 1.4, 2.7 Hz, 1H), 3.99 (dd, J = 1.6, 10.5 Hz, 1H), 3.92 (s, 3H), 3.21-3.13 (m, 1H), 2.20-2.13 (m, 1H), 2.02-1.96 (m, 1H), 1.81-1.71 (m, 2H), 1.69 (s, 3H), 1.67 (s, 3H). m/z 352.3 (M + 1). HPLC purity: 98.9%. | 2f |
| 44 | (1'R,2'R)-5'-Methyl-4-((3-methyl-1,2,4-oxadiazol-5-yl)methyl)-2'-(prop-1-en-2-yl)-1',2',3',4'-tetrahydro-[1,1'-biphenyl]-2,6-diol | $^{1}$H NMR (400 MHz, DMSO) □ 8.98-8.98 (m, 2H), 6.14 (s, 2H), 5.07 (s, 1H), 4.51 (d, J = 2.6 Hz, 1H), 4.42 (s, 1H), 4.02 (s, 2H), 3.86 (dd, J = 1.9, 8.7 Hz, 1H), 3.09-3.01 (m, 1H), 2.32 (s, 3H), 2.16-2.08 (m, 1H), 1.95-1.91 (m, 1H), 1.72-1.62 (m, 2H), 1.60 (s, 6H). MS (ESI): m/z 341.3 (M + 1). HPLC purity: 93.8%. | 2p |
| 45 | (1'R,2'R)-5'-Methyl-2'-(prop-1-en-2-yl)-4-(pyridin-3-ylamino)-1',2',3',4'-tetrahydro-[1,1'-biphenyl]-2,6-diol | $^{1}$H NMR (400 MHz, DMSO) δ 8.86-8.80 (m, 2H), 8.34 (d, J = 2.5 Hz, 1H), 8.02-8.00 (m, 2H), 7.45-7.41 (m, 1H), 7.24 (dd, J = 4.7, 8.2 Hz, 1H), 6.09 (s, 2H), 5.17 (s, 1H), 4.57 (d, J = 2.5 Hz, 1H), 4.49 (dd, J = 1.4, 2.7 Hz, 1H), 3.88-3.80 (m, 1H), 3.11-3.02 (m, 1H), 2.22-2.09 (m, 1H), 2.02-1.95 (m, 1H), 1.78-1.69 (m, 2H), 1.66 (s, 6H). MS (ESI): m/z 337.2 (M + 1). HPLC purity: 96.1%. | 20 |
| 46 | (1'R,2'R)-5'-Methyl-4-(methyl(pyridin-3-yl)amino)-2'-(prop-1-en-2-yl)-1',2',3',4'-tetrahydro-[1, 1'-biphenyl]-2,6-diol | $^{1}$H NMR (400 MHz, DMSO) δ 8.88-8.85 (m, 2H), 8.20 (d, J = 2.4 Hz, 1H), 8.05 (dd, J = 1.6, 4.4 Hz, 1H), 7.30-7.23 (m, 2H), 5.97 (s, 2H), 5.13 (s, 1H), 4.55-4.48 (m, 2H), 3.84 (dd, J = 1.9, 10.5 Hz, 1H), 3.17 (s, 3H), 3.08-2.99 (m, 1H), 2.17-2.06 (m, 1H), 1.95-1.91 (m, 1H), 1.73-1.63 (m, 2H), 1.63-1.61 (m, 6H). MS (ESI): m/z 351.5 (M + 1). HPLC purity: 98.4%. | 20 |
| 47 | (1'R,2'R)-5'-Methyl-2'-(prop-1-en-2-yl)-4-(pyridin-3-yloxy)-1',2',3',4'-tetrahydro-[1,1'-biphenyl]-2,6-diol | $^{1}$H NMR (400 MHz, DMSO) d 9.32 (s, 1H), 9.21 (s, 1H), 8.22 (d, J = 3.3 Hz, 1H), 8.19 (d, J = 2.8 Hz, 1H), 7.33 (dd, J = 4.4, 8.2 Hz, 1H), 7.18 (dd, J = 1.5, 8.3 Hz, 1H), 6.12 (d, J = 2.3 Hz, 1H), 5.71 (d, J = 2.3 Hz, 1H), 4.98-4.96 (m, 1H), 4.48 (s, 2H), 3.72-3.62 (m, 1H), 2.84-2.77 (m, 1H), 1.93-1.93 (m, 1H), 1.84-1.79 (m, 1H), 1.62-1.51 (m, 6H), 1.38-1.22 (m, 2H). MS (ESI): m/z 338.4 (M + 1). HPLC purity: 95.3%. | 2q |

TABLE 1-continued

Detailed information of each compound 1-48 including name, analytical data and indication of synthetic route

| Compound | Name | Analytical data | Synthetic route (Scheme no.) |
|---|---|---|---|
| 48 | (1'R,2'R)-4-(1-(2-Hydroxypropyl)-1H-pyrazol-4-yl)-5'-methyl-2'-(prop-1-en-2-yl)-1',2',3',4'-tetrahydro-[1,1'-biphenyl]-2,6-diol (Mixture of epimers) | $^1$H NMR (400 MHz, DMSO) d 8.88 (s, 2H), 7.81 (s, 1H), 7.56 (s, 1H), 6.36 (s, 2H), 5.14 (s, 1H), 4.92 (d, J = 4.8 Hz, 1H), 4.52 (d, J = 2.5 Hz, 1H), 4.44-4.43 (m, 1H), 4.04-3.96 (m, 3H), 3.89-3.85 (m, 1H), 3.10-3.02 (m, 1H), 2.19-2.08 (m, 1H), 1.98-1.91 (m, 1H), 1.71-1.64 (m, 2H), 1.63 (s, 3H), 1.61 (s, 3H), 1.04 (d, J = 5.8 Hz, 3H). MS (ESI): m/z 369.4 (M + 1). HPLC purity: 96.6%. | 2b |

Example 2: Evaluation of Cannabinoid Derivatives for Anticonvulsant Activity Using the Maximal Electroshock Seizure Threshold (MEST) Test in the Mouse Model Using Minimal Samples Sizes (Mini MEST)

The efficacy of exemplary cannabinoid derivatives of 1 to 5 were tested in a novel mouse model of generalised seizure, the mini-MEST (maximal electroshock seizure threshold) test, which uses lower n numbers than typically used.

The maximal electroshock seizure threshold (MEST) test is widely utilized preclinically to evaluate pro- or anti-convulsant properties of test compounds (Loscher et al., 1991).

In the MEST test the ability of a drug to alter the seizure threshold current required to induce hind limb tonic extensor convulsions is measured according to an "up and down" method of shock titration (Kimball et al., 1957). An increase in seizure threshold is indicative of anti-convulsant effect. Antiepileptic drugs including the sodium channel blockers (e.g. lamotrigine) with clinically proven efficacy against generalised tonic-clonic seizures all exhibit anti-convulsant properties in this test in the mouse.

Conversely, a reduction in seizure threshold is indicative of a pro-convulsant effect as observed with known convulsant agents such as picrotoxin.

The ability of a test compound to alter the stimulus intensity, expressed as current (mA), required to induce the presence of tonic hind limb extensor convulsions, is assessed in the MEST. The outcome of the presence (+) or absence (0) of tonic hind limb extensor convulsions observed from a current to produce tonic hind limb extension in 50% of animals in the treatment group ($CC_{50}$) determines the seizure threshold for the treatment group and the effects were then compared to the $CC_{50}$ of the vehicle control group.

Methods

Study Details

Naïve mice were acclimatised to the procedure room in their home cages for up to 7 days, with food and water available ad libitum.

All animals were weighed at the beginning of the study and randomly assigned to treatment groups based on a mean distribution of body weight across groups. All animals were dosed at 10 mL/kg via intraperitoneal (i.p) injection, with either vehicle, test compound at 5-50 mg/kg, or diazepam at 2.5 mg/kg.

Animals were individually assessed for the production of a tonic hind limb extensor convulsion at 30 min post-dose for vehicle, 15-30 min post-dose for test compound (dependant on compound) and 30 min post-dose for diazepam, from a single electroshock.

The first animal within a treatment group was given a shock at the expected or estimated $CC_{50}$ current. For subsequent animals, the current was lowered or raised depending on the convulsions outcome from the preceding animal in log scale intervals.

Data generated from each treatment group were used to calculate the $CC_{50}$ ±SEM values for the treatment group.

Test Compounds

Vehicle: (5% ethanol, 10% solutol in 85% Saline) was prepared as follows: 1 mL of ethanol, 2 mL of solutol were warmed to 60 °C, in 17 mL of saline (1:2:17).

Positive control: diazepam was used at 2.5 mg/kg.

The test compounds used were 1, 2, 3, 4 and 5. Test compounds were administered at 5-50 mg/kg (i.p.) in a 1:2:17 ethanol:solutol:saline formulation.

Sample Collection

Each animal was humanely killed immediately after production of a convulsion by destruction of the brain from striking the cranium, followed by the confirmation of permanent cessation of the circulation from decapitation under The Humane Killing of Animals under Schedule 1 to the Animals (Scientific Procedures) Act 1986. Terminal blood and brain collection were performed following decapitation.

Blood was collected in Lithium-heparin tubes and centrifuged at 4 °C for 10 minutes at 1500×g. The resulting plasma was removed (>100 µL) and split into 2 aliquots of 0.5 mL Eppendorf tubes containing 10 µL of ascorbic acid (100 mg/mL) for stabilisation. Brains were removed, washed in saline and halved. Each half was placed into separate 2 mL screw cap cryovials, weighed and frozen on cardice.

Statistical Analysis

The data for each treatment group were recorded as the number of +'s and 0's at each current level employed and this information is then used to calculate the $CC_{50}$ value (current required for 50% of the animals to show seizure behaviour) ±standard error.

Test compound effects were also calculated as percentage change in $CC_{50}$ from the vehicle control group.

Significant difference between drug-treated animals and controls were assessed according to Litchfield and Wilcoxon (1949).

Results

FIGS. 1 to 3 and Tables 2 to 4 describe the data produced in this experiment.

In the vehicle groups, the $CC_{50}$ values were calculated to be 22.5-25.0 mA.

In the diazepam (2.5 mg/kg) treated groups, administered i.p. 30 minutes before the test, the $CC_{50}$ values were 75.0-89.0 mA. These results were statistically significant ($p<0.001$) compared to their respective vehicle controls.

In the test compound treatment groups, administered i.p. between 15 and 30 minutes before the test, all five compounds produced a statistically significant $CC_{50}$ value compared to vehicle in at least one dose.

Such data are indicative that these compounds will be of therapeutic benefit.

TABLE 2

Evaluation of effect of Compound 1 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 24.5 +/− 0.9 | — | — |
| Diazepam | 2.5 | 30 | 6 | 75.0 +/− 3.4 | P < 0.001 | 206% |
| Compound 1 | 50 | 30 | 6 | 119.5 +/− 1.9 | P < 0.001 | 388% |

TABLE 3

Evaluation of effect of Compound 2 and 3 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 25.0 +/− 1.3 | — | — |
| Diazepam | 2.5 | 30 | 6 | 87.5 +/− 0.5 | P < 0.001 | 250% |
| Compound 2 | 5 | 15 | 6 | 32.5 +/− 0.7 | P < 0.001 | 30% |
| Compound 2 | 50 | 30 | 6 | <35.0 | # | <40% |
| Compound 3 | 5 | 15 | 6 | 27.5 +/− 0.7 | n.s. | 10% |
| Compound 3 | 50 | 30 | 6 | 62.5 +/− 0.7 | P < 0.001 | 150% |

Statistical significance not determined as $CC_{50}$ was not reached.
n.s. No statistically significant differences from vehicle was observed

TABLE 4

Evaluation of effect of Compound 4 and 5 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 22.5 +/− 0.9 | — | — |
| Diazepam | 2.5 | 30 | 6 | 89.0 +/− 3.4 | P < 0.001 | 296% |
| Compound 4 | 5 | 15 | 6 | 28.3 +/− 1.1 | P < 0.001 | 26% |
| Compound 4 | 50 | 30 | 6 | 70.5 +/− 5.8 | P < 0.001 | 213% |
| Compound 5 | 50 | 30 | 6 | 60.5 +/− 7.8 | P < 0.001 | 169% |

Conclusions

These data demonstrate a therapeutic effect for the compounds.

These data are significant as they provide heretofore unknown evidence that these novel cannabinoid derivatives may be of therapeutic value.

The compounds tested were those detailed as compound 1, compound 2, compound 3, compound 4 and compound 5. Such compounds are examples of the cannabinoid analogues of general Formula I.

Clearly as all compounds showed efficacy in the mini-MEST test such therapeutic efficacy can be attributed to the cannabinoid analogues of general Formula I of the invention.

Example 3: Evaluation of Cannabinoid Derivatives for Anticonvulsant Activity Using the Maximal Electroshock Seizure Threshold (MEST) Test in the Mouse Using Minimal Sample Sizes (Mini-MEST)

The efficacy of exemplary cannabinoid derivatives of 12, 42 and 43 were tested in a novel mouse model of generalised seizure, the mini-MEST (maximal electroshock seizure threshold) test, which uses lower n numbers than typically used.

Methods

Study Details, Sample Collection and Statistical Analysis

The protocol according to Example 2 was followed.

Test Compounds

Vehicle: (5% ethanol, 10% solutol in 85% Saline) was prepared as follows: 1 mL of ethanol, 2 mL of solutol were warmed to 60 °C, in 17 mL of saline (1:2:17).

Positive control: diazepam was used at 2.5 mg/kg.

The test compounds used were 12, 42 and 43. Test compounds were administered at 5-50 mg/kg (i.p.) in a 1:2:17 ethanol:solutol:saline formulation.

Results

FIGS. 4 to 6 and Tables 5 to 7 describe the data produced in this experiment.

In the vehicle groups, the $CC_{50}$ values were calculated to be 26.5-29.7 mA.

In the diazepam (2.5 mg/kg) treated groups, administered i.p. 30 minutes before the test, the $CC_{50}$ values were 97.8-128.0 mA. These results were statistically significant ($p<0.001$) compared to their respective vehicle controls.

In the test compound treatment groups, administered i.p. between 15 and 30 minutes before the test, all three compounds produced a statistically significant $CC_{50}$ value compared to vehicle in at least one dose. Statistical significance could not be determined for Compound 12 at 50 mg/kg as $CC_{50}$ was not reached, but no animals had any convulsions at this dose, indicating clear anticonvulsant activity.

Such data are indicative that these compounds will be of therapeutic benefit.

TABLE 5

Evaluation of effect of Compound 12 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 26.5 +/− 1.9 | — | — |
| Diazepam | 2.5 | 30 | 6 | 121.0 +/− 9.0 | P < 0.001 | 357% |
| Compound 12 | 5 | 15 | 6 | 25.0 +/− 1.1 | n.s. | −6% |
| Compound 12 | 50 | 30 | 6 | >131 | # | >394% |

Statistical significance not determined as $CC_{50}$ was not reached.
n.s.—No statistically significant differences from vehicle was observed

TABLE 6

Evaluation of effect of Compound 42 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 26.5 +/− 1.9 | — | — |
| Diazepam | 2.5 | 30 | 6 | 128.0 +/− 5.2 | P < 0.001 | 483% |
| Compound 42 | 50 | 30 | 6 | 67.5 +/− 2.6 | P < 0.001 | 132% |

TABLE 7

| Evaluation of effect of Compound 43 in the mini-MEST test | | | | | | |
|---|---|---|---|---|---|---|
| Treatment | Dose (mg/kg) | Test time post dose (min) | N | $CC_{50}$ +/− SEM | Significance | % change from vehicle |
| Vehicle | — | 30 | 6 | 29.7 +/− 1.1 | — | — |
| Diazepam | 2.5 | 30 | 6 | 97.8 +/− 3.7 | P < 0.001 | 230% |
| Compound 43 | 50 | 30 | 6 | 58.2 +/− 2.0 | P < 0.001 | 96% |

Conclusions

These data demonstrate a therapeutic effect for the compounds in at least one concentration tested.

These data are significant as they provide heretofore unknown evidence that these novel cannabinoid derivatives may be of therapeutic value.

The compounds tested were those detailed as compound 12, compound 42, and compound 43. Such compounds are examples of the cannabinoid analogues of general Formula I.

Clearly as all compounds showed efficacy in the mini-MEST test such therapeutic efficacy can be attributed to the cannabinoid analogues of general Formula I of the invention.

Example 4: Evaluation of Cannabinoid Derivative for Anticonvulsant Activity Using the Maximal Electroshock Seizure Threshold (MEST) Test in the Mouse The efficacy of the cannabinoid derivative of 1 was tested in a mouse model of generalised seizure, the maximal electroshock seizure threshold (MEST) test.

Methods

Study Details, Sample Collection and Statistical Analysis

The protocol according to Example 2 was followed, with the current lowered or raised in intervals of 5 mA instead of log scale intervals.

Test Compounds

Vehicle: (5% ethanol, 10% solutol, 85% Saline) was prepared as follows: 1 mL of ethanol, 2 mL of solutol were warmed to 60 °C, in 17 mL of saline (1:2:17).

Positive control: diazepam was used at 2.5 mg/kg.

The test compound 1 was administered at 1, 5 and 50 mg/kg (i.p.) in a 1:2:17 ethanol:solutol:0.9% saline formulation.

Results

FIG. 7 and Table 8 describe the data produced in this experiment.

In the vehicle group, the $CC_{50}$ value was calculated to be 26.0 mA.

In the diazepam (2.5 mg/kg) treated group, administered i.p. 30 minutes before the test, the $CC_{50}$ value was 84.2 mA. This result was statistically significant ($p<0.001$) compared to the vehicle control.

In the test compound treatment group, administered i.p. 15-30 minutes before the test, Compound 1 produced a statistically significant $CC_{50}$ value compared to vehicle at all three doses of the compound.

Such data are indicative that this compound will be of therapeutic benefit.

TABLE 8

| Evaluation of effect of Compound 1 in the MEST test | | | | | | |
|---|---|---|---|---|---|---|
| Treatment | Dose (mg/kg) | Test time post dose (min) | N | $CC_{50}$ +/− SEM | Significance | % change from vehicle |
| Vehicle | — | 30 | 12 | 26.0 ± 0.4 | — | — |
| Diazepam | 2.5 | 30 | 12 | 84.2 ± 1.9 | P < 0.001 | 224% |
| Compound 1 | 1 | 15 | 12 | 28.5 ± 1.0 | P < 0.05 | 10% |
| Compound 1 | 5 | 15 | 12 | 31.5 ± 1.0 | P < 0.001 | 21% |
| Compound 1 | 50 | 30 | 12 | 81.5 ± 2.1 | P < 0.001 | 213% |

Conclusions

These data demonstrate a therapeutic effect for compound 1, reaffirming the anticonvulsant activity shown in Example 2 (Table 2).

Clearly the compound produced a dose-related increase in MEST. Significant effects were observed at all doses 1-50 mg/kg, when compared to vehicle.

Example 5: Evaluation of Cannabinoid Derivatives for Anticonvulsant Activity Using the Maximal Electroshock Seizure Threshold (MEST) Test in the Mouse Using Minimal Sample Sizes (Mini-MEST)

The efficacy of exemplary cannabinoid derivatives of 6, 13, 22, 26, 28, 33, 38 and 46 were tested in a novel mouse model of generalised seizure, the mini-MEST (maximal electroshock seizure threshold) test, which uses lower n numbers than typically used.

Methods

Study Details, Sample Collection and Statistical Analysis

The protocol according to Example 2 was followed.

Test Compounds:

Vehicle: (5% ethanol, 10% solutol in 85% Saline) was prepared as follows: 1 mL of ethanol, 2 mL of solutol were warmed to 60 °C, in 17 mL of saline (1:2:17).

Positive control: diazepam was used at 2.5 mg/kg.

The test compounds used were 6, 13, 22, 26, 28, 33, 38 and 46. Test compounds were administered at 5-50 mg/kg (i.p.) in a 1:2:17 ethanol:solutol:saline formulation.

Results

FIGS. 8 to 12 and Tables 9 to 13 describe the data produced in this experiment.

In the vehicle groups, the $CC_{50}$ values were calculated to be 22.5-26.5 mA.

In the diazepam (2.5 mg/kg) treated groups, administered i.p. 30 minutes before the test, the $CC_{50}$ values were 75.0-106.5 mA. These results were statistically significant ($p<0.001$) compared to their respective vehicle controls.

In the test compound treatment groups, administered i.p. between 15 and 30 minutes before the test, seven compounds produced a statistically significant $CC_{50}$ value compared to vehicle in at least one dose.

Such data are indicative that these compounds will be of therapeutic benefit.

TABLE 9

Evaluation of effect of Compound 6 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 24.5 ± 0.9 | — | — |
| Diazepam | 2.5 | 30 | 6 | 75.0 ± 3.4 | P < 0.001 | 206% |
| Compound 6 | 50 | 30 | 6 | <43 | # | <76% |

Statistical significance not determined as $CC_{50}$ was not reached.

TABLE 10

Evaluation of effect of Compound 13 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 23.5 +/− 0.3 | — | — |
| Diazepam | 2.5 | 30 | 6 | 89.0 +/− 3.4 | P < 0.001 | 279% |
| Compound 13 | 5 | 15 | 6 | 25.0 +/− 1.1 | n.s. | 6% |
| Compound 13 | 50 | 30 | 6 | 37.2 +/− 1.1 | P < 0.001 | 58% |

n.s.—No statistically significant differences from vehicle was observed

TABLE 11

Evaluation of effect of Compounds 22 and 38 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 26.5 ± 0.3 | — | — |
| Diazepam | 2.5 | 30 | 6 | 106.5 ± 14.5 | P < 0.001 | 302% |
| Compound 22 | 5 | 15 | 6 | 33.0 ± 9.7 | P < 0.001 | 25% |
| Compound 22 | 50 | 30 | 6 | 66.0 ± 3.4 | P < 0.001 | 149% |
| Compound 38 | 50 | 30 | 6 | 79.5 ± 1.3 | P < 0.001 | 200% |

TABLE 12

Evaluation of effect of Compounds 26, 28 and 33 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 22.5 ± 0.9 | — | — |
| Diazepam | 2.5 | 30 | 6 | 85.0 ± 3.4 | P < 0.001 | 279% |
| Compound 26 | 50 | 30 | 6 | 75.0 ± 3.4 | P < 0.001 | 233% |
| Compound 28 | 5 | 15 | 6 | 25.0 ± 1.1 | P < 0.05 | 11% |
| Compound 28 | 50 | 30 | 6 | 35.5 ± 0.7 | P < 0.001 | 58% |
| Compound 33 | 50 | 30 | 6 | 53.5 ± 4.5 | P < 0.001 | 138% |

TABLE 13

Evaluation of effect of Compound 46 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 26.5 ± 1.9 | — | — |
| Diazepam | 2.5 | 30 | 6 | 128.0 ± 5.2 | P < 0.001 | 383% |
| Compound 46 | 50 | 30 | 6 | 61.5 ± 0.8 | P < 0.001 | 132% |

Conclusions

These data demonstrate a therapeutic effect for the compounds in at least one concentration tested.

These data are significant as they provide heretofore unknown evidence that these novel cannabinoid derivatives may be of therapeutic value.

The compounds tested were those detailed as compound 6, compound 13, compound 22, compound 26, compound 28, compound 33, compound 38 and compound 46. Such compounds are examples of the cannabinoid analogues of general Formula I.

Clearly as the compounds showed efficacy in the mini-MEST test such therapeutic efficacy can be attributed to the cannabinoid analogues of general Formula I of the invention.

Example 6: Evaluation of Cannabinoid Derivatives for Anticonvulsant Activity Using the Maximal Electroshock Seizure Threshold (MEST) Test in the Mouse Using Minimal Sample Sizes (Mini-MEST)

The efficacy of exemplary cannabinoid derivative of 36 were tested in a novel mouse model of generalised seizure, the mini-MEST (maximal electroshock seizure threshold) test, which uses lower n numbers than typically used.

Methods

Study Details, Sample Collection and Statistical Analysis

The protocol according to Example 2 was followed.

Test Compounds

Vehicle: (5% ethanol, 10% solutol in 85% Saline) was prepared as follows: 1 mL of ethanol, 2 mL of solutol were warmed to 60 °C, in 17 mL of saline (1:2:17).

Positive control: diazepam was used at 2.5 mg/kg.

The test compound used was 36. Test compound was administered at 5 and 50 mg/kg (i.p.) in a 1:2:17 ethanol: solutol:saline formulation.

Results

FIG. 13 and Table 14 describe the data produced in this experiment.

In the vehicle groups, the $CC_{50}$ values were calculated to be 25.5 mA.

In the diazepam (2.5 mg/kg) treated groups, administered i.p. 30 minutes before the test, the $CC_{50}$ value was 107.0 mA. This result was statistically significant ($p<0.001$) compared to its vehicle control.

In the test compound treatment group, administered i.p. between 15 and 30 minutes before the test, compound 36 produced a statistically significant $CC_{50}$ value compared to vehicle.

Such data is indicative that this compound will be of therapeutic benefit.

TABLE 14

Evaluation of effect of Compound 36 in the mini-MEST test

| Treatment | Dose (mg/kg) | Test time post dose (min) | N | $CC_{50}$ +/− SEM | Significance | % change from vehicle |
|---|---|---|---|---|---|---|
| Vehicle | — | 30 | 6 | 25.5 ± 0.9 | — | — |
| Diazepam | 2.5 | 30 | 6 | 107.0 ± 0.6 | P < 0.001 | 320% |
| Compound 36 | 5 | 15 | 6 | 29.0 ± 1.5 | P < 0.05 | 14% |
| Compound 36 | 50 | 30 | 6 | 70.5 ± 0.8 | P < 0.001 | 176% |

Conclusions

This data demonstrates a therapeutic effect for the compound.

This data is significant as it provides heretofore unknown evidence that this novel cannabinoid derivative may be of therapeutic value.

The compound tested was that detailed as compound 36. Such compound is an example of the cannabinoid analogue of general Formula I.

Clearly as the compound showed efficacy in the mini-MEST test such therapeutic efficacy can be attributed to the cannabinoid analogues of general Formula I of the invention.

REFERENCES

A number of publications are cited above in order to more fully describe and disclose the invention and the state of the art to which the invention pertains. Full citations for these references are provided below. The contents of each of these references is incorporated herein.

1. Gong et al., "Synthesis of CBD and Its Derivatives Bearing Various C4'-Side Chains with a Late-Stage Diversification Method", *J. Org. Chem,* 2020, Vol. 85, pp. 2704-2715.

The invention claimed is:

1. A compound of formula (I), or a pharmaceutically acceptable salt thereof, (I)

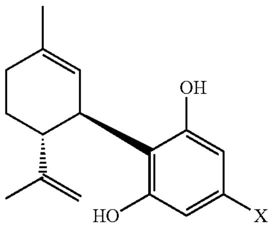

where X is one of the following:

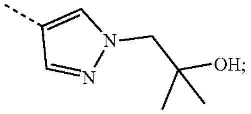

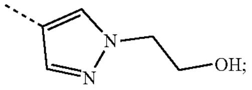

-continued

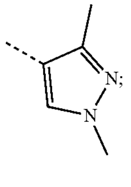

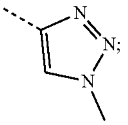

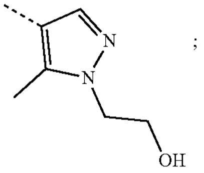

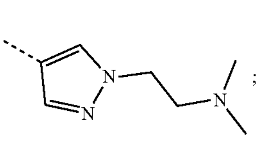

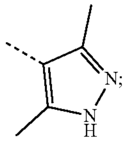

-continued

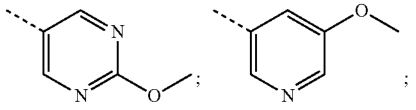

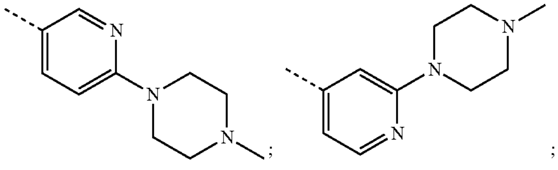

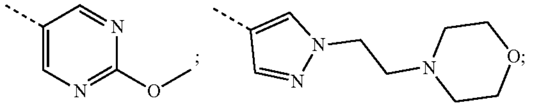

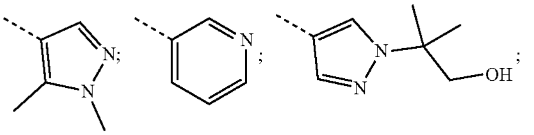

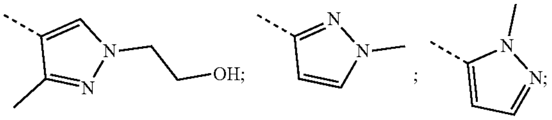

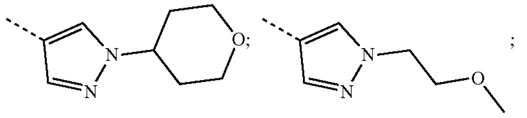

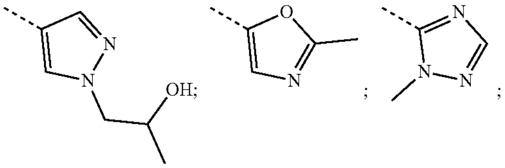

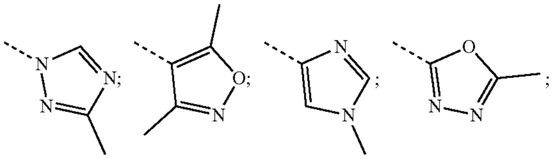

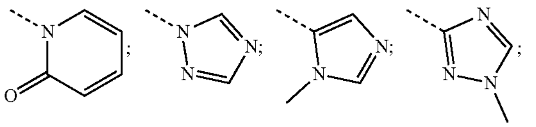

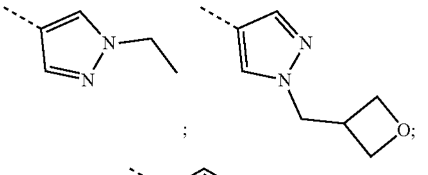

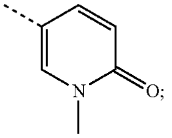

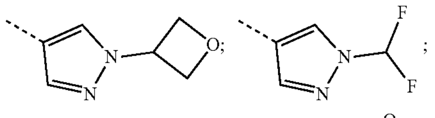

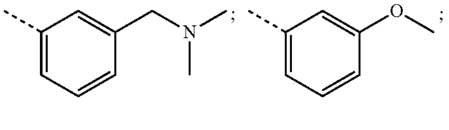

-continued

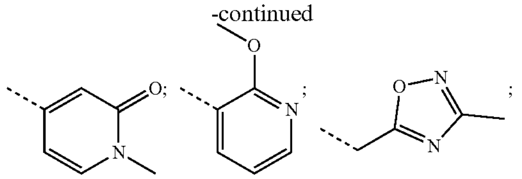

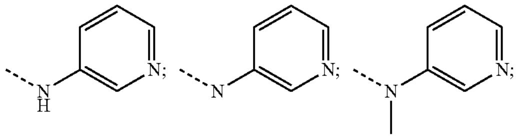

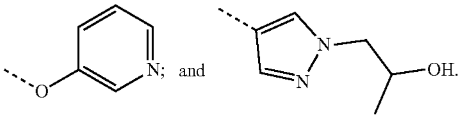

2. A pharmaceutical composition comprising the compound of claim 1 or the pharmaceutically acceptable salt thereof and one or more pharmaceutically acceptable additional ingredients selected from a carrier a diluent, excipient, an adjuvant, a filler, a buffer, a binder, a disintegrant, a preservative, an antioxidant, a lubricant, a stabilizer, a solubilizer, a surfactant, a masking agent, a coloring agent, a flavoring agent, and a sweetening agent.

3. The pharmaceutical composition of claim 2 in a form selected from a liquid, a solution, a suspension, an emulsion, a syrup, an electuary, a mouthwash, a drop, a tablet, a granule, a powder, a lozenge, a pastille, a capsule, a cachet, a pill, an ampoule, a bolus, a suppository, a pessary, a tincture, a gel, a paste, an ointment, a cream, a lotion, an oil, a foam, a spray, and an aerosol.

4. A method of preparing the compound of claim 1 or the pharmaceutically acceptable salt thereof, the method comprising:

(1a) reacting a compound of formula (II) with a compound of formula (III):

(II)

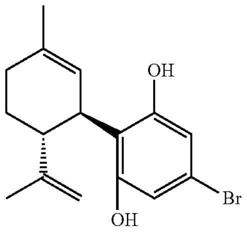

(III)

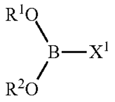

where:

$R^1$ and $R^2$ are OH; or $R^1$ and $R^2$ together form —OC(Me)$_2$C(Me)$_2$O—; and $X^1$ is selected from:

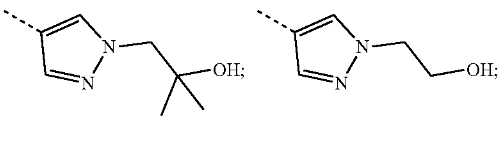

-continued

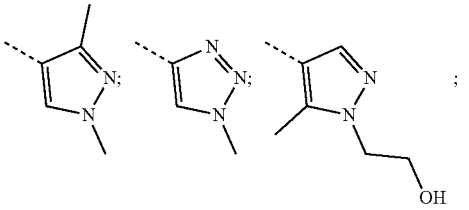
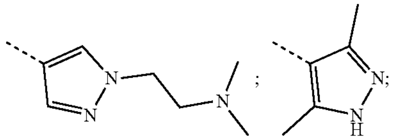
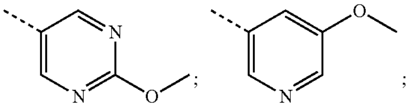
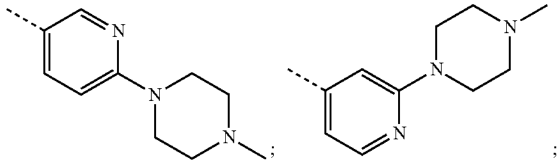
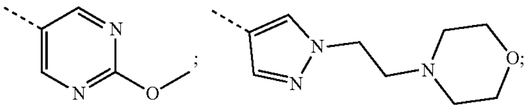
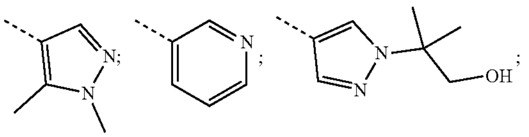
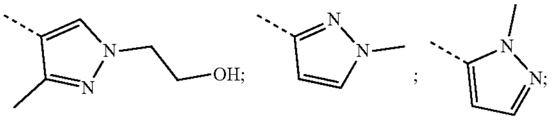
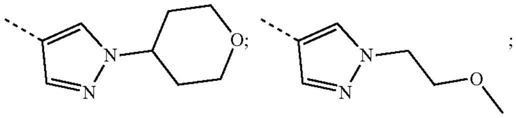
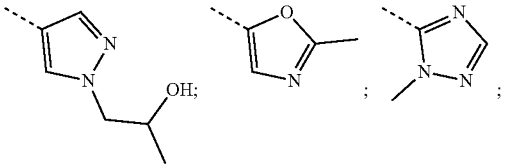
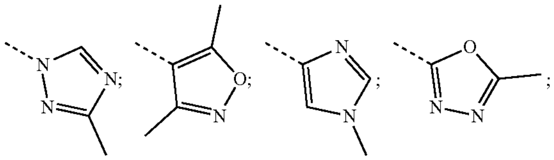
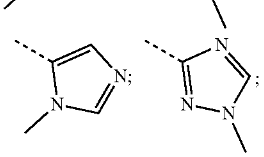
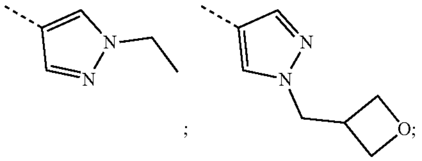

-continued

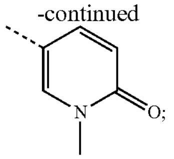
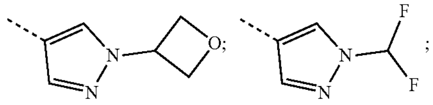
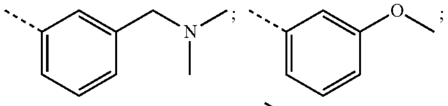
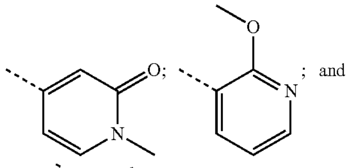
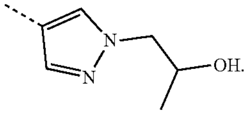

5. The method of claim 4, wherein step (1a) comprises reacting a compound of formula (II) with a compound of formula (III) and a palladium catalyst.

6. A method of preparing the compound of claim 1 or the pharmaceutically acceptable salt thereof, the method comprising:

(2a) reacting a compound of formula (II) with bis (pinacolato) diboron; and (2b) reacting the product of step (2a) with a compound of formula (IV), (II)

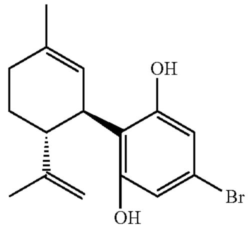

(IV)

Br—$X^2$ where:

$X^2$ is selected from:

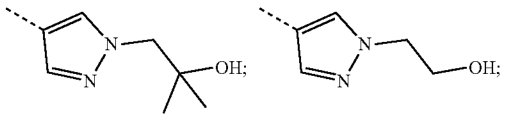
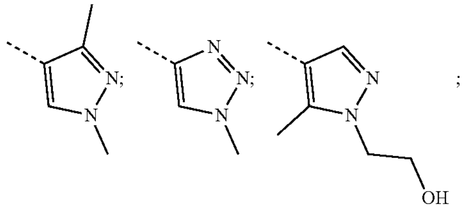

-continued

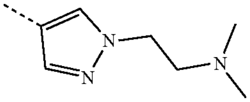 ; 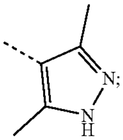

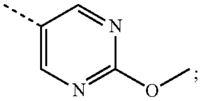 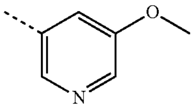 ;

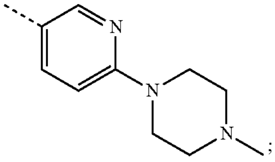 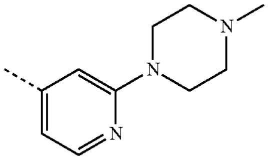 ;

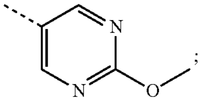 ; 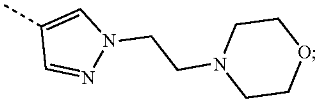

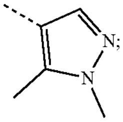 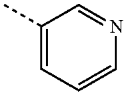 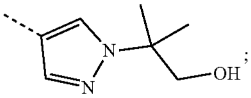 ;

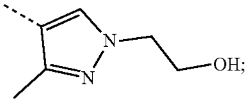 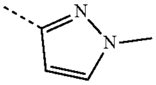 ; 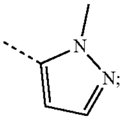

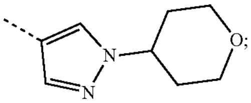 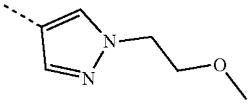 ;

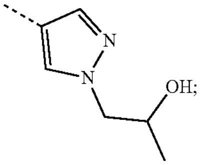 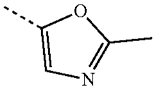 ; 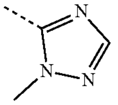 ;

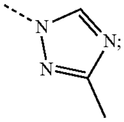 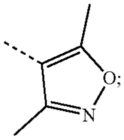 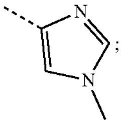 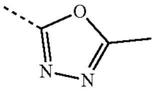 ;

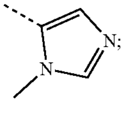 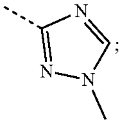

-continued

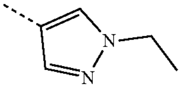 ; 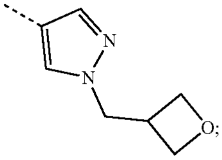

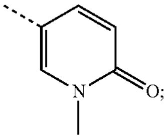

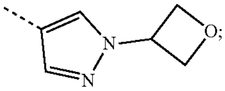 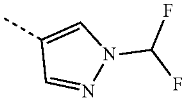 ;

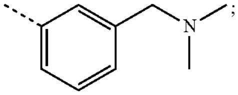 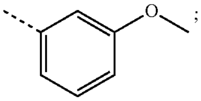 ;

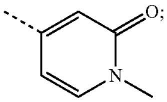 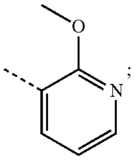 ; and

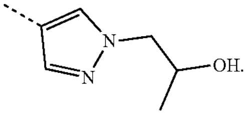

7. The method of claim 6, wherein step (2a) comprises reacting a compound of formula (II) with bis (pinacolato) diboron and a palladium catalyst.

8. The method of claim 6, wherein step (2b) comprises reacting the product of step (2a) with a compound of formula (IV) and a palladium catalyst.

9. A method of treating epilepsy in a subject in need thereof, the method comprising administering to the subject the compound of claim 1 or the pharmaceutically acceptable salt thereof.

10. A method of treating generalised seizure in a subject in need thereof, the method comprising administering to the subject the compound of claim 1 or the pharmaceutically acceptable salt thereof.

11. A method of treating tonic-clonic seizure in a subject in need thereof, the method comprising administering to the subject the compound of claim 1 or the pharmaceutically acceptable salt thereof.

12. A method of treating seizures in a subject in need thereof, the method comprising administering to the subject the compound of claim 1 or the pharmaceutically acceptable salt thereof.

* * * * *